United States Patent [19]

Ogawa et al.

[11] Patent Number: 5,244,898
[45] Date of Patent: Sep. 14, 1993

[54] BENZOHETEROCYCLIC COMPOUNDS

[75] Inventors: Hidenori Ogawa; Kazumi Kondo; Hiroshi Yamashita; Kenji Nakaya, all of Tokushima; Hajime Komatsu, Tokyo; Michinori Tanaka, Tokushima; Kazuyoshi Kitano, Tokyshima; Michiaki Tominaga, Tokushima; Yoichi Yabuuchi, Tokushima, all of Japan

[73] Assignee: Otsuka Pharmaceutical Co., Ltd., Tokyo, Japan

[21] Appl. No.: 870,318

[22] Filed: Apr. 17, 1992

[30] Foreign Application Priority Data

Apr. 19, 1991 [JP] Japan .................. 3-087994

[51] Int. Cl.$^5$ ............... A61K 31/55; C07D 223/16
[52] U.S. Cl. .......................... 514/213; 540/593
[58] Field of Search ............... 540/593, 583; 546/148; 544/235; 514/213

[56] References Cited

FOREIGN PATENT DOCUMENTS

| 0255134 | 2/1988 | European Pat. Off. ......... 514/255 |
| 2459669 | 10/1969 | Japan ....................... 514/312 |
| 51-118773 | 10/1976 | Japan ....................... 514/312 |
| 59-70671 | 4/1984 | Japan ....................... 546/157 |
| 1121411 | 7/1968 | United Kingdom ............. 546/157 |

OTHER PUBLICATIONS

Lobbezoo et al, *J. Med. Chem.*, 24:777–782 (1981).
Yamamura et al, *Science*, 252:572–574 (1991).
*Chemical Abstracts*, 81:450 (Abstract No. 77786r) 1974.
*Chemical Abstracts*, 102:17 (Abstract No. 143336z) 1985.
*Chemical Abstracts*, 108:13 (Abstract No. 112151e) 1987.
Okada et al, *Biochem. Biophys. Res. Comm.*, 178:707–712 (1991).

Primary Examiner—Mukund J. Shah
Assistant Examiner—E. C. Ward
Attorney, Agent, or Firm—Sughrue, Mion, Zinn, Macpeak & Seas

[57] ABSTRACT

Novel benzoheterocyclic compounds of the formula:

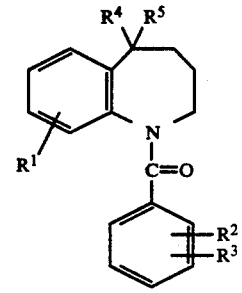

wherein $R^1$ is H, halogen, OH, etc.; $R^2$ is H, alkyl, halogen or alkoxy; $R^3$ is phenyl-alkanoylamino, or

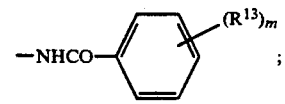

$R^4$ is H, $-NR^6R^7$, alkenyloxy, HO-alkyl, $-O-CO-A-NR^8R^9$, etc.; $R^5$ is H, OH, etc., or a salt thereof, which have excellent vasopressin antagonistic activities and useful as vasodilator, hypotensive agent, water diuretics, platelet agglutination inhibitor, and a vasopressin antagonistic composition containing the compound as the active ingredient.

30 Claims, No Drawings

BENZOHETEROCYCLIC COMPOUNDS

The present invention relates to novel benzoheterocyclic compounds which have excellent vasopressin antagonistic activities and are useful as vasodilator, hypotensive agent, water diuretics, platelet agglutination inhibitor.

The benzoheterocyclic compounds of the present invention and pharmaceutically acceptable salts thereof are novel compounds which have never been disclosed in any literature, and are useful as a medicament.

The present invention provides a benzoheterocyclic compound of the formula:

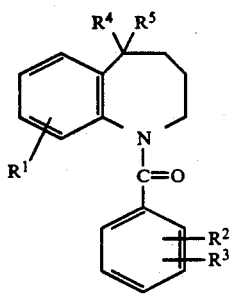

wherein $R^1$ is hydrogen atom; a halogen atom; hydroxy group; a lower alkanoyloxy group; an amino-lower alkoxy group which may optionally be substituted by a group selected from a lower alkyl group and a lower alkanoyl group; a carboxy-substituted lower alkoxy group; a lower alkoxycarbonyl-substituted lower alkoxy group; or an aminocarbonyl-lower alkoxy group which may optionally be substituted by a lower alkyl group, $R^4$ is hydrogen atom; a group of the formula —$NR^6R^7$ (wherein $R^6$ and $R^7$ are the same or different and are hydrogen atom, a lower alkyl group or a lower alkenyl group); a lower alkenyloxy group; a hydroxy-substituted lower alkyl group; a group of the formula: —O—CO—A—$NR^8R^9$ (wherein A is a lower alkylene group, $R^8$ and $R^9$ are the same or different and are hydrogen atom or a lower alkyl group, and $R^8$ and $R^9$ may bind together with the adjacent nitrogen atom to which they bind to form a 5- or 6-membered, saturated or unsaturated heterocyclic ring which may be intervened or not with nitrogen or oxygen atom, wherein the said heterocyclic ring may optionally have a lower alkyl substituent); a group of the formula: —O—$R^{10}$ (wherein $R^{10}$ is an amino acid residue.); a lower alkoxycarbonyl-substituted lower alkylidene group; a lower alkoxycarbonyl-substituted lower alkyl group; a carboxy-substituted lower alkyl group; a group of the formula: —A—$CONR^{11}R^{12}$ (wherein A is the same as defined above, $R^{11}$ and $R^{12}$ are the same or different and are hydrogen atom, a lower alkyl group, a piperidinyl group which may optionally be substituted by a phenyl-lower alkyl group on the piperidine ring, or a carbamoyl-lower alkyl group, and $R^{11}$ and $R^{12}$ may bind together with the adjacent nitrogen atom to which they bind to form a 5- or 6-membered, saturated heterocyclic ring which may be intervened or not with nitrogen or oxygen atom, wherein the said heterocyclic ring may optionally be substituted by a group selected from a lower alkyl group, a lower alkoxycarbonyl group and an amino group optionally having a substituent selected from a lower alkyl group and a lower alkanoyl group); a group of the formula:

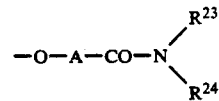

(wherein A is the same as defined above, $R^{23}$ and $R^{24}$ are the same or different and are hydrogen atom, a lower alkoxycarbonyl-substituted lower alkyl group, a carboxy-substituted lower alkyl group, or a piperidinyl group which may optionally be substituted by a lower alkyl group on the piperidine ring); a pyrrolidinylcarbonyl-lower alkoxy group which is substituted by a lower alkoxycarbonyl group on the pyrrolidine ring; a lower alkoxy-substituted lower alkanoyloxy group; a group of the formula:

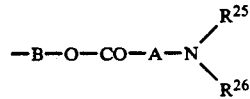

(wherein A is the same as defined above, B is a lower alkylene group, $R^{25}$ and $R^{26}$ are the same or different and are hydrogen atom or a lower alkyl group); an amino-substituted lower alkylidene group wherein the amino moiety may optionally be substituted a lower alkyl group; a group of the formula:

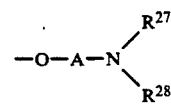

(wherein A is the same as defined above, $R^{27}$ and $R^{28}$ bind together with the adjacent nitrogen atom to which they bind to form a 5- or 10-membered, saturated or unsaturated heteromonocyclic ring or heterobicyclic ring which may be intervened or not with nitrogen or oxygen atom, wherein the said heterocyclic ring may optionally be substituted by a group selected from an oxo group, a lower alkyl group, a lower alkoxycarbonyl group and a lower alkanoyl group); cyano group; a cyano-substituted lower alkyl group; a lower alkoxy group having a substituent selected from hydroxy group and a phenylsulfonyloxy group optionally being substituted by a lower alkyl group on the phenyl ring; a group of the formula:

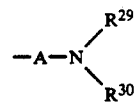

(wherein A is the same as defined above, $R^{29}$ and $R^{30}$ bind together with the adjacent nitrogen atom to which they bind to form a 5- or 6-membered, saturated heterocyclic ring which may be intervened or not with nitrogen or oxygen atom, wherein the said heterocyclic ring may optionally be substituted by a group selected from a lower alkyl group, a lower alkanoyl group and an amino group optionally having a lower alkyl substituent); a phenylsulfonyloxy-substituted lower alkyl group which may optionally be substituted by a lower alkyl group on the phenyl ring; a phthalimido-substituted lower alkyl group; or a cyano-substituted lower alkylidene group, $R^5$ is hydrogen atom or hydroxy group, and $R^4$ and $R^5$ may combine together to form an oxo group, $R^2$ is hydrogen atom, a lower alkyl group, a halogen atom or a lower alkoxy group, $R^3$ is a group of the formula:

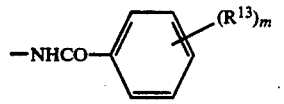

(wherein $R^{13}$ is a halogen atom, carbamoyl group, a lower alkyl group, a piperazinyl-lower alkoxy group which is substituted by a lower alkanoyl group on the 4-position of the piperazine ring, m is 0 or an integer of 1 to 3) or a phenyl-lower alkanoylamino group which is substituted by 1 to 3 groups selected from a halogen atom, a lower alkoxy group, a lower alkyl group and nitro group on the phenyl ring, provided that when $R^1$ is hydrogen atom or a halogen atom, $R^4$ is hydrogen atom, a group of the formula: $-NR^6R^7$ (wherein $R^6$ and $R^7$ are the same as defined above), a group of the formula:

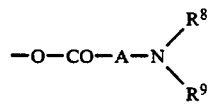

(wherein A is the same as defined above, and $R^8$ and $R^9$ are the same or different and are hydrogen atom or a lower alkyl group) or a hydroxy-substituted lower alkyl group, and $R^5$ is hydrogen atom, hydroxy group or $R^4$ and $R^5$ combine together to form an oxo group, $R^3$ is a group of the formula:

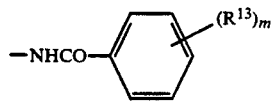

(wherein $R^{13}$ is carbamoyl group, or a piperazinyl-lower alkoxyl group which is substituted by a lower alkanoyl group on the 4-position of the piperazine ring, and m is the same as defined above), or a salt thereof.

The present inventors have intensively studied and have found that the benzoheterocyclic compounds and salts thereof of the present invention have excellent vasopressin antagonistic activities.

The benzoheterocyclic compounds of the formula (1) and their salts of the present invention have excellent vasopressin antagonistic activities and vasodilating activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor in the treatment or prophylaxis of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formula (1) includes specifically the following groups.

The "lower alkoxy" includes a straight chain or branched chain alkoxy group having 1 to 6 carbon atoms, for example, methoxy, ethoxy, propoxy, isopropoxy, butoxy, tert-butoxy, pentyloxy, hexyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "halogen atom" includes fluorine atom, chlorine atom, bromine atom, and iodine atom.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkenyloxy" includes a straight chain or branched chain alkenyloxy group having 2 to 6 carbon atoms, for example, vinyloxy, allyloxy, 2-butenyloxy, 3-butenyloxy, 1-methylallyloxy, 2-pentenyloxy, 2-hexenyloxy, and the like.

The "lower alkylene" includes a straight or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyloxy" includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, an the like.

The "hydroxy-substituted lower alkyl" includes a straight chain or branched chain alkyl group having 1 to 6 carbon atoms which is substituted by 1 to 3 hydroxy groups, for example, hydroxymethyl, 2-hydroxyethyl, 1-hydroxyethyl, 3-hydroxypropyl, 2,3-dihydroxyethyl, 4-hydroxybutyl, 3,4-dihydroxybutyl, 1,1-dimethyl-2-hydroxyethyl, 5-hydroxypentyl, 6-hydroxyhexyl, 2-methyl-3-hydroxypropyl, 2,3,4-trihydroxybutyl, and the like.

The "aminocarbonyl-lower alkoxy which has a lower alkyl substituent" includes a straight chain or branched chain alkoxy group having 1 to 6 carbon atoms which has an aminocarbonyl groups being substituted by 1 to 2 straight chain or branched chain alkyl group having 1 to 6 carbon atoms, for example, methylaminocarbonylmethoxy, 1-ethylaminocarbonylethoxy, 2-propylaminocarbonylethoxy, 3-isopropylaminocarbonylpropoxy, 4-butylaminocarbonylbutoxy, 5-pentylaminocarbonylpentyloxy, 6-hexylaminocarbonylhexyloxy, dimethylaminocarbonylmethoxy, 3-diethylaminocarbonylpropoxy, diethylaminocarbonylmethoxy, (N-ethyl-N-propylamino)carbonylmethoxy, 2-(N-methyl-N-hexylamino)carbonylethoxy, and the like.

The "lower alkoxylcarbonyl-substituted lower alkyl" includes a straight chain or branched chain having 1 to 6 carbon atoms which is substituted by a straight chain or branched chain alkoxycarbonyl group having 1 to 6 carbon atoms, for example, methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The "carboxy-substituted lower alkyl" includes a carboxyalkyl group wherein the alkyl moiety is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "phenyl-lower alkanoylamino which is substituted by 1 to 3 groups selected from a halogen atom, a lower alkoxy, a lower alkyl or nitro on the phenyl ring" includes phenylalkanoylamino group wherein the alkanoyl moiety is a straight chain or branched chain alkanoyl group having 2 to 6 carbon atoms, and which is substituted by 1 to 3 groups selected from a straight chain or branched chain alkyl group having 1 to 6 carbon atoms, a straight chain or branched chain alkoxy group having 1 to 6 carbon atoms, a halogen atom and nitro group on the phenyl ring, for example, 2-methoxyphenylacetylamino, 3-methoxyphenylacetylamino, 4-methoxyphenylacetylamino, 3-(2-ethoxyphenyl)propionylamino, 2-(3-ethoxyphenyl)propionylamino, 4-(4-ethoxyphenyl)butyrylamino, 2,2-dimethyl-3-(4-isopropoxyphenyl)propionylamino, 5-(4-pentyloxyphenyl)pentanoylamino, 2,4-dimethoxyphenylacetylamino, 4-hexyloxyphenylacetylamino, 3,4-dimethoxyphenylacetylamino, 2-(3-ethoxy-4-methoxyphenyl)propionylamino, 3-(2,3-dimethoxyphenyl)propionylamino, 4-(3,4-diethoxyphenyl)butyrylamino, 2,5-dimethoxyphenylacetylamino, 6-(2,6-dimethoxyphenyl)hexanoylamino, 3,5-dimethoxyphenylacetylamino, 3,4-dipentyloxyphenylacetylamino, 3,4,5-trimethoxyphenylacetylamino, 2-chlorophenylacetylamino, 3-chlorophenylacetylamino, 4-chlorophenylacetylamino, 2-fluorophenylacetylamino, 3-fluorophenylacetylamino, 3 (4-fluorophenyl)propionylamino, 2-(2-bromophenyl)propionylamino, 4-(3-bromophenyl)butyrylamino, 5-(4-bromophenyl)pentanoylamino, 6-(2-iodophenyl)hexanoylamino, 3-iodophenylacetylamino, 3-(4-iodophenyl)propionylamino, 4-(3,4-dichlorophenyl)butyrylamino, 3,4-dichlorophenylacetylamino, 2,6-dichlorophenylacetylamino, 2,3-dichlorophenylacetylamino, 2,4-dichlorophenylacetylamino, 3,4-difluorophenylacetylamino, 3-(3,5-dibromophenyl)propionylamino, 3,4,5-trichlorophenylacetylamino, 2-methoxy-3-chlorophenylacetylamino, 2-methylphenylacetylamino, 3-methylphenylacetylamino, 4-methylphenylacetylamino, 3-(2-ethylphenyl)propionylamino, 2-(3-ethylphenyl)propionylamino, 4-(4-ethylphenyl)butyrylamino, 5-(4-isopropylphenyl)pentanoylamino, 6-(3-butylphenyl)hexanoylamino, 3-(4-pentylphenyl)propionylamino, 4-hexylphenylacetylamino, 3,4-dimethylphenylacetylamino, 3,4-diethylphenylacetylamino, 2,4-dimethylphenylacetylamino, 2,5-dimethylphenylacetylamino, 2,6-dimethylphenylacetylamino, 3,4,5,-trimethylphenylacetylamino, 3-chloro-4-methylphenylacetylamino, 3-methoxy-4-methyl-5-iodophenylacetylamino, 3,4-dimethoxy-5-bromophenylacetylamino, 3,5-diiodo-4-methoxyphenylacetylamino, 2-nitrophenylacetylamino, 3-nitrophenylacetylamino, 3,4-dinitrophenylacetylamino, 3,4,5-trinitrophenylacetylamino, and the like.

The "lower alkoxycarbonyl-substituted lower alkylidene" includes a straight chain or branched chain alkylidene group having 1 to 6 carbon atoms which is substituted by a straight chain or branched chain alkoxycarbonyl group having 1 to 6 carbon atoms, for example, ethoxycarbonylmethylidene, 2-methoxycarbonylethylidene, 3-isopropoxycarbonylpropylidene, 2-propoxycarbonylisopropylidene, 4-butoxycarbonylbutylidene, 5-pentyloxycarbonylpentylidene, 6-hexyloxycarbonylhexylidene, and the like.

The "5- or 6-membered, saturated or unsaturated heterocyclic ring which is formed by binding the groups of $R^8$ and $R^9$ together with the nitrogen atom to which they bind and may be intervened or not with nitrogen or oxygen atom" includes, for example, pyrrolidinyl, piperidinyl, piperazinyl, morpholino, pyrrolyl, imidazolyl, 1,2,4-triazolyl, 1,3,4-triazolyl, pyrazolyl, 2-pyrrolyl, 2-imidazolynyl, imidazolydinyl, 2-pyrazolynyl, pyrazolydinyl, 1,2-dihydropyridyl, 1,2,3,4-tetrahydropyridyl, and the like.

The "above mentioned heterocyclic ring which is substituted by lower alkyl groups" includes the above mentioned heterocyclic rings being substitututed by 1 to 3 straight chain or branched chain alkyl groups having 1 to 6 carbon atoms, for example, 4-methylpiperazinyl, 3,4-dimethylpiperazinyl, 3-ethylpyrrodinyl, 2-propylpyrrolidinyl, 3,4,5-trimethylpiperidinyl, 4-butylpiperidinyl, 3-pentylmorpholino, 4-hexylpiperazinyl, 2-methylimidazolyl, 3-methyl-1,2,4-triazolyl, 3-methylpyrrolyl, 3-methylpyrazolyl, 4-methyl-1,2-dihydropyridyl, and the like.

The "amino acid residue" includes, for example, alanyl, β-alanyl, arginyl, cistathionyl, cystyl, glycyl, histidyl, homoseryl, isoleucyl, lanthionyl, leucyl, lysyl, methionyl, norleucyl, norvalyl, ornithyl, prolyl, sarcosyl, celyl, threonyl, thyronyl, tyrosyl, valyl, α-aspartyl, β-aspartyl, aspartoyl, asparaginyl, α-glutamyl, γ-glutamyl, glutaminyl, cysteinyl, homocysteinyl, tryptophyl, dimethylglycyl, and the like.

The "amino-lower alkoxyl which may optionally be substituted by a group selected from a lower alkyl and a lower alkanoyl" includes a straight chain or branched chain alkoxy group having 1 to 6 carbon atoms which is substituted by an amino group optionally having 1 to 2 substituents selected from a straight chain or branched chain alkyl group having 1 to 6 carbon atoms and a straight chain or branched chain alkanoyl group having 1 to 6 carbon atoms, for example, aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, acetylaminomethoxy, 1-acetylaminoethoxy, 2-propionylaminoethoxy, 3-isopropionylaminopropoxy, 4-butyrylaminobutoxy, 5-pentanoylaminopentyloxy, 6-hexanoylaminohexyloxy, formylaminomethoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, (N-ethyl-N-propylamino)methoxy, 2-(N-methyl-N-hexylamino)ethoxy, and the like.

The "lower alkoxycarbonyl-substituted lower alkoxy" includes a straight chain or branched chain alkoxy group having 1 to 6 carbon atoms which is substituted by a straight chain or branched chain alkoxycarbonyl group having 1 to 6 carbon atoms, for example, methoxycarbonylmethoxy, 3-methoxycarbonylpropoxy, ethoxycarbonylmethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy, and the like.

The "carboxy-substituted lower alkoxy" includes a carboxyalkoxy group wherein the alkoxy moiety is a straight chain or branched chain alkoxy group having 1 to 6 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, and the like.

The "piperidinyl which may optionally be substituted by a phenyl-lower alkyl on the piperidine ring" includes a piperidinyl group which may optionally be substituted by a phenylalkyl group on the piperidine ring wherein the alkyl moiety is a straight chain or branched chain alkyl group having 1 to 6 carbon atoms, for example, piperidinyl, 1-benzyl-4-piperidinyl, 1-(2-phenylethyl)-3-piperidinyl, 1-(1-phenylethyl)-2-piperidinyl, 1-(3-phenylpropyl)-4-piperidinyl, 1-(4-phenylbutyl)-4-piperidinyl, 1-(5-phenylpentyl)-4-piperidinyl, 1-(6-phenylhexyl)-4-piperidinyl, 1-(1,1-dimethyl-2-phenylethyl)-3-piperidinyl, 1-(2-methyl-3-phenylpropyl)-2-piperidinyl, and the like.

The "carbamoyl-lower alkyl" includes a carbamoylalkyl group wherein the alkyl moiety is a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,1-dimethyl-2-carbamoylethyl, 2-methyl-3-carbamoylpropyl, and the like.

The "lower alkanoyl" includes a straight chain or branched chain alkanoyl group having 1 to 6 carbom atoms, for example, formyl, acetyl, propionyl, butyryl, isobutyryl, pentanoyl, tert-butylcarbonyl, hexanoyl, and the like.

The "amino which may optionally be substituted by a group selected from a lower alkyl and a lower alkanoyl" includes an amino group optionally being substituted by 1 to 2 groups selected from a straight chain or branched chain alkyl having 1 to 6 carbon atoms and a straight chain or branched chain alkanoyl having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, and the like.

The "lower alkoxycarbonyl-substituted lower alkyl" includes a straight chain or branched chain akyl group having 1 to 6 carbon atoms which is substituted by a straight chain or branched chain alkoxycarbonyl having 1 to 6 carbon atoms, for example, methoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 2-pentyloxycarbonylethyl, hexyloxycarbonylmethyl, and the like.

The "carboxy-substituted lower alkyl" includes a straight chain or branched chain alkyl group having 1 to 6 carbon atoms which is substituted by a carboxy, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "piperidinyl optionally having a lower alkyl substituent on the piperidine ring" includes a piperidinyl group optionally being substituted by a straight chain or branched chain alkyl having 1 to 6 carbon atoms on the piperidine ring, for example, piperidinyl, 1-methyl-4-piperidinyl, 1-ethyl-3-piperidinyl, 1-propyl-2-piperidinyl, 1-butyl-4-piperidinyl, 1-pentyl-4-piperidinyl, 1-hexyl-4-piperidinyl, and the like.

The "pyrrolidinylcarbonyl-lower alkoxy having a lower alkoxycarbonyl on the pyrrolidine ring" includes a pyrrolidinylcarbonylalkoxy group wherein the alkoxy moiety is a straight chain or branched chain alkoxy having 1 to 6 carbon atoms, and which is substituted by a straight chain or branched chain alkoxycarbonyl having 1 to 6 carbon atoms on the pyrrolidine ring, for example, 2-methoxycarbonyl-1-pyrrolidinylcarbonylmethoxy, 1-(2-ethoxycarbonyl-1-pyrrolidinylcarbonyl)ethoxy, 2-(3-propoxycarbonyl-1-pyrrolidinylcarbonyl)ethoxy, 3-(2-butoxycarbonyl-1-pyrrolidinylcarbonyl)propoxy, 4-(3-pentyloxycarbonyl-1-pyrrolidinylcarbonyl)butoxy, 5-(2-hexyloxycarbonyl-1-pyrrolidinylcarbonyl)pentyloxy, 6-(2-methoxycarbonyl-1-pyrrolidinylcarbonyl)hexyloxy, and the like.

The "lower alkoxycarbonyl" includes a straight chain or branched chain alkoxycarbonyl group having 1 to 6 carbon atoms, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

The "lower alkoxy-substituted lower alkanoyloxy" includes a straight chain or branched chain alkanoyloxy having 2 to 6 carbon atoms which is substituted by a straight chain or branched chain alkoxy having 1 to 6 carbon atoms, for example, methoxyacetyloxy, 3-ethoxypropionyloxy, 2-propoxypropionyloxy, 4-butoxybutyryloxy, 2,2-dimethyl-3-pentyloxypropionyloxy, 5-hexyloxypentanoyloxy, 6-methoxyhexanoyloxy, and the like.

The "amino which is optionally be substituted by a lower alkyl" includes an amino group optionally being substituted by 1 to 2 straight chain or branched chain alkyl groups having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The "amino-substituted lower alkylidene which is optionally be substituted by a lower alkyl" includes an amino substituted sfraight chain or branched chain alkylidene group having 1 to 6 carbon atoms wherein the amino moiety may optionally be substituted by 1 to 2 straight chain or branched chain alkyl groups having 1 to 6 carbon atoms, for example, aminomethylidene, 2-ethylaminoethylidene, 3-propylaminopropylidene, 2-isopropylaminopropylidene, 4-butylaminobutylidene, 5-pentylaminopentylidene, 6-hexylaminohexylidene, 3-dimethylaminopropylidene, 3-(N-methyl-N-butylamino)propylidene, 2-dipentylaminoethylidene, 4-(N-methyl-N-hexylamino)butylidene, and the like.

The "cyano-substituted lower alkyl" includes a cyanoalkyl group wherein the alkyl moiety is a straight chain or branched chain alkyl group having 1 to 6 carbon atoms, for example, cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl, and the like.

The "phthalimido-substituted alkyl" includes a phthalimido-substituted alkyl group wherein the alkyl moiety is a straight chain or branched chain alkyl group having 1 to 6 carbon atoms, for example, phthalimidomethyl, 2-phthalimidoethyl, 1-phthalimidoethyl, 3-phthalimidopropyl, 4-phthalimidobutyl, 5-phthalimidopentyl, 6-phthalimidohexyl, 1,1-dimethyl-2-phthalimidoethyl, 2-methyl-3-phthalimidopropyl, and the like.

The "lower alkoxy group having a substituent selected from hydroxy group and a phenylsulfonyloxy group optionally being substituted by a lower alkyl group on the phenyl ring" includes a straight chain or branched chain alkoxy group having 1 to 6 carbon atoms which is substituted by 1 to 3 groups selected from hydroxy group and a phenylsulfonyloxy group optionally being substituted by 1 to 3 alkyl groups having 1 to 6 carbon atoms on the phenyl ring, for example, (2-methylphenylsulfonyloxy)methoxy, 2-(4-methylphenylsulfonyloxy)ethoxy, 3-(phenylsulfonyloxy)propoxy, 4-(3-methylphenylsulfonyloxy)butoxy, 5-(2-ethylphenylsulfonyloxy)pentyloxy, 6-(3-propylphenylsulfonyloxy)hexyloxy, (4-butylphenylsulfonyloxy)methoxy, 2-(2-pentylphenylsulfonyloxy)ethoxy, 1-(3-hexylphenylsulfonyloxy)ethoxy, 3-(3,4-dimethylphenylsulfonyloxy)propoxy, 2-(3,4,5-trimethylphenylsulfonyloxy)ethoxy, hydroxymethoxy, 2-hydroxyethoxy, 1-hydroxyethoxy, 3-hyroxypropoxy, 2,3-dihydropropoxy, 4-hydroxybutoxy, 3,4-dihydroxybutoxy, 1,1-dimethyl-2-hydroxyethoxy, s-hydroxypentyloxy, 6-hydroxyhexyloxy, 2-methyl-3-hydroxypropoxy, 2,3,4-trihydroxybutoxy, and the like.

The "phenylsulfonyloxy-substituted lower alkyl which may optionally be substituted by a lower alkyl on the phenyl ring" includes a phenylsulfonyloxy-substituted straight chain or branched chain alkyl group having 1 to 6 carbon atoms wherein the phenylsulfonyloxy moiety may optionally be substituted by 1 to 3 straight chain or branched chain alkyl groups having 1 to 6 carbon atoms on the phenyl ring, for example, (2-methylphenylsulfonyloxy)methyl, 2-(4-methylphenylsulfonyloxy)ethyl, 3-(phenylsulfonyloxy)propyl, 4-(3-methylphenylsulfonyloxy)butyl, 5-(2-ethylphenylsulfonyloxy)pentyl, 6-(3-propylphenylsulfonyloxy)hexyl, (4-butylphenylsulfonyloxy)methyl, 2-(2-pentylphenylsulfonyloxy)ethyl, 1-(3-hexylphenylsulfonyloxy)ethyl, 3-(3,4-dimethylphenylsulfonyloxy)propyl, 2-(3,4,5-trimethylphenylsulfonyloxy)ethyl, and the like.

The "5- or 6-membered, saturated heterocyclic ring which is formed by binding $R^{11}$ and $R^{12}$ or $R^{29}$ and $R^{30}$ together with the nitrogen atom to which they bind and may be intervened or not with nitrogen or oxygen atom" includes, for example, pyrrolidinyl, piperidinyl, piperazinyl, morpholino, and the like.

The "above mentioned heterocyclic group which is substituted by a lower alkyl, a lower alkoxycarbonyl or an amino group optionally having substituents selected from a lower alkyl and a lower alkanoyl" includes the above mentioned heterocyclic groups having 1 to 3 substituents selected from a straight chain or branched chain alkyl having 1 to 6 carbon atoms, a straight chain or branched chain alkoxycarbonyl having 1 to 6 carbon atoms, and an amino group optionally being substituted by 1 to 2 groups selected from a straight chain or branched chain alkyl group having 1 to 6 carbon atoms and a straight chain or branched chain alkanoyl groups having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-tert-butoxycarbonylpiperazinyl, 4-ethoxycarbonylpiperidinyl, 2-methoxycarbonylpyrrolidinyl, 3-pentyloxycarbonylmorpholino, 4-hexyloxycarbonylpiperazinyl, 4-acetylaminopiperidinyl, 4-dimethylaminopiperidinyl, 3-methylaminomorpholino, 2-aminopyrrolidinyl, 3-(N-methyl-N-hexylamino)piperazinyl, 4-(N-methyl-N-acetylamino)piperidinyl, and the like.

The "above mentioned heterocyclic group which is substituted by a lower alkyl, a lower alkanoyl or an amino optionally being substituted by a lower alkyl" includes the above mentioned heterocyclic having 1 to 3 substituents selected from a straight chain or branched chain alkyl having 1 to 6 carbon atoms, a straight chain or branched chain alkanoyl having 1 to 6 carbon atoms, or an amino group optionally being substituted by 1 to 2 straight chain or branched chain alkyl having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-acetylpiperazinyl, 4-hexanoylpiperidinyl, 4-formylpiperidinyl, 2-propionylpyrrolidinyl, 3-butyrylmorpholino, 4-pentanoylpiperazinyl, 4-ethylaminopiperidinyl, 4-dimethylaminopiperidinyl, 3-methyl-4-acetylpiperazinyl, 3-methylaminomorpholino, 2-aminopyrrolidinyl, 3-(N-methyl-N-hexylamino)piperazinyl, 4-(N-methyl-N-butylamino)piperidinyl, and the like.

The "5- or 10-membered, saturated or unsaturated heteromonocyclic ring or heterobicyclic ring which is formed by binding $R^{27}$ and $R^{28}$ together with the nitrogen atom to which they bind and may be intervened or not with nitrogen or oxygen atom" includes, for example, pyrrolidinyl, piperidinyl, piperazinyl, morpholino, imidazolyl, isoindolyl, 1,2,3,4,5,6,7-octahydroisoindolyl, and the like.

The "above mentioned heterocyclic group which is substituted by oxo group, a lower alkyl, a lower alkoxycarbonyl or a lower alkanoyl" includes the above mentioned heterocyclic groups having 1 to 3 substituents selected from oxo group, a straight chain or branched chain alkyl having 1 to 6 carbon atoms, a straight chain or branched chain alkoxycarbonyl having 1 to 6 carbon atoms, and a straight chain or branched chain alkanoyl having 1 to 6 carbon atoms, for example, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 2-methylmorpholino, 4-formylpiperidinyl, 4-acetylpiperazinyl, 2-propanoylmorpholino, 3-butyrylmorpholino, 3-pentanoylpyrrolidinyl, 4-hexanoylpiperidinyl, 3-methyl-4-acetylpiperazinyl, 3-methylimidazolyl, 2-acetylimidazolyl, 4-tert-butoxycarbonylpiperazinyl, 4-ethoxycarbonylpiperidinyl, 2-methoxycarbonylpyrrolidinyl, 3-pentyloxycarbonylmorpholino, 4-hexyloxycarbonylpiperazinyl, 3-tert-butoxycarbonylimidazolyl, 1,3-dioxo-1,2,3,4,5,6,7-octahydroisoindolyl, and the like.

The "cyano-substituted lower alkylidene" includes a straight chain or branched chain alkylidine group having 1 to 6 carbon atoms which is substituted by cyano group, for example, cyanomethylidene, 2-cyanoetylidene, 3-cyanopropylidene, 2-cyanopropylidene, 4- cyanobutylidene, 5-cyanopentylidene, 6-cyanohexylidene, and the like.

The "piperazinyl-lower alkoxy having a lower alkanoyl at the 4-position of the piperazine ring" includes a straight chain or branched chain alkoxy group having 1 to 6 carbon atoms which is substituted by a peperazinyl being substituted by a straight chain or branched chain alkanoyl having 1 to 6 carbon atoms on the 4-position of the piperazine ring, for example, 3-(4-acetyl-1-piperazinyl)propoxy, 2-(4-acetyl-1-piperazinyl)ethoxy, (4-acetyl-1-piperazinyl)methoxy, 1-(4-propionyl-1-piperazinyl)ethoxy, 4-(4-butyryl-1-piperazinyl)butoxy, 5-(4-pentanoyl-1-piperazinyl)pentyloxy, 6-(4-hexanoyl-1-piperazinyl)hexyloxy, 3-(4-formyl-1-piperazinyl)-propoxy, and the like.

The benzoheterocyclic compounds of the present invention can be prepared by various processes, for example, by the processes shown in the following reaction schemes.

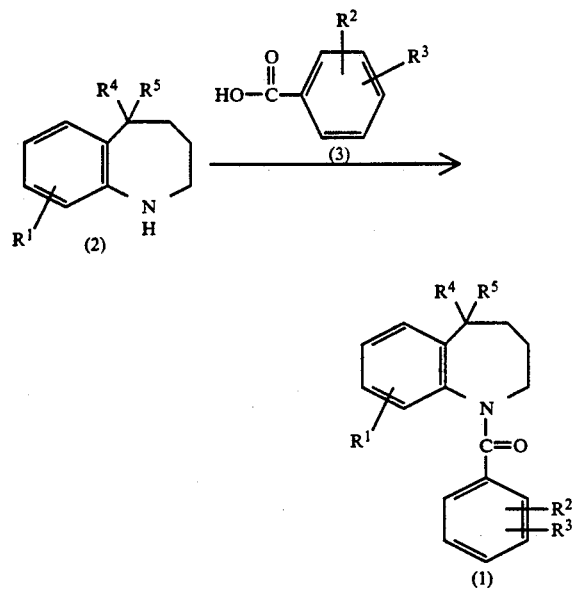

[wherein $R^1$, $R^2$, $R^3$, $R^4$ and $R^5$ are the same as defined above]

The process of Reaction Scheme-1 is carried out by reacting a benzoheterocyclic compound of the formula (2) and a carboxylic acid of the formula (3) by a conventional amido bond producing reaction. The amido bond producing reaction can be carried out under the conditions for the conventional amido bond producing reaction, for example, (i) a mixed acid anhydride process, i.e. a process of reacting a carboxylic acid (3) with an alkylhalocarboxylic acid to form a mixed acid anhydride and reacting the resultant with an amine compound (2);

(ii) an acitivated ester process, i.e. a process of converting a carboxylic acid (3) into an activated ester such as p-nitrophenyl ester, N-hydroxysuccinimide ester and 1-hydroxybenzotriazole ester, etc., and reacting the resultant with an amine compound (2);

(iii) a carbodiimide process, i.e. a process of condensing a carboxylic acid (3) and an amine compound (2) in the presence of an activating agent such as dicyclohexylcarbodiimide, carbonyldiimidazole, etc.;

(iv) other processes, i.e. a process of converting a carboxylic acid (3) into a carboxylic anhydride by treating it with a dehydrating agent such as acetic anhydride, and reacting the resultant with an amine compound (2); a process of reacting an ester of a carboxylic acid (3) with a lower alcohol and an amine compound (2) at a high temperature under high pressure; a process of reacting an acid halide compound of a carboxylic acid (3), e.g. a carboxylic acid halide, with an amine compound (2), and the like.

The mixed acid anhydride used in the above mixed acid anhydride process (i) is obtained by the known Schötten-Baumann reaction, and the reaction product is used without isolation from the reaction mixture for the reaction with the amine compound (2) to give the desired benzoheterocyclic compounds (1) of the present invention. The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo-[4.3.0]nonen-5 (DBN), 1,8-biazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at about −20° to about 100° C., preferably at about 0° to about 50° C., for about 5 minutes to about 10 hours, preferably for about 5 minutes to about two hours.

The reaction of thus obtained mixed acid anhydride with the amine compound (2) is usually carried out at about −20° to about 150° C., preferably at about 10° to about 50° C., for about 5 minutes to about 10 hours, preferably for about 5 minutes to about 5 hours. The mixed acid anhydride process is usually carried out in an appropriate solvent. The solvent is any conventional solvent used for the mixed acid anhydride process, and includes, for example, halogenated hydrocarbons (e.g. chloroform, dichloromethane, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, acetonitrile, hexamethylphosphoric acid triamide, etc.), or a mixture of these solvents. The alkylhalocarboxylic acid used in the mixed acid-anhydride process includes, for example, methyl chloroformate, methyl bromoformate, ethyl chloroformate, ethyl bromoformate, isobutyl chloroformate, and the like. In said process, the carboxylic acid (3), the alkylhalocarboxylic acid and the amine compound (2) are usually used in each equimolar amount, but the alkylhalocarboxylic acid and the carboxylic acid (3) can be used each in an amount of about 1 to 1.5 mole to 1 mole of the amine compound (2).

Among the above other processes (iv), in case of the process of reacting the carboxylic acid halide with the amine compound (2), the reaction is usually carried out in the presence of a basic comopund in an appropriate solvent. The basic compound is any conventional basic compound, and includes, for example, in addition to the basic compounds used for the above mentioned Schötten-Baumann reaction, sodium hydroxide, potassium hydroxide, sodium hydride, potassium hydride, and the like. The solvent includes, for example, in addition to the solvents used for the above mentioned mixed acid anhydride process, alcohols (e.g. methanol, ethanol, propanol, butanol, 3-methoxy-1-butanol, ethylcellosolve, methylcellosolve, etc.), pyridine, acetone, water, and the like. The amount of the amine compound (2) and the carboxylic acid halide is not critical, but the carboxylic acid halide is usually used at least in equimolar amount, preferably about 1 to 5 moles to 1 mole of the amine compound (2). The reaction is usually carried out at about −20° to about 180° C., preferably at about 0° to about 150° C., for about 5 minutes to about 30 hours.

The amido bond producing reaction of Reaction Scheme-1 may also be carried out by reacting the carboxylic acid compound (3) with the amine compound (2) in the presence of a condensing agent such as phosphorus compunds (e.g. triphenylphosphine, diphenylphosphinyl chloride, phenyl-N-phenylphosphoramide chloridate, diethyl chlorophosphate, diethyl cyanophosphate, diphenylphosphoric acid azide, bis(2-oxo-3-oxazolidinyl)phosphinic chloride, etc.).

The reaction is usually carried out in the presence of a solvent and a basic compound as used in the above reaction of the carboxylic acid halide and the amine compound (2) at about −20° to about 150° C., preferably at about 0° to about 100° C., for about 5 minutes to about 30 hours. The condensing agent and the carboxylic acid (3) are used in each equimolar ammount, preferably in an amount of 1 mole to 2 moles, to 1 mole of the amine compound (2).

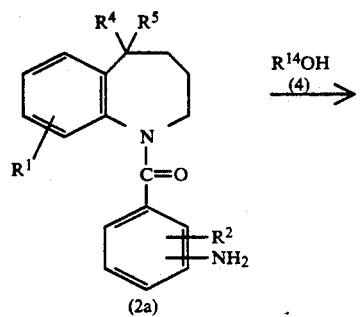

[wherein $R^1$, $R^2$, $R^4$ and $R^5$ are the same as defined above, and $R^{14}$ is a group of the formula:

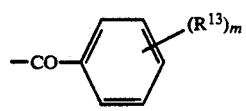

(wherein $R^{13}$ and m are the same as defined above), or a phenyl-lower alkanoyl group having 1 to 3 substituents on the phenyl ring selected from a halogen atom, a lower alkoxy group, a lower alkyl group and nitro group]

The reaction between the compound (2a) and the compound (4) can be carried out under the same conditions as in the reaction of the compound (2) and the compound (3) in Reaction Scheme-1.

[Reaction Scheme-3]

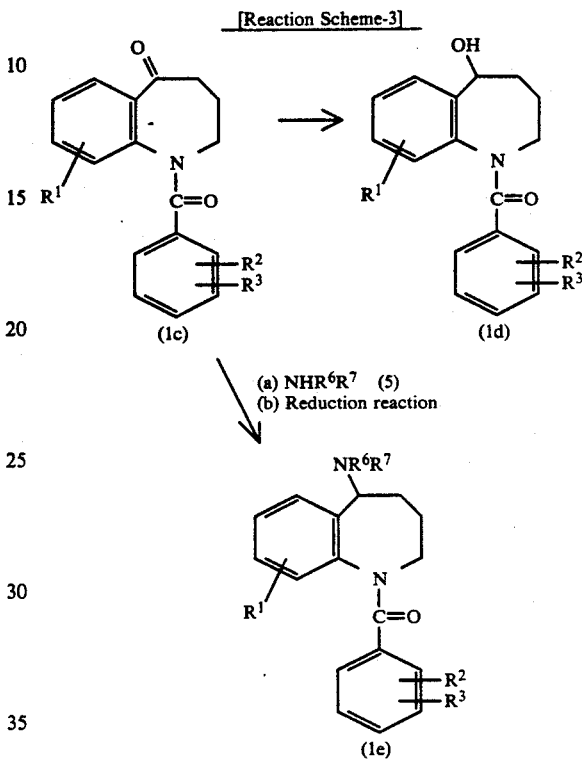

[wherein $R^1$, $R^2$, $R^3$, $R^6$ and $R^7$ are the same as defined above]

The reaction of converting the compound (1c) to the compound (1d) is carried out by reduction.

The above reduction reaction is preferably carried out by a process using an hydrogenation agent. The hydrogenation agent includes, for example, lithium aluminum hydride, lithium borohydride, sodium borohydride, diborane, and the like. The hydrogenation agent is used at least in equimolar amount, preferably in an amount of 1 mole to 15 moles, to 1 mole of the starting compound. The said reduction reaction is usually carried out in an appropriate solvent such as lower alcohols (e.g. water, methaonl, ethanol, isopropanol, etc.), ethers (e.g. tetrahydrofuran, diethyl ether, diisopropyl ether, diglyme, etc.), or a mixture of these solvents. . The reaction is usually carried out at about −60° to about 150° C., preferably at −30° to 100° C., for about 10 minutes to about 15 hours. When lithium aluminum hydride or diborane is used as a reducing agent, the non-aqueous solvent such as tetrahydrofuran, diethyl ether, diisopropyl ether, diglyme, etc. is preferable.

The process of converting the compound (1c) to the compound (1e) is usually carried out in an appropriate solvent or without solvent in the presence or absence of a dehydrating agent. The solvent includes, for example, alcohols (e.g. methanol, ethanol, isopropanol, etc.), aromatic hydrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylacetamide, N-methylpyrrolidone, etc.), or a mixture of these solvents. The dehydrating agent includes, for example, any conventional drying agent used for dehydration of solvent (e.g. molecular shieves, etc.), mineral acids (e.g. hydrochloric acid, sulfuric acid, boron trifluoride, etc.), organic acids (e.g. p-toluenesulfonic acid, etc.), and the like. The said reaction is usually carried out at a temperature of from room temperature to 250° C., preferably at about 50° to about 200° C., for about 1 to about 48 hours. The amount of the compound (5) is not critical, but the compound (5) is used at least in equimolar amount, preferably in an amount of 1 mole to large excess amount, to 1 mole of the compound (1c). When a drying agent is used as a dehydrating agent, it should be used in large excess amount, and when an acid is used as a dehydrating agent, it should be used in a catalytic amount.

The subsequent reduction reaction may be carried by various processes, and is carried out by catalytic hydrogenation with a catalyst in an appropriate solvent. The solvent includes, for example, water, acetic acid, alcohols (e.g. methanol, ethanol, isopropanol, etc.), hydrocarbons (e.g. hexane, cyclohexan, etc.), ethers (e.g. diethylene glycol dimethyl ether, dioxane, tetrahydrofuran, diethyl ether, etc.), esters (e.g. ethyl acetate, methyl acetate, etc.), aprotic polar solvents (e.g. dimethylformamide, etc.), or a mixture of these solvents. The catalyst includes, for example, palladium, palladium-black, palladium-carbon, platinum, platinum oxide, copper chromite, Raney nickel, and the like. The catalyst is usually used in an amount of 0.02 mole to 1 mole to 1 mole of the starting compound. The reduction is usually carried out at about −20° to about 100° C., preferably at about 0° to about 70° C., under 1 to 10 pressures of hydrogen gas, for about 0.5 to about 20 hours.

In addition to the above reduction reaction, the reduction using a hydrogenating agent is preferably used. The hydrogenation agent includes, for example, lithium aluminum hydride, sodium borohydride, diborane, and the like. The hydrogenation agent is usually used at least in equimolar amount, preferably in an amount of 1 mole to 10 moles, to 1 mole of the compound (1c). This reduction reaction is usually carried out in an appropriate solvent such as water, lower alcohols (e.g. methanol, ethanol, isopropanol, etc.), ethers (e.g. tetrahydrofuran, diethyl ether, diglyme, etc.), dimethylformamide, or a mixture of these solvents, at about −60° to 50° C., preferably at about −30° C. to room temperature, for about 10 minutes to about 5 hours. When lithium aluminum hydride or diborane is used as a reducing agent, anhydrous solvent such as diethyl ether, tetrahydrofuran, diglyme, etc. is preferable.

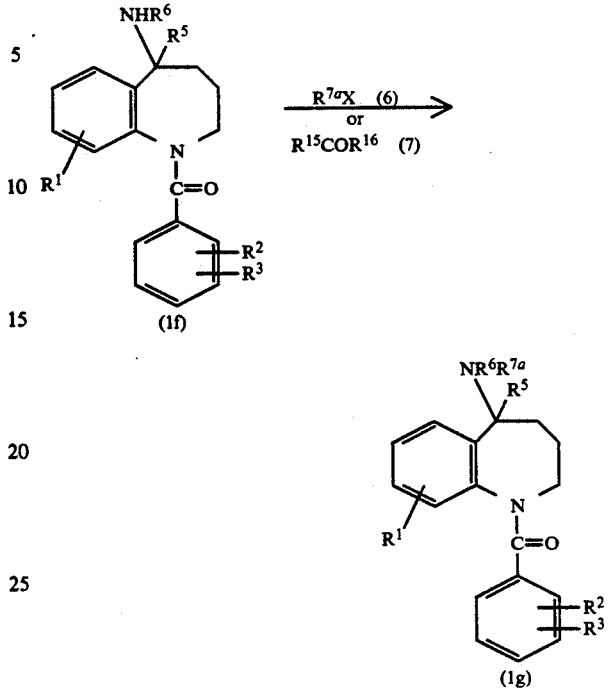

[wherein $R^1$, $R^2$, $R^3$, $R^5$ and $R^6$ are the same as defined above, $R^{7a}$ is a lower alkyl group or a lower alkenyl group, $R^{15}$ and $R^{16}$ are each hydrogen atom or a lower alkyl group, and X is a halogen atom]

The reaction between the compound (1f) and the compound (6) is usually carried out in an appropriate inert solvent in the presence or absence of a basic compound.

The inert solvent includes, for example, aromatic hydrocarbons (e.g. benzene, toluene, xylene, etc.), ethers (e.g. tetrahydrofuran, dioxane, diethylene glycol dimethyl ether, etc.), halogenated hydrocarbons (e.g. dichloromethane, chloroform, carbon tetrachloride, etc.), lower alcohols (e.g. methanol, ethanol, isopropanol, butanol, tert-butanol, etc.), acetic acid, ethyl acetate, acetone, acetonitril, pyridine, dimethylsulfoxide, dimethylformamide, hexamethylphophoric acid triamide, or a mixture of these solvents. The basic compound includes, for example, metal carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methylate, sodium ethylate, etc.), organic basic compounds (e.g. pyridine, N-ethyldiisopropylamine, dimethylaminopyridine, triethylamine, 1,5-diazabicyclo[4.3.0]nonen-5 (DBN), 1,8-diazabicyclo[5.4.0]undecene-7 (DBU), 1,4-diazabicyclo[2.2.2]octane (DABCO), etc.) and the like. The amount of the compound (1f) and the compound (6) is not critical, but the compound (6) is used at least in about equimolar amount, preferably in an amount of 1 mole to 10 moles, to 1 mole of the compound (1f). The reaction is usually carried out at about 0° to about 200° C., preferably at about 0° to about 170° C., for about 30 minutes to about 75 hours. An alkali metal halide (e.g. sodium iodide, potassium iodide, etc.) may be added to the reaction system.

The reaction between the compound (1f) and the compound (7) is carried out in an appropriate solvent or without solvent in the presence of a reducing agent. The solvent includes, for example, water, alcohols (e.g. methanol, ethanol, isopropanol, etc.), acetonitril, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, aliphatic acid alkali metal salts (e.g. sodium formate, etc.), hydrogenation agents (e.g. sodium borohydride, sodium cyano borohydride, lithium aluminum hydride, etc.), catalysts (e.g. palladium black, palladium-carbon, platinum oxide, platinum black, Raney nickel, etc.).

When formic acid is used as a reducing agent, the reaction is usually carried out at room temperature to about 200° C., preferably at about 50° to about 150° C., for about 1 to 10 hours. The formic acid is used in large excess amount to the amount of the compound (1f).

When a hydrogenation agent is used as a reducing agent, the reaction is usually carried out at about −30° to about 100° C., preferably at about 0° to about 70° C., for about 30 minutes to about 12 hours. The reducing agent is usually used in an amount of 1 mole to 20 moles, preferably in an amount of 1 mole to 6 moles, to 1 mole of the compound (1f). When lithium aluminum hydride is used as a reducing agent, ethers (e.g. diethyl ether, dioxane, tetrahydrofuran, diglyme, etc.) or aromatic hydrocarbons (e.g. benzene, toluene, xylene, etc.) is preferably used as a solvent.

When a catalyst is used, the reaction is usually carried out under atmospheric pressure to 20 atms., preferably under atmospheric pressure to 10 atms of hydrogen gas, or in the presence of a hydrogen donor such as formic acid, ammonium formate, cyclohexene, hydrazine hydrate, etc. at about −30° to about 100° C., preferably at about 0° to about 60° C., for 1 to 12 hours. The catalyst is usually used in a ratio of 0.1 to 40 % by weight, preferably in a ratio of about 1 to about 20 % by weight, to the amount of the compound (1f).

The compound (7) is usually used at least in equimolar amount, preferably in an amount of 1 mole to large excess amount to 1 mole of the compound (1f).

[Reaction Scheme-5]

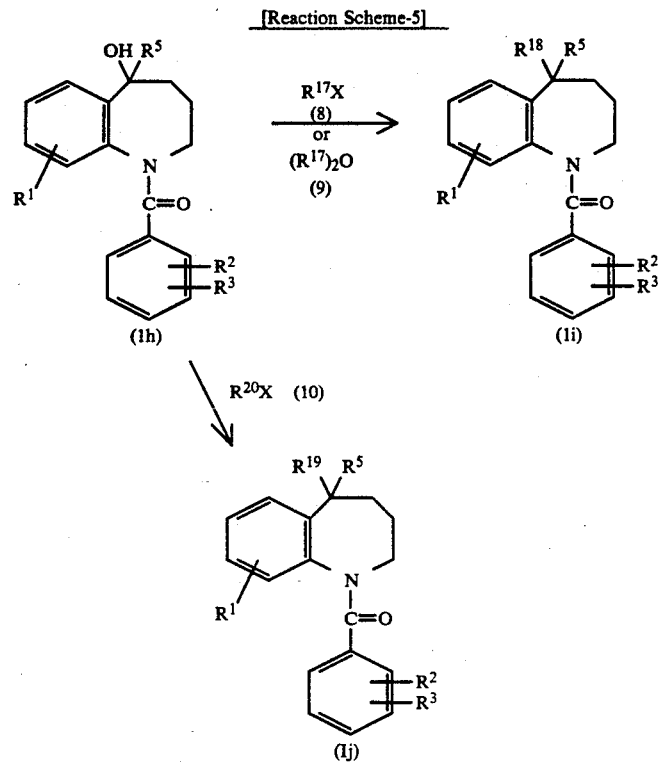

[wherein $R^1$, $R^2$, $R^3$, X and $R^5$ are the same as defined above, $R^{18}$ is a lower alkanoyloxy group having a halogen substituent, or a lower alkoxy-substituted lower alkanoyloxy group, $R^{19}$ is a lower alkenyloxy group, a group of the formula: $-O-CO-A-NR^8R^9$ (wherein A, $R^8$ and $R^9$ are the same as defined above), a group of the formula:

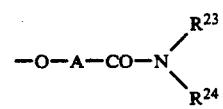

(wherein A, $R^{23}$ and $R^{24}$ are the same as defined above), a pyrrolidinylcarbonyl-lower alkoxy group having a lower alkoxycarbonyl on the pyrrolidine ring, a group of the formula:

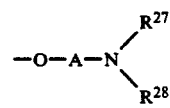

(wherein A, $R^{27}$ and $R^{28}$ are the same as defined above), or a lower alkoxy group having a substituent selected from hydroxy group and a phenylsulfonyloxy group optionally being substituted by a lower alkyl group on the phenyl ring, $R^{20}$ is a lower alkenyl group, a group of the formula: —CO—A—NR⁸R⁹ (wherein A, R⁸, R⁹ are the same as defined above), a group of the formula:

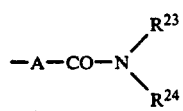

(wherein A, $R^{23}$ and $R^{24}$ are the same as defined above), a pyrrolidinylcarbonyl-lower alkyl group having a lower alkoxycarbonyl group on the pyrrolidine ring, a group of the formula

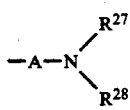

(wherein A, $R^{27}$ and $R^{28}$ are the same as defined above), or a lower alkyl group having a substituent selected from hydroxy group and a phenylsulfonyloxy group optionally being substituted by a lower alkyl group on the phenyl ring, $R^{17}$ is a lower alkanoyl group having a halogen substituent, or a lower alkoxy-substituted lower alkanoyl group]

The reaction between the compound (1h) and the compound (8) or the compound (9) is carried out under the same conditions as in the reaction between the compound (1f) and the compound (6) in above mentioned Reaction Scheme-4.

The reaction between the compound (1h) and the compound (10) is carried out under the same conditions as in the reaction between the compound (1f) and the compound (6) in above mentioned Reaction Scheme-4.

When the compound (1i) is a compound of the formula (1i) wherein $R^{18}$ is a lower alkanoyl group having a halogen substituent, the said compound (1i) can be reacted with a compound of the formula (11): HNR⁸R⁹ (wherein R⁸ and R⁹ are the same as defined above) under the same conditions as in the reaction between the compound (1f) and the compound (6) in above mentioned Reaction Scheme-4 to give the compound of the formula (1j) wherein $R^{19}$ is a group of the formula: —O—CO—A—NR⁸R⁹ (wherein A, R⁸ and R⁹ are the same as defined above).

[Reaction Scheme-6]

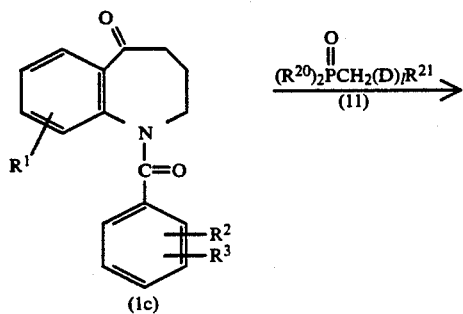

-continued
[Reaction Scheme-6]

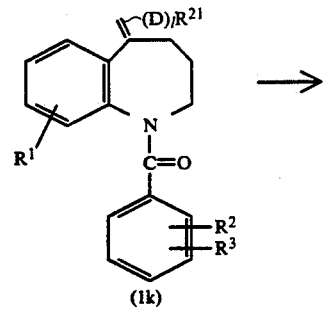

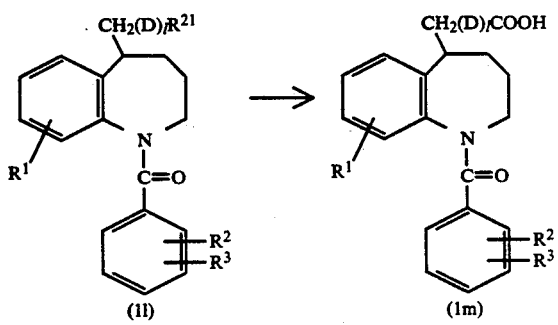

[wherein $R^1$, $R^2$ and $R^3$ are the same as defined above, $R^{20}$ is a lower alkoxy group, $R^{21}$ is a lower alkoxycarbonyl group, cyano group or an amino group optionally being substituted by a lower alkyl group, D is a lower alkylene group and l is an integer of 0 or 1]

The reaction between the compound (1c) and the compound (11) is carried out in an appropriate solvent in the presence of a basic compound. The basic compound includes, for example, inorganic basic compounds (e.g. metal sodium, metal potassium, sodium hydride, sodium amide, sodium hydoxide, potassium hydroxide, sodium carbonate, potassium carbonate, sodium hydrogen carbonate, etc.), metal alcoholates (e.g. sodium methylate, sodium ethylate, potassium tert-butoxide, etc.), alkyl lithium, aryl lithium or lithium amide (e.g. methyl lithium, n-butyl lithium, phenyl lithium, lithium diisopropylamide, etc.), organic basic compounds (e.g. pyridine, piperidine, quinoline, triethylamine, N,N-dimethylaniline, etc.), and the like. The solvent may be any solvent which does not cause any trouble to the reaction, and includes, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-diemethylformamide, dimethylsulfoxide, hexamethylphosphoric acid triamide, etc.), alcohols (e.g. methanol, ethanol, isopropanol, etc.), and the like. The reaction is usually carried out at −80° to 150° C., preferably at about −80° to about 120° C., for about 0.5 to 15 hours.

The reaction of converting the compound (1k) into the compound (1l) is carried out under the same reduction conditions as in the reaction of converting the compound (1c) into the compound (1e) in above mentioned Reaction Scheme-3. When a hydrogenation agent is used in said reduction reaction, the addition of methal halide (e.g. nickel chloride, etc.) into the reaction system advantageously promotes the reaction.

When the compound (11) is a compound of the formula (11) wherein $R^{21}$ is a lower alkoxycarbonyl group, the reaction of converting the compound (11) into the compound (1m) is carried out in an appropriate solvent or without solvent in the presence of an acid or a basic compound. The solvent includes, for example, water, lower alcohols (e.g. methanol, ethanol, isopropanol, etc.), ketons (e.g. acetone, methylethylketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.), and the like. The basic compound includes, for example, metal carbonates (e.g. sodium carbonate, potassium carbonate, etc.), metal hydroxides (e.g. sodium hydroxide, potassium hydroxide, calcium hydroxide, etc.), and the like. The reaction is usually carried out at room temperature to about 200° C., preferably at room temperature to about 150° C., for about 10 minutes to about 25 hours.

[Reaction Scheme-7]

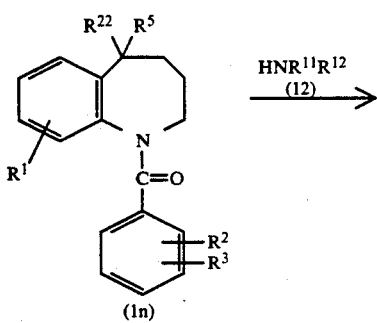

(1n)

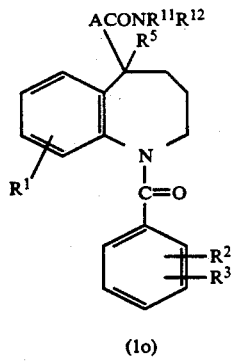

(1o)

[wherein $R^1$, $R^2$, $R^3$, $R^5$, $R^{11}$, $R^{12}$ and A are the same as defined above, and $R^{22}$ is a carboxy-substituted lower alkyl group]

The reaction between the compound (1n) and the compound (12) is carried out under the same conditions as in the reaction between the compound (2) and the compound (3) in above mentioned Reaction Scheme-1.

[Reaction Scheme-8]

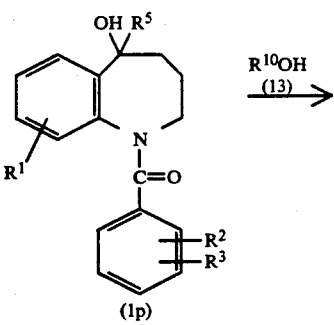

(1p)

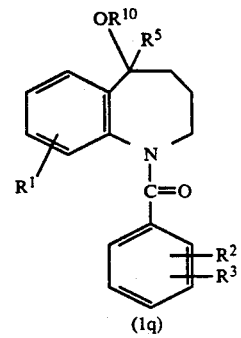

(1q)

[wherein $R^1$, $R^2$, $R^3$, $R^5$ and $R^{10}$ are the same as defined above]

The reaction between the compound (1p) and the compound (13) is carried out in an appropriate solvent in the presence of a basic compound. To the reaction system, it may be preferable to add a condensing agent such as dicyclohexylcarbodiimide, carbonyldiimidazole, 1-ethyl-3-(3'-dimethylaminopropyl)carbodiimide, and the like. The basic compound and the solvent used therein are the same as those for the reaction between the compound (1f) and the compound (6) in above mentioned Reaction Scheme-4. The compound (13) is used at least in equimolar amount, preferably in an amount of 1 mole to 2 moles, to 1 mole of the compound (1p). The reaction is usually carried out at 0° to 100° C., preferably at about 0° to about 70° C., for about 1 to about 15 hours.

Alternatively, the reaction may proceed as follows. That is, before reacting with the compound (1p), the amino acid residue for $R^{10}$ of the compound (13) may be protected by a conventional protecting group for amino acid such as phenyl-lower alkoxycarbonyl groups (e.g. benzyloxycarbonyl, etc.) and lower alkoxycarbonyl groups (e.g. tert-butoxycarbonyl, etc.), which is removed thereafter by a conventional deprotecting reaction such as catalytic reduction, hydrolysis, and the like, and further the resultant may be converted into the compound (1q).

[Reaction Scheme-9]

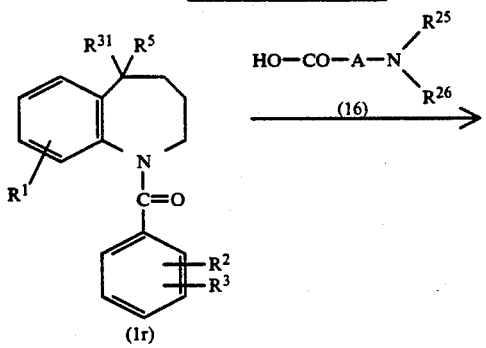
(1r)

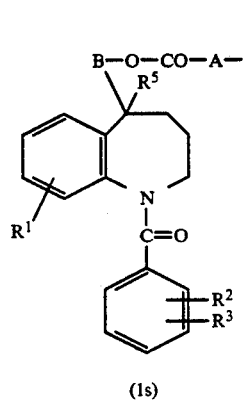
(1s)

[wherein $R^1$, $R^2$, $R^3$, $R^5$, $R^{25}$, $R^{26}$, A and B are the same as defined above, and $R^{31}$ is hydroxy-substituted lower alkyl group]

The reaction between the compound (1r) and the compound (16) is carried out under the same conditions as in the reaction between the compound (1p) and the compound (13) in above mentioned Reaction Scheme-8.

-continued
[Reaction Scheme-10]

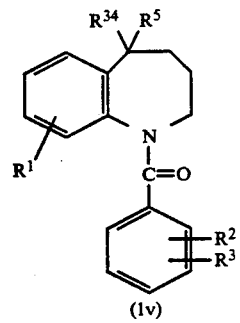
(1v)

[wherein $R^1$, $R^2$, $R^3$, $R^5$, $R^{29}$, $R^{30}$, $R^{31}$ and X are the same as defined above, $R^{32}$ is a phenysulfonyl group optionally having a lower alkyl substituent on the phenyl ring, $R^{33}$ is a phenylsulfonyloxy-substituted lower alkyl group optionally having a lower alkyl substituent on the phenyl ring, $R^{34}$ is a group of the formula

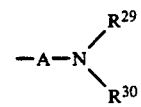

(wherein A, $R^{29}$ and $R^{30}$ are the same as defined above)]

The reaction between the compound (1t) and the compound (17) is carried out under the same conditions as in the reaction between the compound (1f) and the compound (6) in above mentioned Reaction Scheme-4.

The reaction between the compound (1u) and the compound (18) is carried out under the same conditions as in the reaction between the compound (1f) and the compound (6) in above mentioned Reaction Scheme-4.

[Reaction Scheme-10]

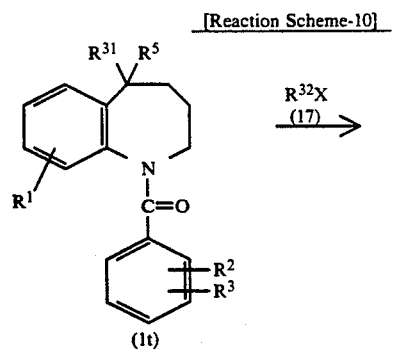
(1t)

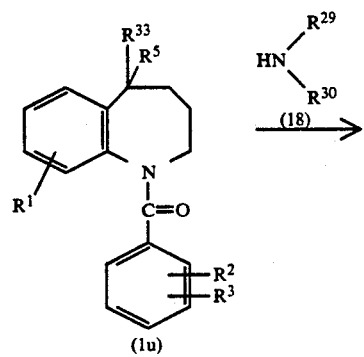
(1u)

[Reaction Scheme-11]

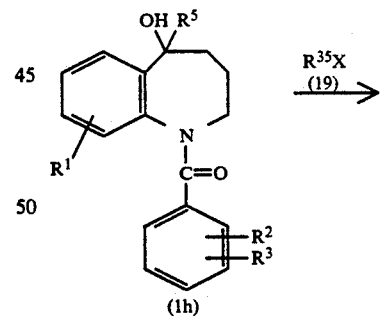
(1h)

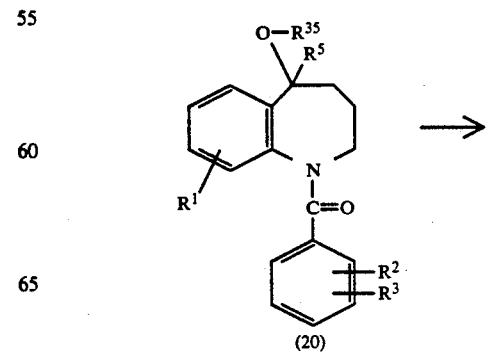
(20)

-continued
[Reaction Scheme-11]

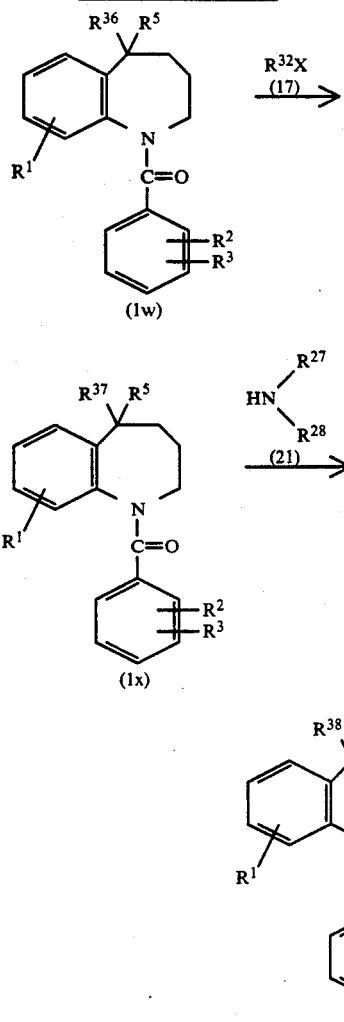

[wherein R¹, R², R³, R⁵, R²⁷, R²⁸ and R³² are the same as defined above, R³⁶ is a lower alkoxy group substituted by hydroxy group, R³⁷ is a lower alkoxy group which is substituted by a phenylsulfonyloxy group optionally being substituted by a lower alkyl group on the phenyl ring, and R³⁸ is a group of the formula:

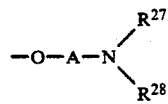

(wherein R²⁷, R²⁸ and A are the same as defined above)]

The reaction between the compound (1h) and the compound (19) is carried out under the same conditions as in the reaction between the compound (1f) and the compound (6) in above mentioned Reaction Scheme-4.

The reaction of converting the compound (20) into the compound (1w) is carried out under the same conditions as in the reduction reaction of the compound (1c) into the compound (1d) in above mentioned Reaction Scheme-3.

The reaction between the compound (1w) and the compound (17) is carried out under the same conditions as in the reaction between the compound (1f) and the compound (6) in above mentioned Reaction Scheme-4.

The reaction between the compound (1x) and the compound (21) is carried out under the same conditions as in the reaction between the compound (1f) and the compound (6) in above mentioned Reaction Scheme-4.

The starting compound (2a) may be prepared by the following processes.

[Reaction Scheme-12]

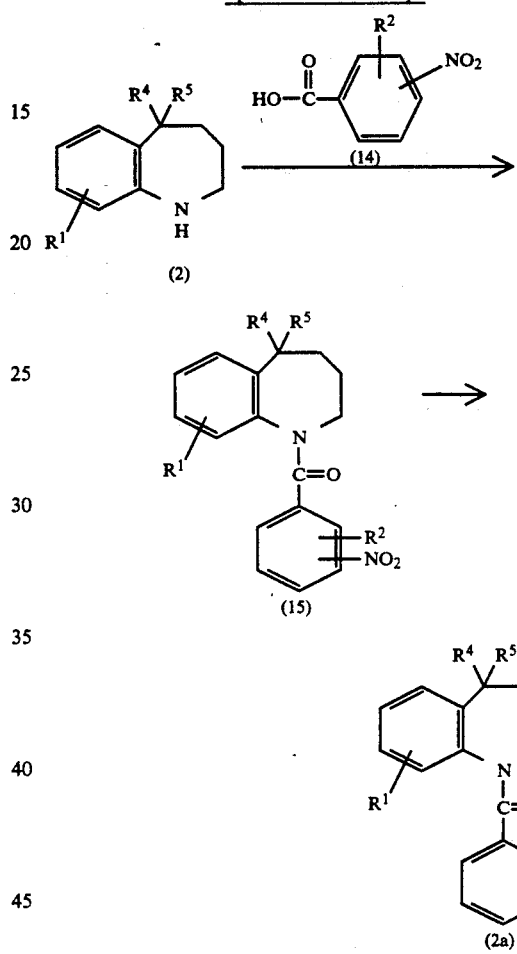

[wherein R¹, R², R⁴ and R⁵ are the same as defined above]

The reaction between the compound (2) and the compound (14) is carried out under the same conditions as in the reaction between the compound (2) and the compound (3) in above mentioned Reaction Scheme-1.

The reaction of converting the compound (15) to the compound (2a) is carried out by (A) reduction reaction using a catalyst in an appropriate solvent; or (B) reduction reaction using a combination of metal or metal salt and an acid, or a combination of metal or metal salt and an alkali metal hydroxide, sulfite or ammonium salt, and the like, as a reducing agent in an inert solvent.

When the process (A) is employed, the solvent includes, for example, water, acetic acid, alcohols (e.g. methanol, ethanol, isopropanol, etc.), hydrocarbons (e.g. hexane, cyclohexane, etc.),-ethers (e.g. dioxane, tetrahydrofuran, diethyl ether, diethylene glycol dimethyl ether, etc.), esters (e.g. ethyl acetate, methyl acetate, etc.), aprotic polar solvents (e.g. N,N-dimethylformamide, etc.), or a mixture of these solvents. The catalyst includes, for example, palladium, palladium-black, palladium-carbon, platinum, platinum oxide, copper chromite, Raney nickel, and the like. The catalyst is usually used in an amount of about 0.02 to about 1 mole, to 1 mole of the starting compound. The reaction is usually carried out at about −20° to about 150° C., preferably at about 0° to about 100° C., under 1 to 10 pressures of hydrogen gas, for about 0.5 to about 10 hours. An acid such as hydrochloric acid, etc. may be added to the reaction system.

When the process (B) is employed, there is used as a reducing agent a combination of iron, zinc, tin or stannous chloride and a mineral acid (e.g. hydrochloric acid, sulfuric acid, etc.), or a combination of iron, iron sulfate, zinc or tin and an alkali metal hydroxide (e.g. sodium hydroxide, etc.), a sulfide (e.g. ammonium sulfide, etc.) or an ammonium salt (e.g. aqueous ammonia, ammonium chloride, etc.). The inert solvent includes, for example, water, acetic acid, methanol, ethanol, dioxane, and the like. The conditions for the above reduction reaction are chosen according to the kinds of the reducing agent used therein, for example, when stannous chloride and hydrochloric acid are used, the reaction advantageously proceeds at about 0° C. to room temperature for about 0.5 to 10 hours. The reducing agent is used at least in equimolar amount, usually in an amount of 1 mole to 5 moles, to 1 mole of the staring compound.

The compound (1) wherein $R^1$ is hydroxy group can be obtained by dealkylation of the compound (1) wherein $R^1$ is a lower alkoxy group. The said dealkylation reaction is carried out by heat-treatment in a mixture of an acid (e.g. hydrobromic acid, hydrochloric acid, etc.) and a solvent (e.g. water, methanol, ethanol, isopropyl alcohol, etc.) at 30° to 150° C., preferably at 50° to 120° C., or by hydrolysis. The hydrolysis is carried out in an appropriate solvent in the presence of an acid. The solvent includes, for example, water, lower alcohols (e.g. methanol, ethanol, isopropanol, etc.), ethers (e.g. dioxane, tetrahydrofuran, etc.), halogenated hydrocarbons (e.g. dichloromethane, chloroform, carbon tetrachloride, etc.), polar solvents (e.g. acetonitrile, etc.), or a mixture of these solvents. The acid includes, for example, mineral acids (e.g. hydrochloric acid, sulfuric acid, hydrobromic acid, etc.), Lewis acids (e.g. boron trifluoride, aluminum chloride, boron tribromide, etc.), iodides (e.g. sodium iodide, potassium iodide, etc.), a mixture of a iodide and a Lewis acid, and the like. The reaction is usually carried out at room temperature to 150° C., preferably at room temperature to 100° C., for about 0.5 to about 15 hours.

Among the active compounds (1) of the present invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of the present invention, the compounds having a basic group can be easily converted into acid addition salts thereof by treating with a pharmaceutically acceptable acid. The acid includes, for example, inorgainc acids such as sulfuric acid, nitric acid, hydrochloric acid, hydrobromic acid, etc., and organic acids such as acetic acid, p-toluenesulfonic acid, ethanesulfonic acid, oxalic acid, maleic acid, fumaric acid, citric acid, succinic acid, benzoic acid, etc. These salts are also useful as an active ingredient as like as the compounds (1) in the free form.

In addition, the compounds (1) of the present invention include stereoisomers and optical isomers, and these isomers are also useful as an active ingredient in this invention.

The compounds of the present invention thus obtained can easily be isolated from the reaction system and purified by conventional methods. The isolation and purification methods are, for example, distillation method, recrystallization method, column chromatography, ion exchange chromatography, gel chromatography, affinity chromatography, preparative thin layer chromatography, extraction with a solvent, and the like.

The active compounds (1) and their salts of the present invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (e.g. solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coated tablets, or double or multiple layer tablets. In the preparation of pills, the carriers include vehibles (e.g. glucose, lactose, starches, cacao butter, hydrogenated vegetable oils, kaolin, talc, etc.), binders (e.g. gum arabic powder, tragacanth powder, gelatin, ethanol, etc.), disintergrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of the present invention and the above carriers into hard gelatin capsules or soft capsules in a usual manner. In the preparation of injections, the solutions, emulsions or suspensions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents, and the like. Besides, the pharmaceutical preparations may optionally be incorporated with coloring agents, preservatives, perfumes, flavors, sweeting agents, and other medicines, if required.

The amount of the active compound of the present invention (active ingredient) to be incorporated into the anti-vasopressin preparations is not specified but may be selected from a broad range, but usually, it is preferably in the range of about 1 to about 70% by weight, more preferably about 5 to about 50% by weight.

The anti-vasopressin preparation of the present invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required. Suppositories are administered intrarectal route.

The dosage of the anti-vasopressin agent of the present invention may be selected in accordance with the usage, sexes and other conditions of the patients, the degree of severity of the diseases, and the like, but is usually in the range of about 0.6 to 50 mg of the active compound of the present invention per 1 kg of body weight of the patient per day. The active compound is preferably contained in an amount of about 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of the present invention.

PREPARATION 1

Film coated tablets are prepared from the following components.

| Components | Amount |
| --- | --- |
| 7-Hydroxy-5-methylamino-1-[4-(2-chlorobenzoylamino)benzoyl]-2,3,4,5-tetrahydro-1H-benzazepine | 150 g |
| Avicel (tradename; Asahi Chemical Industry Co, Ltd.) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active compound of the present invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

PREPARATION 2

Tablets are prepared from the following components.

| Components | Amount |
| --- | --- |
| 5-Dimethylamino-1-[4-(4-carbamoylbenzoylamino)benzoyl]-2,3,4,5-tetrahydro-1H-benzazepine | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of the present invention, citric acid, lactose, dicalcium phosphate, Pullonic F-68 and sodium laurylsulfate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and put into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

PREPARATION 3

An injection preparation is prepared from the following components.

| Components | Amount |
|---|---|
| 5-Dimethylamino-1-{4-[2-(3-methylphenyl)-acetylamino]benzoyl}-2,3,4,5-tetrahydro-1H-benzazepine | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of the present invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

To a solution of 5-dimethylamino-2,3,4,5-tetrahydro-1H-benzazepine (50 g) in a mixture of acetone (400 ml) and water (200 ml) is added potassium carbonate (38.8 g), and thereto is added p-nitrobenzoyl chloride (40 g) with stirring under ice-cooling, and the mixture is stirred at room temperature overnight. To the reaction mixture is added an appropriate amount of water, and the precipitated crystals are collected by filtration and dried to give 5-dimethylamino-1-(4-nitrobenzoyl)-2,3,4,5-tetrahydro-1H-benzazepine (71 g) as pale yellow powder, mp. 139°–142° C.

REFERENCE EXAMPLE 2

In ethanol (500 ml) is dispersed 10% Pd-C (5 g), and thereto is added 5-dimethylamino-1-(4-nitrobenzoyl)-2,3,4,5-tetrahydro-1H-benzazepine (64.1 g), and the mixture is subjected to catalytic reduction at ordinary room temperature under atmospheric pressure. After reduction, 10% Pd-C is removed by filtration, and the filtrate is concentrated under reduced pressure to give 5-dimethylamino-1-(4-aminobenzoyl)-2,3,4,5-tetrahydro-1H-benzazepine (56.1 g) as white powder, mp. 120°–122° C.

REFERENCE EXAMPLE 3

5-Hydroxy-7-chloro-1-[2-methoxy-4-(2-methylbenzoylamino)benzoyl]-2,3,4,5-tetrahydro-1H-benzazepine (0.7 g), dimethylaminopyridine (0.83 g) and dimethylaminopyridine hydrochloride (0.72 g) are dissolved in chloroform (15 ml), and thereto are added N-tert-butoxycarbonyl-L-methionine (0.56 g) and dicyclohexylcarbodiimide (0.93 g), and the mixture is stirred at room temperature for 3 hours. To the mixture are added methanol (3 ml) and acetic acid (0.7 ml), and the mixture is stirred at room temperature for 30 minutes. The insoluble materials are removed by filtration, and to the filtrate is added 5% aqueous sodium hydrogen sulfate solution, and the mixture is extracted with dichloromethane. The dichloromethane layer is washed successively with saturated aqueous sodium hydrogen carbonate solution and saturated brine, and dried over magnesium sulfate. The solvent is evaporated and the resulting residue is purified by silica gel column chromatography (eluent; dichloromethane:methanol=150:1) to give 5-(N-tert-butoxycarbonyl-L-methionyloxy)-7-chloro-1-[2-methoxy-4-(2-methylbenzoylamino)benzoyl]-2,3,4,5-tetrahydro-1H-benzazepine (1.27 g).

$^1$H-NMR (CDCl$_3$) δ; 1.29–2.92, 3.35–5.40, 6.09–6.35 (total 30H, m, 1.45 (s), 1.47 (s)), 6.61–8.00 (12H, m).

Using the appropriate starting compounds, the following compounds are obtained in the same manner as in Reference Example 3.

5-(N-tert-Butoxycarbonyl-L-alanyloxy)-1-[2-chloro-4-(2-methylbenzoylamino)benzoyl]-2,3,4,5-tetrahydro-1H-benzazepine $^1$H-NMR (CDCl$_3$) δ; 0.95–3.05, 3.29–5.22, 5.95–6.27 (total 23H, m), 6.86–8.17 (13H, m).

5-(N-tert-Butoxycarbonylglycyloxy)-1-[2-chloro-4-(2-methylbenzoylamino)benzoyl]-2,3,4,5-tetrahydro-1H-benzazepine $^1$H-NMR (CDCl$_3$) δ; 1.30–3.09, 3.69–5.29, 5.91–6.35 (total 21H, m), 6.77–8.48 (13H, m).

5-(N-tert-Butoxycarbonyl-L-methionyloxy)-1-[2-chloro-4-(2-methylbenzoylamino)benzoyl]-2,3,4,5-tetrahydro-1H-benzazepine $^1$H-NMR (CDCl$_3$) δ; 1.05–3.06, 3.25–3.63, 4.01–5.37 (total 26H, m), 5.97–6.28 (1H, m), 6.72–8.72 (13H, m).

REFERENCE EXAMPLE 4

Using the appropriate starting compounds, the following compounds are obtained in the same manner as in Reference Example 1.

5-(3-Hydroxypropoxy)-7-chloro-1-(2-methoxy-4-nitrobenzoyl)-2,3,4,5-tetrahydro-1H-benzazepine Pale yellow amorphous.

$^1$H-NMR (CDCl$_3$) δ; 1.4–2.6 (7H, m), 2.7–3.0 (1H, m), 3.0–4.1 (7H, m), 4.3–5.1 (2H, m), 6.6–7.0 (2H, m), 7.1–8.0 (4H, m).

5-[3-(p-Toluenesulfonyloxy)propoxy]-7-chloro-1-(2-methoxy-4-nitrobenzoyl)-2,3,4,5-tetrahydro-1H-benzazepine Pale yellow amorphous.

$^1$H-NMR (CDCl$_3$) δ; 1.35–2.65 (9H, m), 2.65–3.0 (1H, m), 3.05–3.95 (5H, m), 3.95–4.45 (2H, m), 4.5–5.05 (2H, m), 6.6–7.05 (2H, m), 7.1–8.05 (8H, m).

5-(2-Hydroxyethoxy)-7-chloro-1-(2-methoxy-4-nitrobenzoyl)-2,3,4,5-tetrahydro-1H-benzazepine Pale yellow amorphous.

$^1$H-NMR (CDCl$_3$) δ; 1.35–2.6 (4H, m), 2.7–3.0 (1H, m), 3.0–4.1 (7H, m), 4.35–5.0 (2H, m), 6.6–7.0 (2H, m), 7.1–8.05 (5H, m).

5-[2-(p-Toluenesulfonyloxy)ethoxy]-7-chloro-1-(2-methoxy-4-nitrobenzoyl)-2,3,4,5-tetrahydro-1H-benzazepine Colorless amorphous.

$^1$H-NMR (CDCl$_3$) δ; 1.35–2.6 (7H, m), 2.65–2.95 (1H, m), 3.0–3.95 (5H, m), 4.1–5.05 (4H, m), 6.55–7.05 (2H, m), 7.05–7.6 (4H, m), 7.65–8.0 (4H, m).

5-Methoxycarbonylmethyl-7-chloro-1-(2-methoxy-4-nitrobenzoyl)-2,3,4,5-tetrahydro-1H-benzazepine Pale yellow amorphous.

$^1$H-NMR (CDCl$_3$) δ; 1.2–1.5 (1H, m), 1.5–2.3 (3H, m), 2.6–2.95 (2H, m), 2.95–3.25 (1H, m), 3.3–4.2 (7H, m), 4.45–5.15 (1H, m), 6.65–6.85 (1H, m), 6.85–7.0 (1H, m), 7.02 (1H, d, J=1.8 Hz), 7.1–8.05 (3H, m).

5-Methoxycarbonylmethyl-7-chloro-1-(4-nitrobenzoyl)-2,3,4,5-tetrahydro-1H-benzazepine Pale yellow prisms.

$^1$H-NMR (CDCl$_3$) δ; 1.2–1.75 (2H, m), 1.75–2.3 (2H, m), 2.6–3.15 (1H, m), 3.15–3.4 (1H, m), 3.76 (3H, s), 4.05–5.2 (2H, m), 6.54 (1H, d, J=8.3 Hz), 6.92 (1H, dd,

J=8.3 Hz, 2.2 Hz), 7.1-7.25 (1H, m), 7.52 (2H, d, J=8.8 Hz), 8.06 (2H, dd, J=8.8 Hz, 2 Hz).

5-[2-(p-Toluenesulfonyloxy)ethyl]-7-chloro-1-(2-methoxy-4-nitrobenzoyl)-2,3,4,5-tetrahydro-1H-benzazepine
Pale yellow amorphous.
$^1$H-NMR (CDCl$_3$) δ; 1.0-1.4 (1H, m), 1.4-2.15 (4H, m), 2.15-2.4 (1H, m), 2.4-2.55 (3H, m), 2.9-3.3 (2H, m), 3.35-4.5 (6H, m), 6.6-8.0 (10H, m).

5-Cyanomethyl-7-chloro-1-(3-methoxy-4-nitrobenzoyl)-2,3,4,5-tetrahydro-1H-benzazepine
White powder.
$^1$H-NMR (CDCl$_3$) δ; 1.38-2.37, 2.66-4.22, 4.41-4.68, 5.03-5.24 [total 12H, m, (3.79(s))], 6.55-8.00 [6H, m, (6.76 (dd, J=1.6 Hz, 8.3 Hz)), (6.92 (d, J=1.4 Hz)), (7.23 (d, J=2.0 Hz))].

5-Ethoxycarbonylmethyl-7-chloro-1-(3-methoxy-4-nitrobenzoyl)-2,3,4,5-tetrahydro-1H-benzazepine
White powder.
$^1$H-NMR (CDCl$_3$) δ; 1.25-2.26, 2.61-4.66, 5.01-5.25 [total 17H, m, (1.28 (3H, t, J=7.1 Hz)), (3.83 (3H, s))], 6.57 (1H, d, J=9.5 Hz), 6.85-7.31 (4H, m), 7.63 (1H, d, J=8.3 Hz).

N-{[7-Fluoro-1-(2-chloro-4-nitrobenzoyl)-2,3,4,5-tetrahydro-1H-benzazepin-5-yl]oxymethylcarbonyl}-L-alanine methyl ester
Yellow oil.
$^1$H-NMR (CDCl$_3$) δ; 1.37-1.53 (3H, m), 1.54-4.25 (8H, m), 4.40-5.05 (3H, m), 6.65-8.35 (7H, m).

N-{[7-Fluoro-1-(2-chloro-4-nitrobenzoyl)-2,3,4,5-tetrahydro-1H-benzazepin-5-yl]oxymethylcarbonyl}-L-proline methyl ester
Yellow oil.
$^1$H-NMR (CDCl$_3$) δ; 1.37-4.19 (16H, m), 4.23-5.07 (3H, m), 6.56-8.43 (6H, m).

5-Methoxycarbonylmethyl-7-chloro-1-(2-methyl-4-nitrobenzoyl)-2,3,4,5-tetrahydro-1H-benzazepine
Yellow powder.
$^1$H-NHR (CDCl$_3$) δ; 1.50-2.31 (4H, m), 2.45-5.20 (5H, m), 2.57, 2.61 (3H, each s), 3.75 (3H, s), 6.55 (1H, d, J=8.4 Hz), 6.89 (1H, dd, J=2.3 Hz, 8.4 Hz), 7.09 (1H, d, J=2.3 Hz), 7.16 (1H, d, J=8.4 Hz), 7.78 (1H, dd, J=2.2 Hz, 8.4 Hz), 8.00 (1H, d, J=2.2 Hz).

5-Methoxycarbonylmethyl-7-chloro-1-(2-chloro-4-nitrobenzoyl)-2,3,4,5-tetrahydro-1H-benzazepine
Yellow powder.
mp. 133°-134° C.
$^1$H-NHR (CDCl$_3$) δ; 1.05-2.28 (4H, m), 2.57-3.05 (2H, m), 3.06-3.32 (1H, m), 3.33-3.85 (1H, m), 3.74 (3H, s), 4.39-4.67 (1H, m), 6.78-7.19 (3H, m), 7.38 (1H, d, J=8.2 Hz), 7.93 (1H, dd, J=8.2 Hz, 2.1 Hz), 8.17 (1H, d, J=2.1 Hz).

5-Methoxycarbonylmethyl-7-chloro-1-(3-methoxy-4-nitrobenzoyl)-2,3,4,5-tetrahydro-1H-benzazepine
Slightly yellow powder.
mp. 139.5°-141° C.
$^1$H-NHR (CDCl$_3$) δ; 1.16-2.31 (4H, m), 2.61-3.09 (2H, m), 3.12-3.40 (1H, m), 3.41-5.23 (2H, m), 3.72 (3H, s), 3.83 (3H, s), 6.58 (1H, d, J=8.3 Hz), 6.85-7.24 (4H, m), 7.63 (1H, d, J=8.3 Hz).

5-[2-(p-Toluenesulfonyloxy)ethoxy]-7-chloro-1-(2-methyl-4-nitrobenzoyl)-2,3,4,5-tetrahydro-1H-benzazepine
Yellow amorphous.
$^1$H-NHR (CDCl$_3$) δ; 1.12-5.14 (17H, m), 6.50 (1H, dd, J=16Hz, 8.4 Hz), 6.91 (1H, d, J=8.4 Hz), 7.10-8.45 (8H, m).

5-[3-(p-Toluenesulfonyloxy)propoxy]-7-chloro-1-(2-methyl-4-nitrobenzoyl)-2,3,4,5-tetrahydro-1H-benzazepine
Slightly yellow amorphous.
$^1$H-NHR (CDCl$_3$) δ; 1.09-3.08 (13H, m), 3.09-5.18 (6H, m), 6.50 (1H, dd, J=17.8 Hz, 8.4 Hz), 6.84-8.42 (9H, m).

5-(2-Methoxyacetyloxy)-7-chloro-1-(4-nitrobenzoyl)-2,3,4,5-tetrahydro-1H-benzazepine
Yellow amorphous.
$^1$H-NHR (CDCl$_3$) δ; 1.7-3.2 (5H, m), 3.36, 3.46 (total 3H, s), 4.10, 4.29 (total 2H, s), 4.7-5.2 (1H, m), 6.1-6.2 (1H, m), 6.57 (1H, d, J=8.3 Hz), 6.9-7.1 (1H, m), 7.2-7.5 (1H, m), 7.5-7.6 (2H, m), 8.0-8.2 (2H, m).

5-Methoxycarbonylmethyl-7-fluoro-1-(4-nitrobenzoyl)-2,3,4,5-tetrahydro-1H-benzazepine
Pale yellow oil.
$^1$H-NHR (CDCl$_3$) δ; 1.22-1.70 (2H, m), 1.77-2.23 (2H, m), 2.65-3.04 (2H, m), 3.12-3.30 (1H, m), 3.75 (3H, s), 4.07-4.35 (1H, m), 4.40-5.18 (1H, m), 6.44-6.70 (2H, m), 6.80-7.05 (1H, m), 7.40-7.60 (2H, m), 7.95-8.10 (2H, m), 8.15-8.28 (1H, m).

5-Hydroxy-7-fluoro-1-(2-methoxy-4-nitrobenzoyl)-2,3,4,5-tetrahydro-1H-benzazepine
Pale yellow amorphous.
$^1$H-NHR (CDCl$_3$) δ; 1.52-2.36 (4H, m), 2.68-2.95 (1H, m), 3.12 (1H, brs), 3.44-4.03 (3H, m), 4.65-5.17 (2H, m), 6.50-6.76 (2H, m), 6.80-8.03 (4H, m).

5-(3-Morpholinopropoxy)-7-fluoro-1-(2-methyl-4-nitrobenzoyl)-2,3,4,5-tetrahydro-1H-benzazepine
Pale yellow amorphous.
$^1$H-NHR (CDCl$_3$) δ; 1.43-2.62 (11H, m), 2.53, 2.59 (3H, s), 2.72-3.03 (1H, m), 3.10-3.83 (7H, m), 4.36-5.07 (2H, m), 6.46-6.71 (2H, m), 6.86-8.20 (4H, m).

5-[3-(1-Imidazolyl)propoxy]-7-fluoro-1-(2-methyl-4-nitrobenzoyl)-2,3,4,5-tetrahydro-1H-benzazepine
Pale yellow oil.
$^1$H-NHR (CDCl$_3$) δ; 1.37-2.63 (6H, m), 2.52, 2.59, 2.60 (total 3H, s), 2.73-3.05 (1H, m), 3.10-3.80 (2H, m), 3.96-5.07 (4H, m), 6.46-6.72 (2H, m), 6.85-7.20 (4H, m), 7.26-8.23 (3H, m).

5-Methoxycarbonylmethyl-7-fluoro-1-(2-methoxy-4-nitrobenzoyl)-2,3,4,5-tetrahydro-1H-benzazepine
Pale yellow amorphous.
$^1$H-NHR (CDCl$_3$) δ; 1.19-2.26 (4H, m), 2.57-2.90 (2H, m), 2.95-3.20 (1H, m), 3.35-4.27 (4H, m), 3.75 (3H, s), 4.48-5.12 (1H, m), 6.52-6.67 (1H, m), 6.71-8.02 (5H, m).

5-[2-(p-Toluenesulfonyloxy)ethoxy]-7-fluoro-1-(2-methoxy-4-nitrobenzoyl)-2,3,4,5-tetrahydro-1H-benzazepine
Pale yellow oil.
$^1$H-NHR (CDCl$_3$) δ; 1.34-1.88 (2H, m), 1.95-2.38 (2H, m), 2.40, 2.43, 2.45 (total 3H, s), 2.70-2.91 (1H, m), 3.43-4.00 (5H, m), 4.13-4.47 (2H, m), 4.56-5.03 (2H, m), 6.54-7.96 (10H, m).

5-(3-Hydroxypropoxy)-7-fluoro-1-(2-methyl-4-nitrobenzoyl)-2,3,4,5-tetrahydro-1H-benzazepine
Pale yellow amorphous.
$^1$H-NHR (CDCl$_3$) δ; 1.38-2.67 (8H, m), 2.53, 2.59 (total 3H, s), 2.72-3.08 (1H, m), 3.14-3.93 (5H, m), 4.25-5.11 (2H, m), 6.47-6.73 (2H, m), 6.86-8.18 (4H, m).

5-[3-(p-Toluenesulfonyloxy)propoxy]-7-fluoro-1-(2-methyl-4-nitrobenzoyl)-2,3,4,5-tetrahydro-1H-benzazepine
Pale yellow amorphous.
$^1$H-NHR (CDCl$_3$) δ; 1.38-2.63 (6H, m), 2.42, 2.44 (total 3H, s), 2.52, 2.57, 2.58 (total 3H, s), 2.73-3.03 (1H, m), 3.10–3.83 (2H, m), 4.05–5.03 (4H, m), 6.45–6.70 (2H, m), 6.86–8.19 (8H, m).

5-[3-(1-Pyrrolidinyl)propoxy]--7-fluoro-1-(2-methyl-4-nitrobenzoyl)-2,3,4,5-tetrahydro-1H-benzazepine hydroiodide
Pale yellow amorphous.
¹H-NHR (CDCl₃) δ; 1.40–1.90 (2H, m), 1.95–2.63 (7H, m), 2.53, 2.58, 2.59 (total 3H, s), 2.75–3.90 (10H, m), 4.42–4.98 (2H, m), 5.22 (1H, brs), 6.47–6.68 (2H, m), 6.92–7.38 (2H, m), 7.56–8.32 (2H, m).

5-(2-Hydroxyethoxy)-7-fluoro-1-(2-methyl-4-nitrobenzoyl)-2,3,4,5-tetrahydro-1H-benzazepine
Pale yellow oil.
¹H-NHR (CDCl₃) δ; 1.38–2.63 (5H, m), 2.53, 2.58, 2.59 (total 3H, s), 2.76–3.93 (4H, m), 4.40–5.00 (2H, m), 6.49–8.18 (6H, m).

5-Hydroxy-7-fluoro-1-(2-methyl-4-nitrobenzoyl)-2,3,4,5-tetrahydro-1H-benzazepine
Pale yellow powder.
¹H-NHR (DMSO-d₆) δ; 1.40–2.31 (4H, m), 2.49, 2.54, 2.55 (total 3H, s), 2.62–3.43 (1H, m), 4.55–5.06 (2H, m), 5.77 (1H, brs), 6.66–6.98 (2H, m), 7.10–7.50 (2H, m), 7.60–8.36 (2H, m).

5-Hydroxymethyl-7-fluoro-1-(2-methoxy-4-nitrobenzoyl)-2,3,4,5-tetrahydro-1H-benzazepine
Pale yellow amorphous.
¹H-NHR (CDCl₃) δ; 1.13–1.40 (1H, m), 1.46–2.31 (3H, m), 2.40–3.50 (2H, m), 2.66 (1H, brs), 3.55–4.13 (5H, m), 4.53–5.03 (1H, m), 6.57 (1H, dt, J=8.5 Hz, 2.8 Hz), 6.67–7.18 (2H, m), 7.28–8.03 (3H, m).

5-(2-Hydroxyethyl)-7-chloro-1-(2-methyl-4-nitrobenzoyl)-2,3,4,5-tetrahydro-1H-benzazepine
White amorphous.
¹H-NHR (CDCl₃) δ; 1.38–2.35 (7H, m), 2.36–4.00 (7H, m), 4.30–4.53 (1H, m), 6.57 (1H, d, J=8.3 Hz), 6.89 (1H, dd, J=2.2 Hz, 8.3 Hz), 7.03 (1H, d, J=8.3 Hz), 7.13 (1H, d, J=2.2 Hz), 7.67–7.82 (1H, m), 7.91–8.08 (1H, m).

5-[2-(p-Toluenesulfonyloxy)ethyl]-7-chloro-1-(2-methyl-4-nitrobenzoyl)-2,3,4,5-tetrahydro-1H-benzazepine
White powder.
¹H-NHR (CDCl₃) δ; 1.07–2 78 (13H, m (2.46 s)), 2.79–3.38 (2H, m), 3.97–4.48 (2H, m), 6.56 (1H, d, J=8.2 Hz), 6.90 (1H, dd, J=2.2 Hz, 8.2 Hz), 6.93 (1H, d, J=8.4 Hz), 7.02 (1H, d, J=2.2 Hz), 7.20–7.64 (2H, m), 7.72–7.91 (3H, m), 7.98 (1H, d, J=2.1 Hz).

REFERENCE EXAMPLE 5

Using the appropriate starting compounds, the following compounds are obtained in the same manner as in Reference Example 2.

5-[3-(p-Toluenesulfonyloxy)propoxy]-7-chloro-1-(2-methoxy-4-aminobenzoyl)-2,3,4,5-tetrahydro-1H-benzazepine
Pink amorphous.
¹H-NMR (CDCl₃) δ; 1.3–2.35 (6H, m), 2.44 (3H, s), 2.55–4.0 (8H, m), 4.25 (2H, t, J=6 Hz), 4.5–5.15 (2H, m), 5.93 (1H, s), 6.1–6.45 (1H, m), 6.66 (1H, d, J=8.4 Hz), 6.88 (1H, dd, J=8.4 Hz, 2.4 Hz), 6.99 (1H, d, J=8 Hz), 7.29 (1H, s), 7.35 (2H, d, J=8.2 Hz), 7.81 (2H, d, J=8.3 Hz).

5-[2-(p-Toluenesulfonyloxy)ethoxy]-7-chloro-1-(2-methoxy-4-aminobenzoyl)-2,3,4,5-tetrahydro-1H-benzazepine
Pale yellow amorphous.
¹H-NMR (CDCl₃) δ; 1.3–2.35 (4H, m), 2.45 (3H, s), 2.65–2.95 (1H, m), 3.05–4.0 (7H, m), 4.0–5.1 (4H, m), 5.90 (1H, brs), 6.05–6.4 (1H, m), 6.64 (1H, d, J=8.3 Hz), 6.75–7.15 (2H, m), 7.15–7.55 (3H, m), 7.83 (2H, d, J=8.2 Hz).

5-Methoxycarbonylmethyl-7-chloro-1-(2-methoxy-4-aminobenzoyl)-2,3,4,5-tetrahydro-1H-benzazepine
Pale yellow amorphous.
¹H-NMR (CDCl₃) δ; 1.15–2.3 (4H, m), 2.55–3.25 (3H, m), 3.3–4.05 (9H, m), 4.1–4.7 (1H, m), 5.85–6.45 (2H, m), 6.65–6.8 (1H, m), 6.8–7.4 (3H, m).

5-Methoxycarbonylmethyl-7-chloro-1-(4-aminobenzoyl)-2,3,4,5-tetrahydro-1H-benzazepine
Colorless prisms (recrystallized from ethanol).
¹H-NMR (CDCl₃) δ; 1.15–2.3 (4H, m), 2.5–3.05 (2H, m), 3.05–3.3 (1H,m), 3.3–4.3 (6H, m), 4.35–5.3 (1H, m), 6.43 (2H, d, J=8.5 Hz), 6.61 (1H, d, J=8.4 Hz), 6.85–7.0 (1H, m), 7.0–7.4 (3H, m).

5-[2-(p-Toluenesulfonyloxy)ethyl]-7-chloro-1-(2-methoxy-4-aminobenzoyl)-2,3,4,5-tetrahydro-1H-benzazepine
Pale yellow amorphous.
¹H-NMR (CDCl₃) δ; 1.0–2.4 (6H, m), 2.46 (3H, s), 2.5–4.4 (10H, m), 5.85–7.25 (6H, m), 7.3–7.5 (2H, m), 7.65–7.9 (2H, m).

5-Cyanomethyl-7-chloro-1-(3-methoxy-4-aminobenzoyl)-2,3,4,5-tetrahydro-1H-benzazepine
White powder.
¹H-NMR (CDCl₃) δ; 1.21–2.33, 2.40–4.70, 5.05–5.39 (total 14H, m), 6.38–7.42 (4H, m), 6.43 (1H, d, J=8.1 Hz), 7.04 (1H, dd, J=2.3 Hz, 8.4 Hz).

5-Ethoxycarbonylmethyl-7-chloro-1-(3-methoxy-4-aminobenzoyl)-2,3,4,5-tetrahydro-1H-benzazepine
Colorless amorphous.
¹H-NMR (CDCl₃) δ; 1.11–2.28 [7H, m, (1,27 (t, J=7.1 Hz))], 2.49–4.61, 5.01–5.35 (total 12H, 3.68 (s)), 6.40 (1H, d, J=8.0 Hz),,.6.49–7.44 (4H, m), 6.95 (1H, dd, J=2.3 Hz, 8.3 Hz).

5-Methoxycarbonylmethyl-7-chloro-1-(2-methyl-4-aminobenzoyl)-2,3,4,5-tetrahydro-1H-benzazepine
¹H-NMR (CDCl₃) δ; 0.83–2.47 (4H, m), 2.37 (3H, s), 2.48–5.25 (7H, m), 3.72 (3H, s), 6.16 (1H, d, J=8.3 Hz), 6.41 (1H, s), 6.54 (1H, d, J=8.3 Hz), 6.64 (1H, d, J=8.2 Hz), 6.90 (1H, d, J=8.2 Hz), 7.00–7.42 (1H, m).

N-{[7-Fluoro-1-(2-chloro-4-aminobenzoyl)-2,3,4,5-tetrahydro-1H-benzazepin-5-yl]oxymethylcarbonyl}-L-alanine methyl ester
Slightly yellow amorphous.
¹H-NMR (CDCl₃) δ; 1.35–1.51 (3H, m), 1.51–5.14 (15H, m), 6.10–7.42 (7H, m).

N-{[7-Fluoro-1-(2-chloro-4-aminobenzoyl)-2,3,4,5-tetrahydro-1H-benzazepin-5-yl]oxymethylcarbonyl}-L-proline methyl ester
Slightly yellow amorphous.
¹H-NMR (CDCl₃) δ; 1.33–2.64 (8H, m), 2.64–3.00 (1H, m), 3.01–4.44 (9H, m), 4.45–5.13 (3H, m), 6.12–7.46 (6H, m).

5-Methoxycarbonylmethyl-7-chloro-1-(2-chloro-4-aminobenzoyl)-2,3,4,5-tetrahydro-1H-benzazepine
Yellow amorphous.
¹H-NHR (CDCl₃); 1.09–2.36 (4H, m), 2.45–5.19 (7H, m), 3.71 (3H, s), 6.12–7.50 (2H, m), 6.27 (1H, dd, J=2.1 Hz, 8.3 Hz), 6.54 (1H, d, J=2.1 Hz), 6.92 (1H, d, J=2.1 Hz), 7.05 (1H, dd, J=2.1 Hz, 6.1 Hz).

5-Methoxycarbonylmethyl-7-chloro-1-(3-methoxy-4-aminobenzoyl)-2,3,4,5-tetrahydro-1H-benzazepine
Slightly yellow amorhpous.
¹H-NHR (CDCl₃) δ; 1.01–2.29 (4H, m), 2.44–3.31 (3H, m), 3.32–5.29 (4H, m), 3.68, 3.71 (each 3H, s), 6.41

(1H, d, J=8.0 Hz), 6.50–6.78 (2H, m), 6.79–6.91 (1H, m), 6.95 (1H, d, J=8.4 Hz), 7.04–7.24 (1H, m).

5-[2-(p-Toluenesulfonyloxy)ethoxy]-7-chloro-1-(2-methyl-4-aminobenzoyl)-2,3,4,5-tetrahydro-1H-benzazepine Yellow amorphous.

¹H-NHR (CDCl₃) δ; 1.01–2.52 (4H, m), 2.32 (3H, s), 2.43 (3H, s), 3.53–4.78 (9H, m), 5.86–8.03 (10H, m).

5-[3-(p-Toluenesulfonyoxy)propoxy]-7-chloro-1-(2-methyl-4-aminobenzoyl)-2,3,4,5-tetrahydro-1H-benzazepine Slightly yellow amorphous.

¹H-NHR (CDCl₃) δ; 1.13–3.03 (7H, m), 2.33–2.43 (6H, each s), 3.04–5.18 (8H, m), 5.98–8.07 (10H, m).

5-(2-Methoxyacetyloxy)-7-chloro-1-(4-aminobenzoyl)-2,3,4,5-tetrahydro-1H-benzazepine White powder.

mp. 166°–169° C.

(recrystallized from dichloromethane/diethyl ether).

5-Methoxycarbonylmethyl-7-fluoro-1-(4-aminobenzoyl)-2,3,4,5-tetrahydro-1H-benzazepine Pale yellow oil.

¹H-NHR (CDCl₃) δ; 1.06–2.20 (4H, m), 2.40–3.22 (3H, m), 3.26–4.28 (3H, m), 3.71 (3H, s), 4.35–5.30 (1H, m), 6.23–6.45 (2H, m), 6.53–6.72 (2H, m), 6.75–7.20 (3H, m).

5-(3-Morpholinopropoxy)-7-fluoro-1-(2-methyl-4-aminobenzoyl)-2,3,4,5-tetrahydro-1H-benzazepine Pale yellow amorphous.

¹H-NHR (CDCl₃) δ; 1.41–2.63 (10H m) 2 33 (3H s), 2.75–3.00 (1H, m), 3.32–3.92 (8H, m), 4.27–5.16 (2H, m), 5.98–6.75 (4H, m), 6.80–7.38 (2H, m).

5-[2-(p-Toluenesulfonyloxy)ethoxy]-7-fluoro-1-(2-methoxy-4-aminobenzoyl)-2,3,4,5-tetrahydro-1H-benzazepine Pale yellow oil.

¹H-NHR (CDCl₃) δ; 1.29–2.30 (4H, m), 2.45 (3H, s), 2.62–2.88 (1H, m), 2.96–3.97 (4H, m), 3.46 (3H, s), 4.08–4.43 (2H, m), 4.52–5.07 (2H, m), 5.86–6.00 (1H, m), 6.06–6.38 (1H, m), 6.47–6.75 (2H, m), 6.90–7.40 (2H, m), 7.36 (2H, d, J=8.2 Hz), 7.82 (2H, d, J=8.2 Hz).

5-[3-(1-Pyrrolidinyl)propoxy]-7-fluoro-1-(2-methyl-4-aminobenzoyl)-2,3,4,5-tetrahydro-1H-benzazepine.

Pale yellow amorphous.

¹H-NHR (CDCl₃) δ; 1.40–2.70 (16H, m), 2.33 (3H, s), 2.73–2.96 (1H, m), 3.30–3.86 (4H, m), 4.28–5.14 (2H, m), 6.00–6.25 (1H, m), 6.30–6.72 (4H, m), 6.75–7.35 (1H, m).

5-[2-(1,3-Dioxo-1,2,3,4,5,6,7-octahydroisoindol-2-yl)ethoxy]-7-fluoro-1-(2-methyl TM 4-aminobenzoyl)-2,3,4,5-tetrahydro-1H-benzazepine Colorless oil.

¹H-NHR (CDCl₃) δ; 1.30–2.47 (13H, m), 2.33 (3H, s), 2.66–4.01 (8H, m), 4.32–5.13 (2H, m), 6.04–6.26 (4H, m), 6.80–7.36 (2H, m).

5-Methoxycarbonylmethyl-7-fluoro-1-(2-methoxy-4-aminobenzoyl)-2,3,4,5-tetrahydro-1H-benzazepine Pale yellow amorphous.

¹H-NHR (CDCl₃) δ; 1.41–2.15 (4H, m), 2.57–3.14 (3H, m), 3.35–4.31 (3H, m), 3.59 (3H, s), 3.74 (3H, s), 4.45–5.15 (1H, m), 5.88–6.17 (2H, m), 6.51–7.07 (4H, m).

5-[2-(p-Toluenesulfonyloxy)ethyl]-7-chloro-1-(2-methyl-4-aminobenzoyl)-2,3,4,5-tetrahydro-1H-benzazepine Yellow amorphous.

¹H-NHR (CDCl₃) δ; 1.10–2.53 (13H, m (2.31, 2.45 each 3H, each s)), 2.54–4.46 (6H, m), 5.95–6.70 (3H, m), 6.71–7.56 (5H, m (7.36, 2H, d, J=8.1 Hz)), 7.80 (2H, d, J=8.1 Hz).

EXAMPLE 1

To a solution of 5-dimethylamino-2,3,4,5-tetrahydro-1H-benzazepine (50 g) in a mixture of acetone (400 ml) and water (200 ml) is added potassium carbonate (38.8 g), and thereto is added 4-[2-(2-chlorophenyl)acetylamino]benzoyl chloride (66.5 g) with stirring under ice-cooling, and the mixture is stirred at room temperature overnight. Water is added to the reaction mixture, and the mixture is extracted with dichloromethane. The extract is dried over magnesium sulfate, and the solvent is distilled off under reduced pressure. The resulting residue is purified by silica gel column chromatography, and recrystallized from methanol to give 5-dimethyl-1-{4-[2-(2-chlorophenyl)acetylamino]benzoyl}-2,3,4,5-tetrahydro-1H-benzazepine (99.3 g) as white powder, mp. 187°–189° C.

EXAMPLE 2

To 2-chlorophenylacetic acid (0.44 g) is added thionyl chloride (15 ml), and the mixture is stirred at room temperature for 2 hours. Thionyl chloride is distilled off, and the resultant is further distilled off by subjecting twice to azeotrophy with toluene. The resulting residue is dissolved in dichloromethane (10 ml). Separately, to a solution of 5-dimethylamino-1-(4-aminobenzoyl)-2,3,4,5-tetrahydro-1H-benzazepine (0.40 g) in dichloromethane is added triethylamine (0.36 ml) under ice-cooling, and thereto is added dropwise the above obtained 2-(2-chlorophenyl)acetyl chloride solution. After addition, the mixture is stirred at room temperature for one hour, washed twice with water, dried over magnesium sulfate, and concentrated. The resulting residue is purified by silica gel column chromatography (eluent; chloroform:methanol=200:1), and recrystallized from methanol/diethyl ether to give 5-dimethylamino-1-{4-[2-(2-chlorophenyl)acetylamino]benzoyl}-2,3,4,5-tetrahydro-1H-benzazepine (0.29 g) as white powder, mp. 187°–189° C.

EXAMPLE 3 TO 85

Using the appropriate starting compounds, the following compounds of Table 1 are obtained in the same manner as in Examples 1 and 2.

Table 1

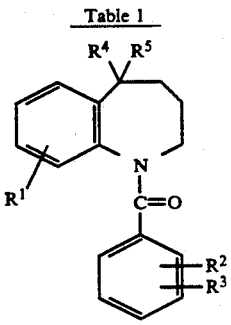

EXAMPLE 3

Structure:

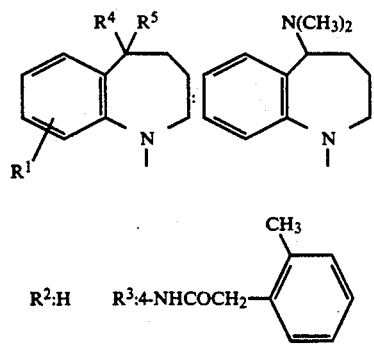

R²:H  R³:4-NHCOCH₂— (2-methylphenyl)

Crystalline form; White powder.
Recrystallization solvent: Methanol/diethyl ether.
Melting point: 153°-154.5° C.
Form: Free.

EXAMPLE 4

Structure:

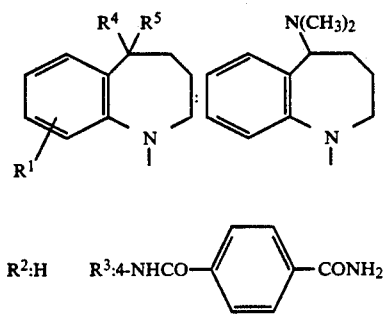

R²:H  R³:4-NHCO—(phenyl)—CONH₂

Crystalline form: White powder.
Recrystallization solvent: Diethyl ether.
Melting point: 226°-231° C. 1
Form: Free.

EXAMPLE 5

Structure:

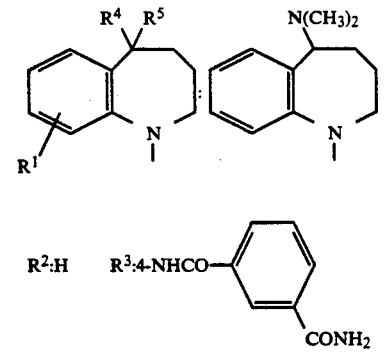

R²:H  R³:4-NHCO—(phenyl)—CONH₂

Crystalline form: White powder.
Recrystallization solvent: Ethanol/n-hexane.
Melting point: 224°-229° C.
Form: Free.

EXAMPLE 6

Structure:

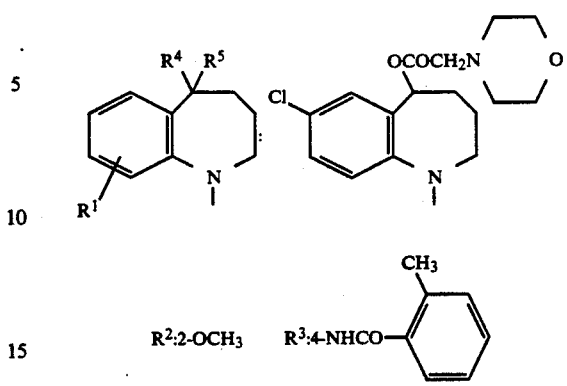

R²:2-OCH₃  R³:4-NHCO—(2-methylphenyl)

Crystalline form: White powder.
Recrystallization solvent: Ethanol/diethyl ether.
Melting point: 179°-181° C.
Form: Hydrochloride.

EXAMPLE 7

Structure:

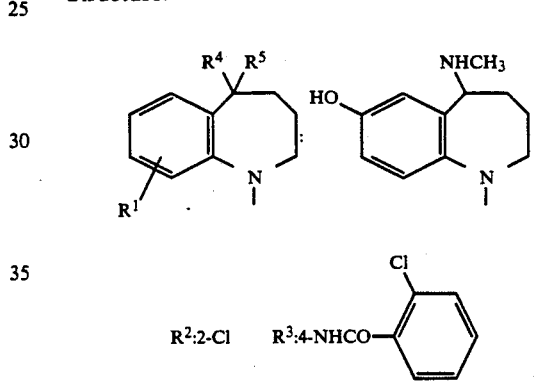

R²:2-Cl  R³:4-NHCO—(2-chlorophenyl)

Crystalline form: Colorless amorphous.
Form: Free.
NMR analysis: 1).

EXAMPLE 8

Structure:

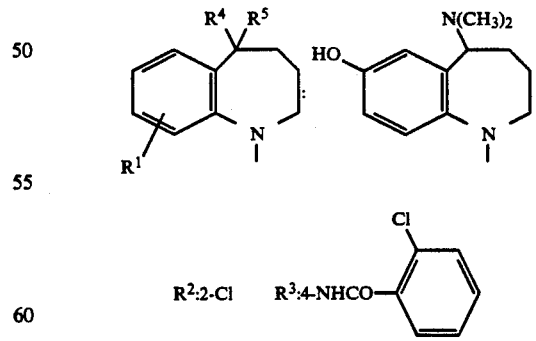

R²:2-Cl  R³:4-NHCO—(2-chlorophenyl)

Crystalline form: Colorless amorphous.
Form: Free.
NMR analysis: 2).

EXAMPLE 9

Structure:

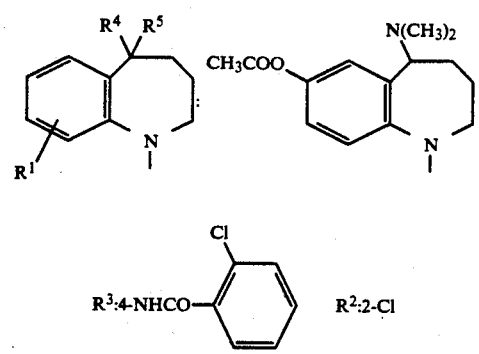

Crystalline form: Colorless amorphous.
Form: Free.
NMR analysis: 3).

EXAMPLE 10
Structure:

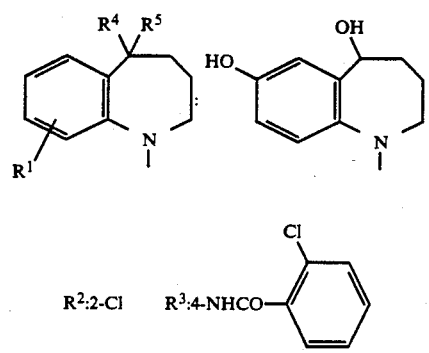

Crystalline form; Colorless amorphous.
Form: Free.
NMR analysis: 4).

EXAMPLE 11
Structure:

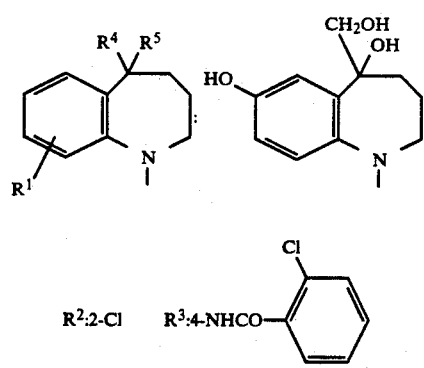

Crystalline form: Colorless amorphous.
Form: Free.
NMR analysis: 5).

EXAMPLE 12
Structure:

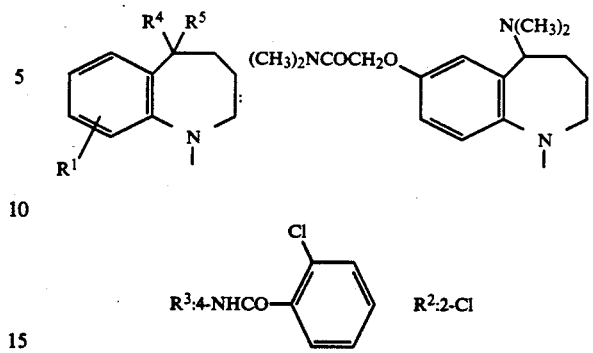

Crystalline form: Colorless amorphous.
Form: Free.
NMR analysis: 6).

EXAMPLE 13
Structure:

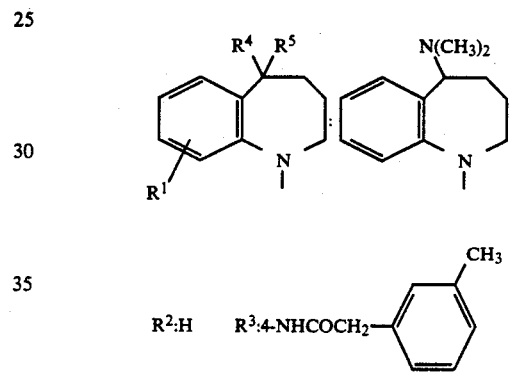

Crystalline form: Colorless amorphous.
Form: Free.
NMR analysis: 7).

EXAMPLE 14
Structure:

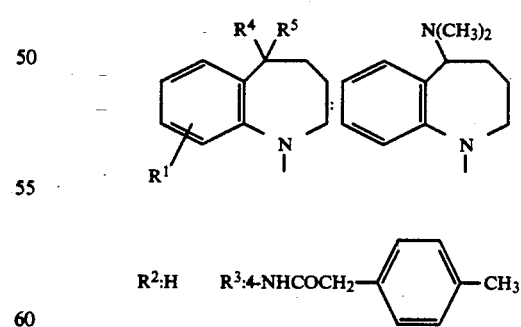

Crystalline form: Colorless amorphous.
Form: Free.
NMR analysis: 8).

EXAMPLE 15
Structure:

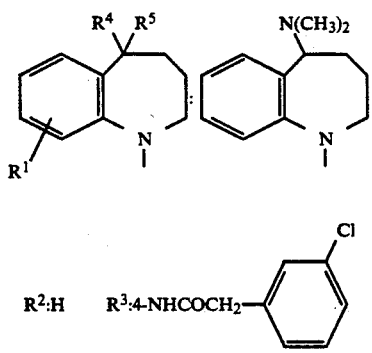

Crystalline form; Colorless amorphous.
Form: Free.
NMR analysis: 9).

EXAMPLE 16

Structure:

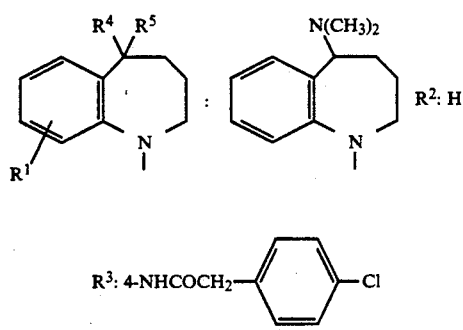

Crystalline form: Colorless amorphous.
Form: Free.
NMR analysis: 10).

EXAMPLE 17

Structure:

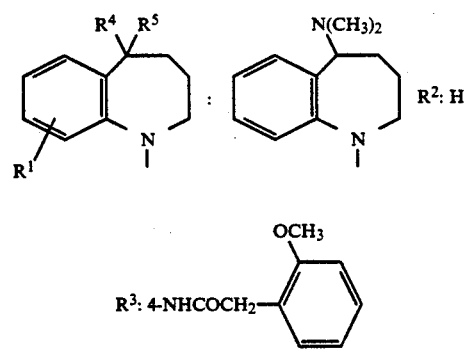

Crystalline form: Colorless amorphous.
Form: Free.
NMR analysis: 11).

EXAMPLE 18

Structure:

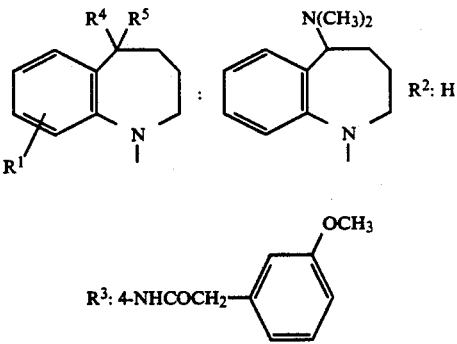

Crystalline form: colorless amorphous.
Form: Free.
NMR analysis: 12).

EXAMPLE 19

Structure:

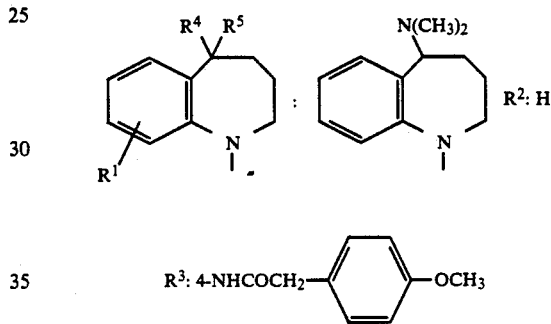

Crystalline form: colorless amorphous.
Form: Free.
NMR analysis: 13).

EXAMPLE 20

Structure:

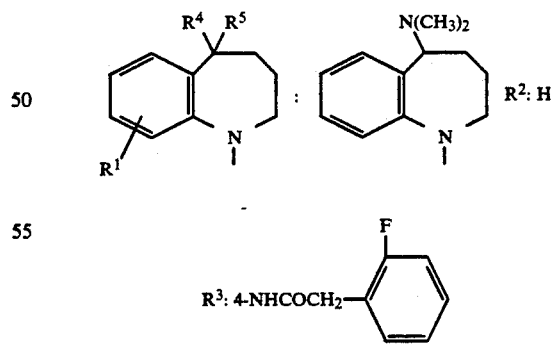

Crystalline form: White powder.
Recrystallization solvent: Methanol/diethyl ether.
Melting point: 189.5°–191° C.
Form: Free.

EXAMPLE 21

Structure:

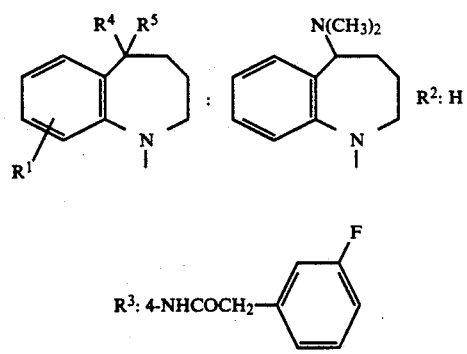

Crystalline form: Colorless amorphous.
Form: Free.
NMR analysis: 14).

EXAMPLE 22

Structure:

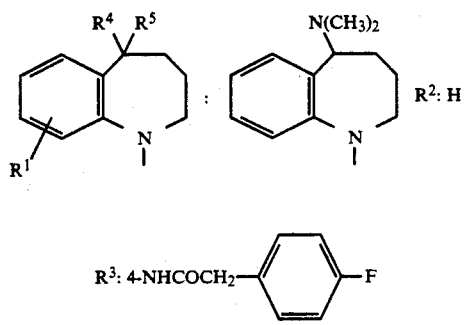

Crystalline form: Colorless amorphous.
Form: Free.
NMR analysis: 15).

EXAMPLE 23

Structure:

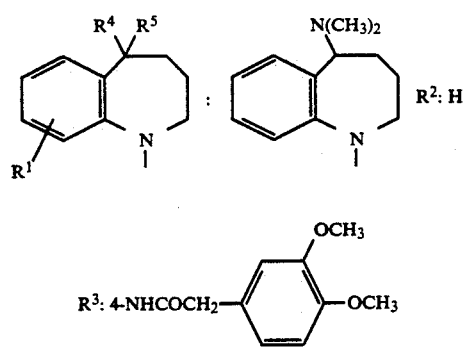

Crystalline form: Colorless amorphous.
Form: Free.
NMR analysis: 16).

EXAMPLE 24

Structure:

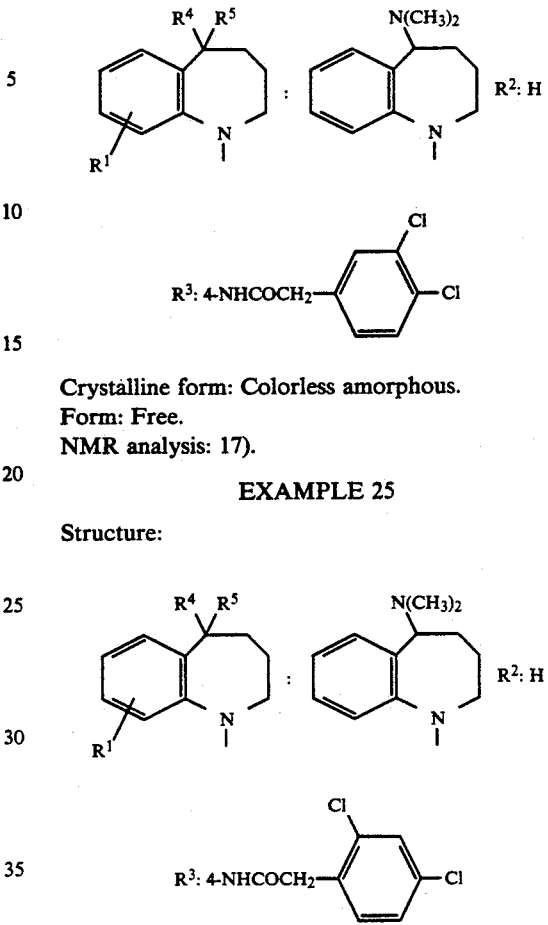

Crystalline form: Colorless amorphous.
Form: Free.
NMR analysis: 17).

EXAMPLE 25

Structure:

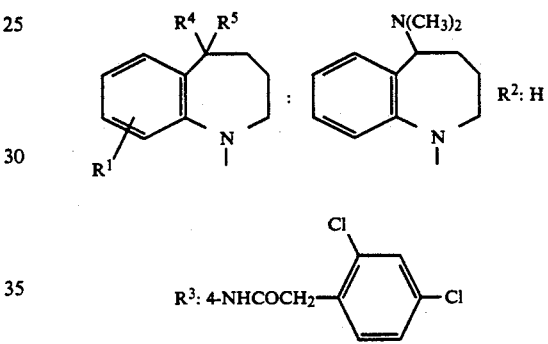

Crystalline form: colorless amorphous.
Form: Free.
NMR analysis: 18).

EXAMPLE 26

Structure:

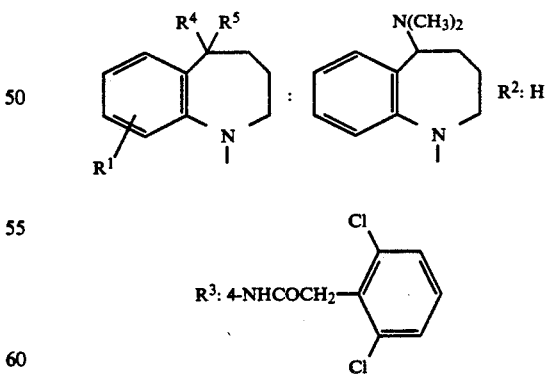

Crystalline form: colorless amorphous.
Form: Free.
NMR analysis: 19).

EXAMPLE 27

Structure:

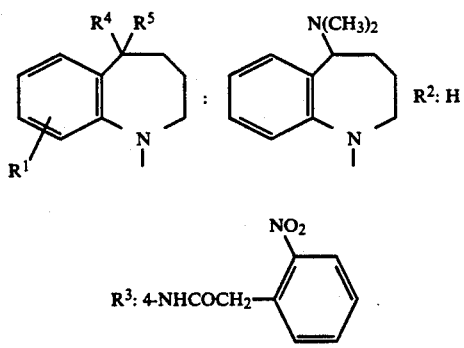

Crystalline form: Colorless amorphous.
Form: Free.
NMR analysis: 20).

EXAMPLE 28

Structure:

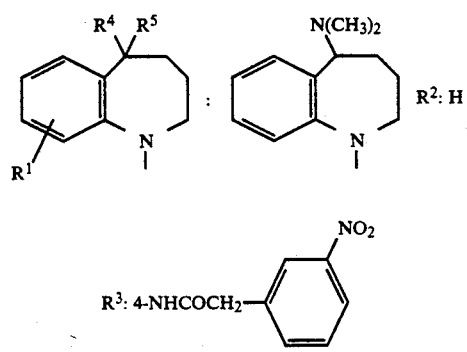

Crystalline form: Colorless amorphous.
Form: Free.
NMR analysis: 21).

EXAMPLE 29

Structure:

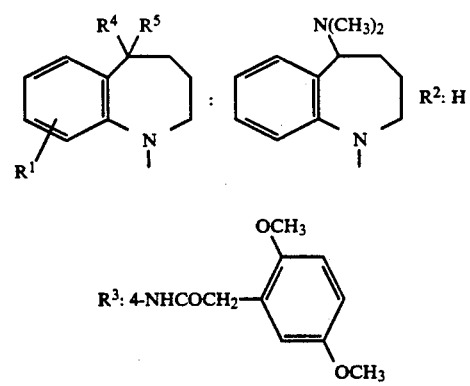

Crystalline form: Colorless amorphous.
Form: Free.
NMR analysis: 22).

EXAMPLE 30

Structure:

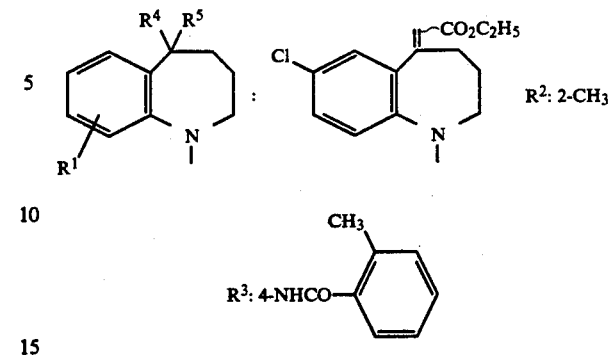

Crystalline form: Colorless amorphous.
Form: Free.
NMR analysis: 23).

EXAMPLE 31

Structure:

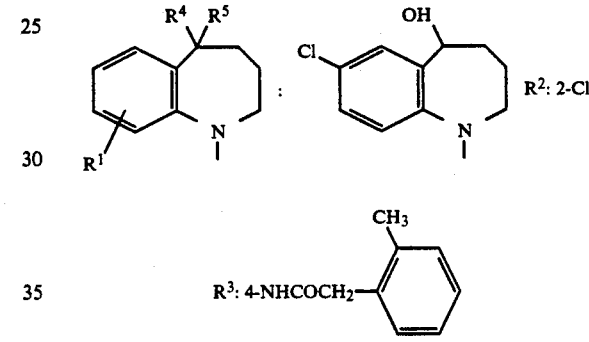

Crystalline form: White powder.
Recrystallization solvent: Methanol/diethyl ether.
Melting point: 192.5°–194.5° C.
Form: Free.

EXAMPLE 32

Structure:

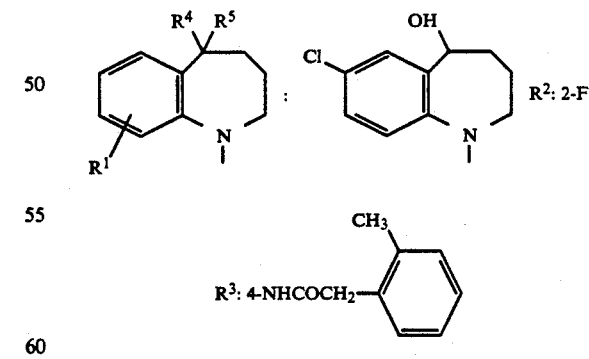

Crystalline form: White powder.
Recrystallization solvent: methanol/diethyl ether.
Melting point: 210°–211° C.
Form: Free.

EXAMPLE 33

Structure:

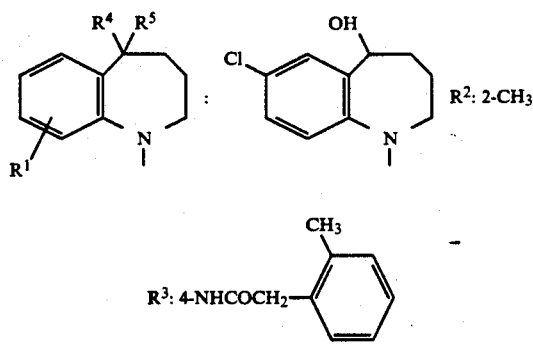 R²: 2-CH₃

R³: 4-NHCOCH₂- (o-methylphenyl)

Crystalline form: White powder.
Recrystallization solvent: methanol/diethyl ether.
Melting point: 221°–222° C.
Form: Free.

EXAMPLE 34

Structure:

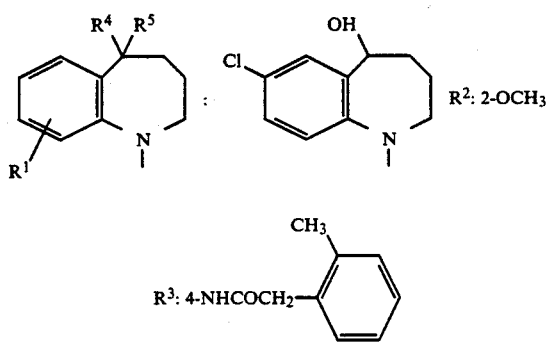 R²: 2-OCH₃

R³: 4-NHCOCH₂- (o-methylphenyl)

Crystalline form: Colorless amorphous.
Form: Free.
NMR analysis: 24).

EXAMPLE 35

Structure.

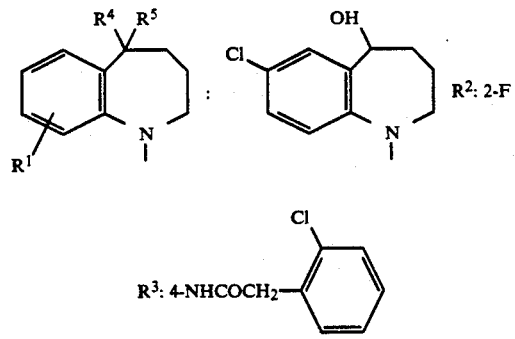 R²: 2-F

R³: 4-NHCOCH₂- (o-chlorophenyl)

Crystalline form: White powder.
Recrystallization solvent: Methanol/diethyl ether.
Melting point: 175°–176° C.
Form: Free.

EXAMPLE 36

Structure:

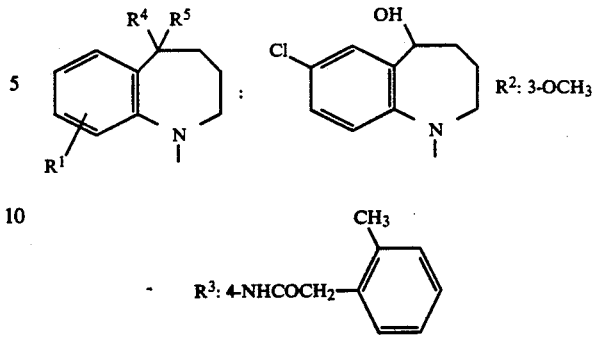 R²: 3-OCH₃

R³: 4-NHCOCH₂- (o-methylphenyl)

Crystalline form: White powder.
Recrystallization solvent: Methanol/diethyl ether.
Melting point: 212°–215° C.
Form: Free.

EXAMPLE 37

Structure:

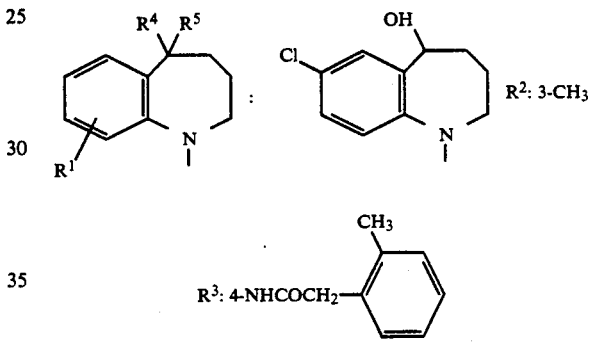 R²: 3-CH₃

R³: 4-NHCOCH₂- (o-methylphenyl)

Crystalline form: White powder.
Recrystallization solvent: Methanol/diethyl ether.
Melting point: 210°–211° C.
Form: Free.

EXAMPLE 38

Structure:

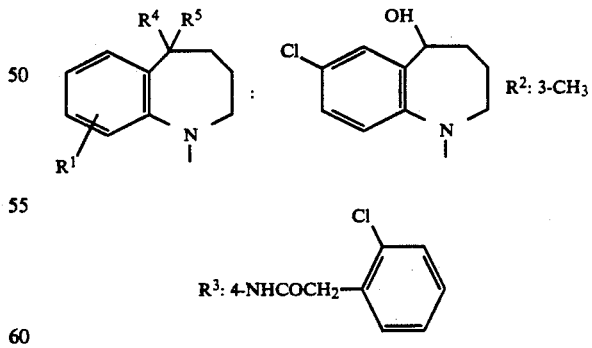 R²: 3-CH₃

R³: 4-NHCOCH₂- (o-chlorophenyl)

Crystalline form: White powder.
Recrystallization solvent: Methanol.
Melting point: 217°–218° C.
Form: Free.

EXAMPLE 39

Structure:

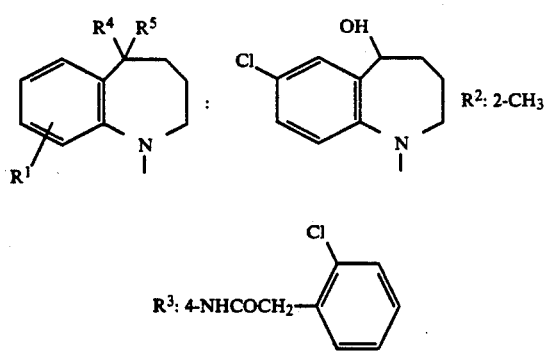

Crystalline form: White powder.
Recrystallization solvent: Methanol.
Melting point: 245°–247° C.
Form: Free.

EXAMPLE 40

Structure:

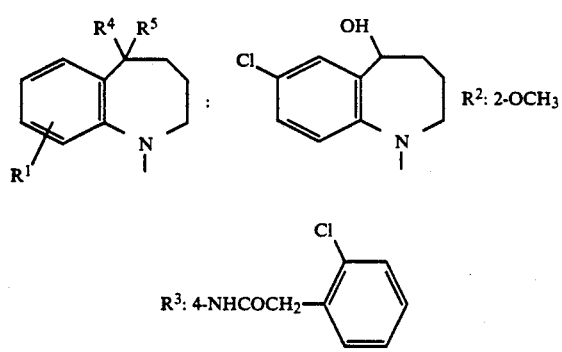

Crystalline form: Colorless amorphous.
Form: Free.
NMR analysis: 25).

EXAMPLE 41

Structure:

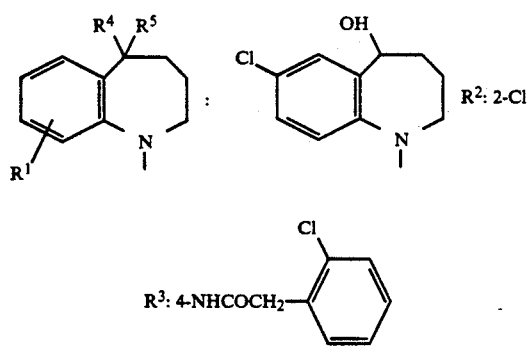

Crystalline form: White powder.
Recrystallization solvent: methanol/diethyl ether.
Melting point: 214°–216° C.
Form: Free.

EXAMPLE 42

Structure:

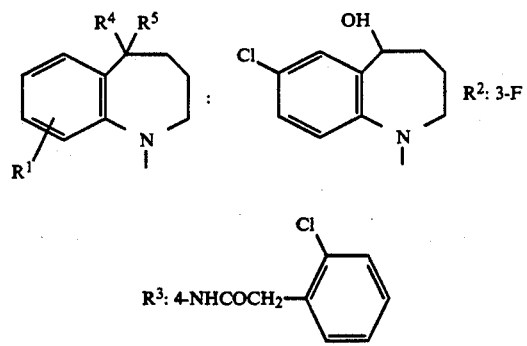

Crystalline form: White powder.
Recrystallization solvent: Methanol.
Melting point: 208.5°–209° C.
Form: Free.

EXAMPLE 43

Structure:

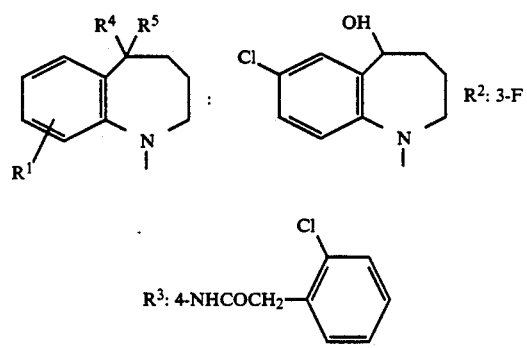

Crystalline form: White powder.
Recrystallization solvent: Methanol.
Melting point: 184.0°–186° C.
Form: Free.

EXAMPLE 44

Structure:

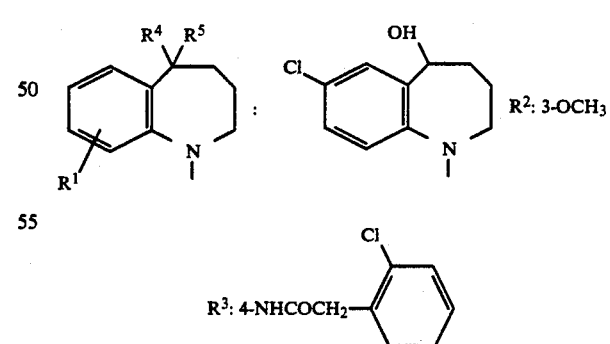

Crystalline form: White powder.
Recrystallization solvent: Methanol/diethyl ether.
Melting point: 195°–196° C.
Form: Free.

EXAMPLE 45

Structure:

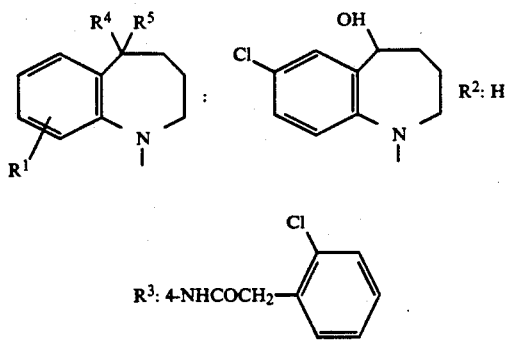

Crystalline form: White powder.
Recrystallization solvent: Methanol/diethyl ether.
Melting point: 214°–215° C.
Form: Free.

EXAMPLE 46

Structure:

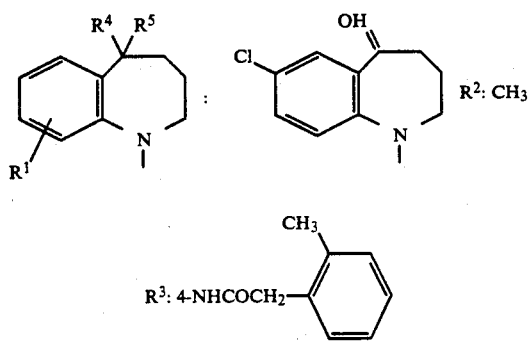

Crystalline form: White powder.
Recrystallization solvent: Methanol/diethyl ether.
Melting point: 145°–146.5° C.
Form: Free.

EXAMPLE 47

Structure:

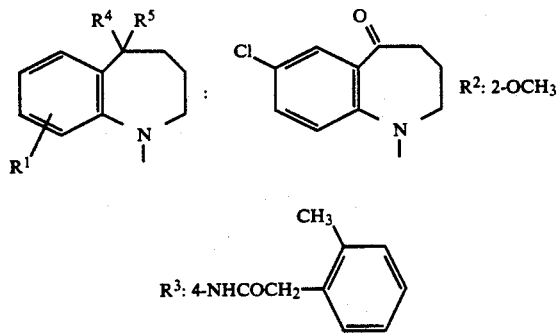

Crystalline form: White powder.
Recrystallization solvent: Methanol/diethyl ether.
Melting point: 241°–241.5° C.
Form: Free.

EXAMPLE 48

Structure:

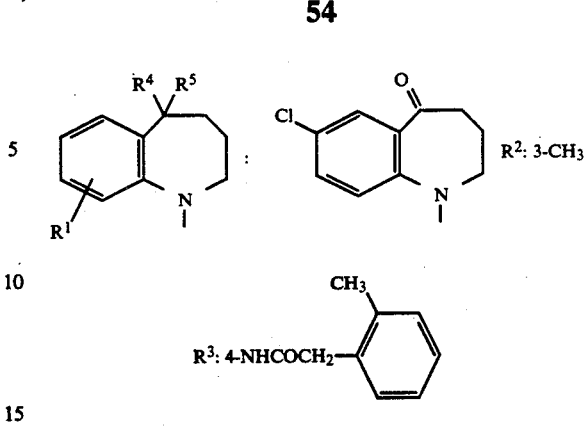

Crystalline form: White powder.
Recrystallization solvent: Methanol/diethyl ether.
Melting point: 119°–120° C.
Form: Free.

EXAMPLE 49

Structure:

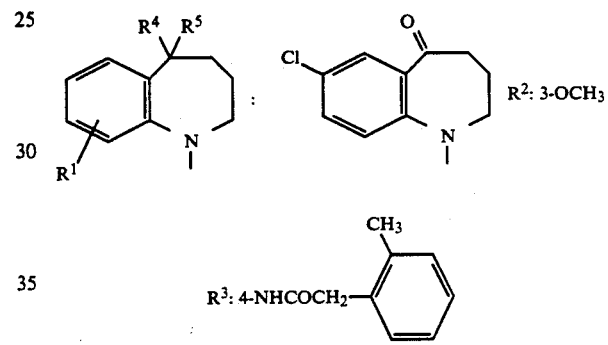

Crystalline form: White powder.
Recrystallization solvent: Methanol/diethyl ether.
Melting point: 142.5°–146.5° C.
Form: Free.

EXAMPLE 50

Structure:

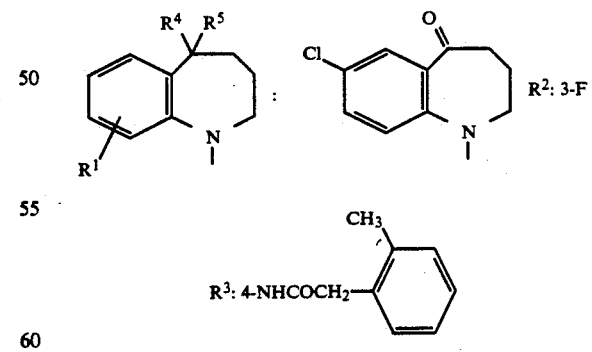

Crystalline form: White powder.
Recrystallization solvent: Methanol/diethyl ether.
Melting point: 145°–146° C.
Form: Free.

EXAMPLE 51

Structure:

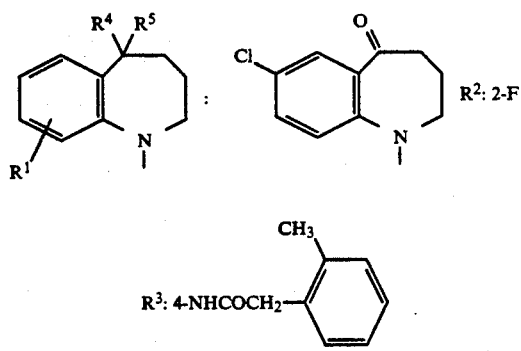

Crystalline form: colorless amorphous.
Form: Free.
NMR analysis: 26).

EXAMPLE 52

Structure:

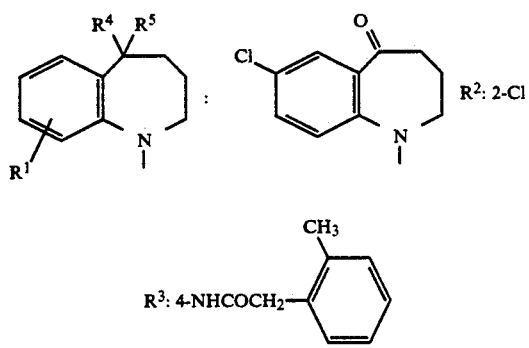

Crystalline form: Colorless amorphous.
Form: Free.
NMR analysis: 27).

EXAMPLE 53

Structure:

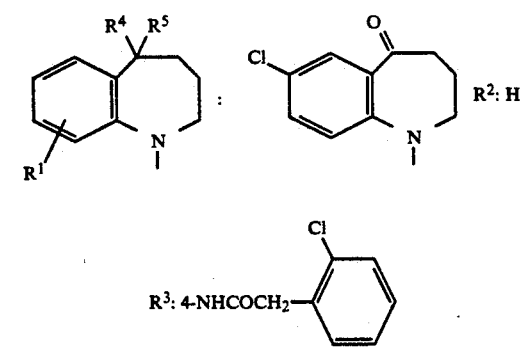

Crystalline form: White powder.
Recrystallization solvent: methanol/diethyl ether.
Melting point: 199°–202° C.
Form: Free.

EXAMPLE 54

Structure:

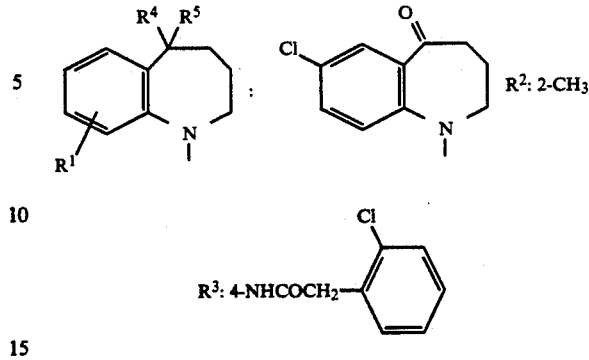

Crystalline form: White powder.
Recrystallization solvent: Methanol/diethyl ether.
Melting point: 171°–172° C.
Form: Free.

EXAMPLE 55

Structure:

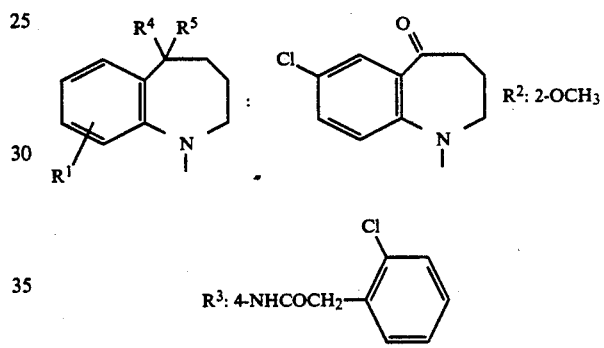

Crystalline form: White powder.
Recrystallization solvent: Methanol/diethyl ether.
Melting point: 243.5°–245° C.
Form: Free.

EXAMPLE 56

Structure:

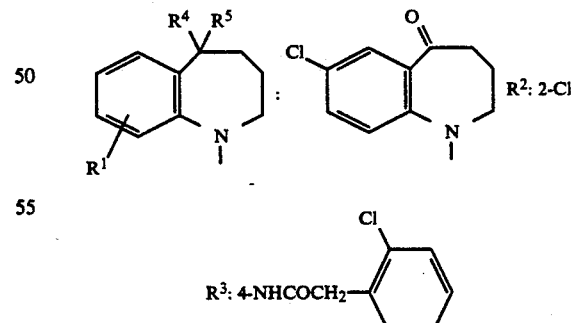

Crystalline form: White powder.
Recrystallization solvent: Methanol/diethyl ether.
Melting point: 162°–163° C.
Form: Free.

EXAMPLE 57

Structure

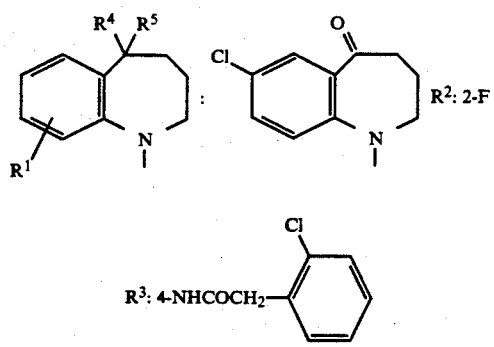

R²: 2-F

R³: 4-NHCOCH₂—(2-Cl-phenyl)

Crystalline form: White powder.
Recrystallization solvent: Methanol/diethyl ether.
Melting point: b 162°–163° C.
Form: Free

EXAMPLE 58
Structure:

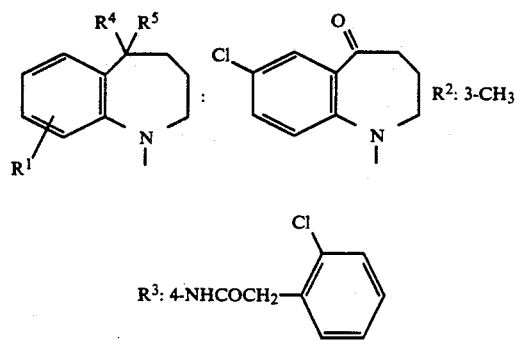

R²: 3-CH₃

R³: 4-NHCOCH₂—(2-Cl-phenyl)

Crystalline form: White powder.
Recrystallization solvent: methanol/diethyl ether.
Melting point: 134°–135° C.
Form: Free.

EXAMPLE 59
Structure:

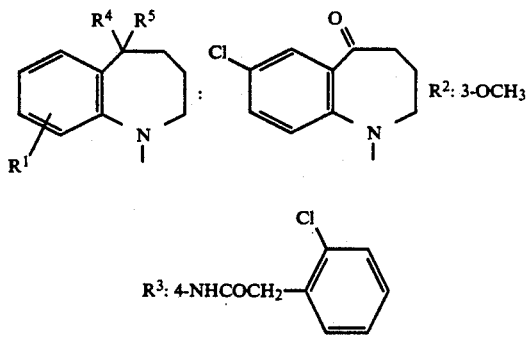

R²: 3-OCH₃

R³: 4-NHCOCH₂—(2-Cl-phenyl)

Crystalline form: White powder.
Recrystallization solvent: methanol/diethyl ether.
Melting point: 177°–178° C.
Form: Free.

EXAMPLE 60
Structure:

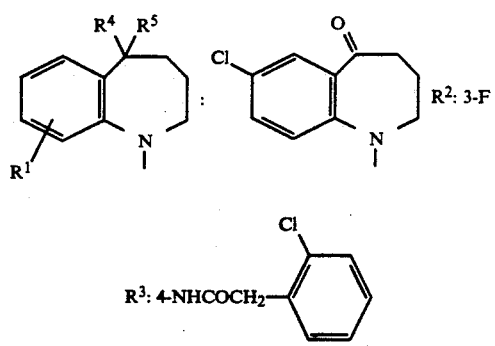

R²: 3-F

R³: 4-NHCOCH₂—(2-Cl-phenyl)

Crystalline form: White powder.
Recrystallization solvent: Methanol/diethyl ether.
Melting point: 168°–169° C.
Form: Free.

EXAMPLE 61
Structure:

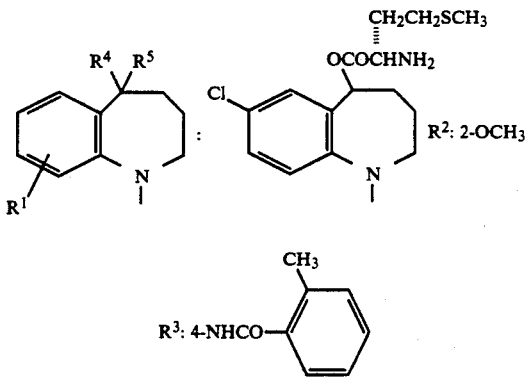

R²: 2-OCH₃

R³: 4-NHCO—(2-CH₃-phenyl)

Crystalline form: Colorless amorphous.
Form: Free.
NMR analysis: 28).

EXAMPLE 62 I
Structure:

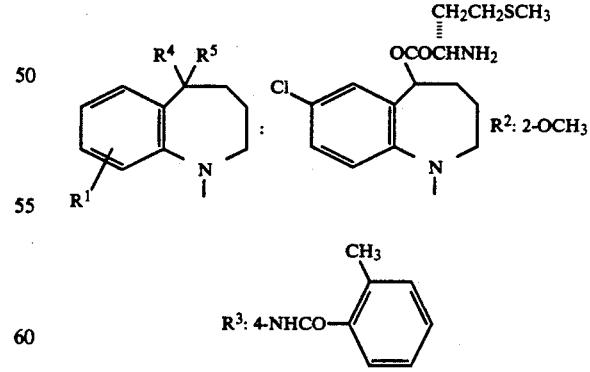

R²: 2-OCH₃

R³: 4-NHCO—(2-CH₃-phenyl)

Crystalline form: Colorless amorphous.
Form: Free.
NMR analysis: 29).

EXAMPLE 63
Structure:

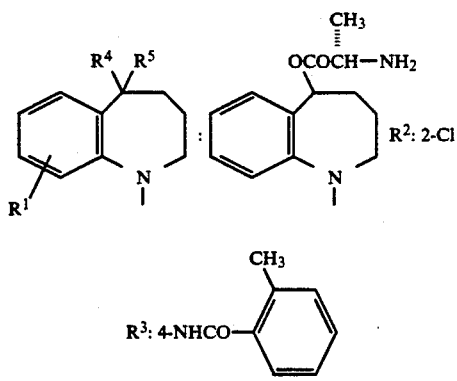

R³: 4-NHCO-(o-tolyl)

Crystalline form: Colorless amorphous.
Form: Free.
NMR analysis: 30).

EXAMPLE 64

Structure:

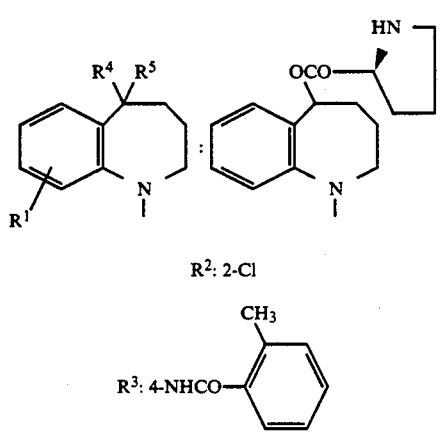

R²: 2-Cl

R³: 4-NHCO-(o-tolyl)

Crystalline form: Colorless amorphous.
Form: Free.
NMR analysis: 31).

EXAMPLE 65

Structure:

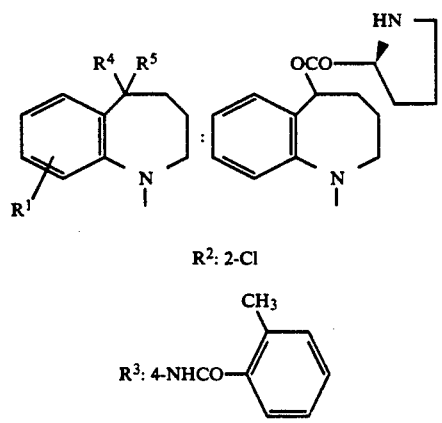

R²: 2-Cl

R³: 4-NHCO-(o-tolyl)

Crystalline form: Colorless amorphous.
Form: Free.
NMR analysis: 32).

EXAMPLE 66

Structure:

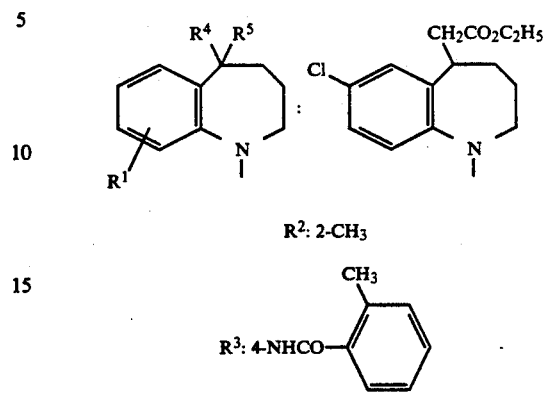

R²: 2-CH₃

R³: 4-NHCO-(o-tolyl)

Crystalline form: Colorless amorphous.
Form: Free.
NMR analysis: 33).

EXAMPLE 67

Structure:

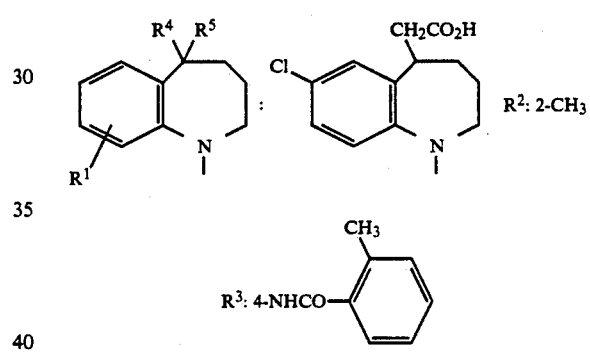

R²: 2-CH₃

R³: 4-NHCO-(o-tolyl)

Crystalline form: Colorless amorphous.
Form: Free.
NMR analysis: 34).

EXAMPLE 68

Structure:

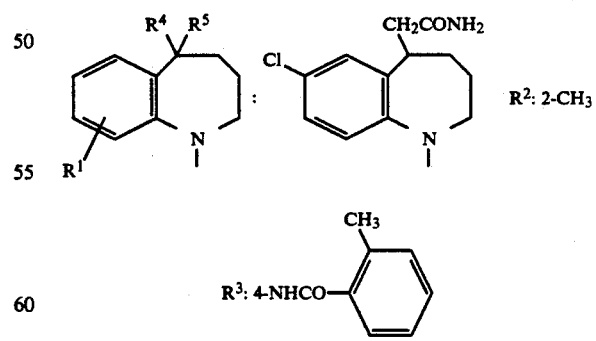

R²: 2-CH₃

R³: 4-NHCO-(o-tolyl)

Crystalline form: Colorless amorphous.
Form: Free.
NMR analysis: 35).

EXAMPLE 69

Structure:

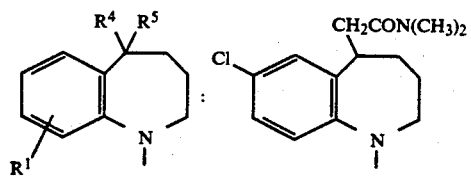

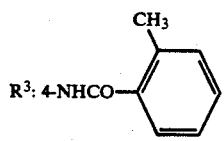

R²: 2-CH₃

Crystalline form: Colorless amorphous.
Form: Free.
NMR analysis: 36).

EXAMPLE 70

Structure:

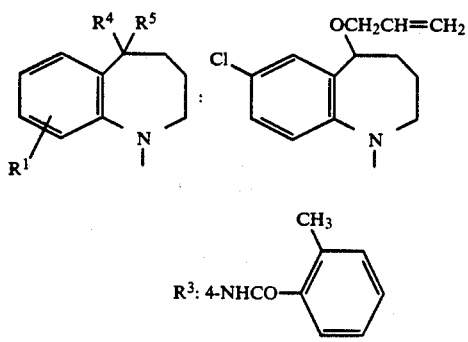

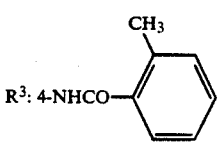

Crystalline form: Colorless amorphous.

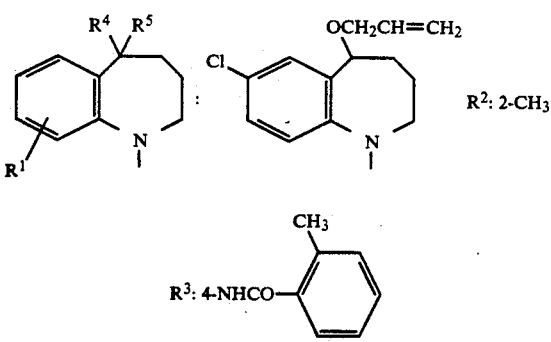

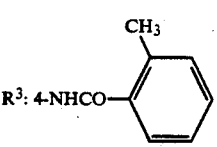

Crystalline form: Colorless amorphous.
Form: Free.
NMR analysis: 37).

EXAMPLE 71

Structure:

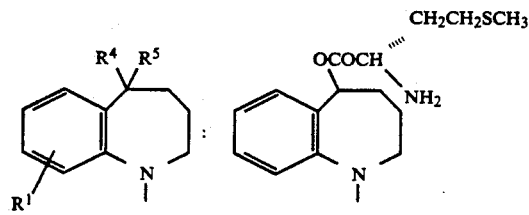

-continued

R²: 2-Cl

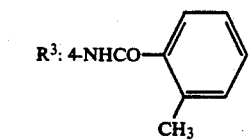

Crystalline form: Colorless amorphous.
Form: Free.
NMR analysis: 38).

EXAMPLE 72 1

Structure:

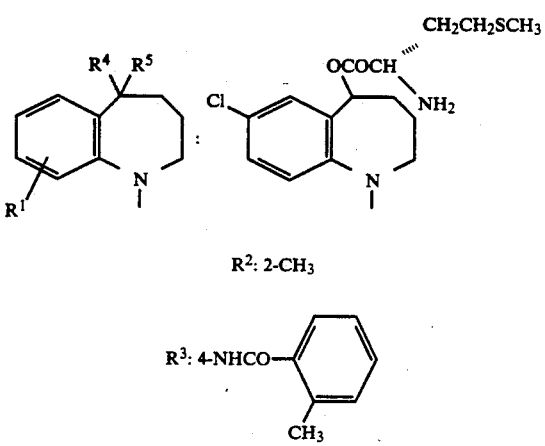

R²: 2-CH₃

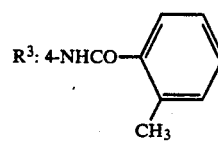

Crystalline form: Colorless amorphous.
Form: Free.
NMR analysis: 39).

EXAMPLE 73

Structure:

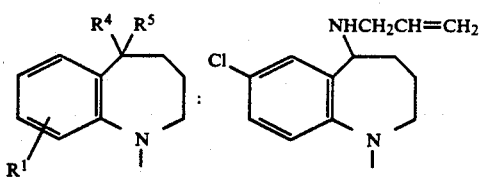

R²: H

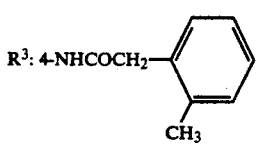

Crystalline form: White powder.
Recrystallization solvent: Methanol/diethyl ether.
Melting point: 128°–130° C.
Form: Free.

EXAMPLE 74

Structure:

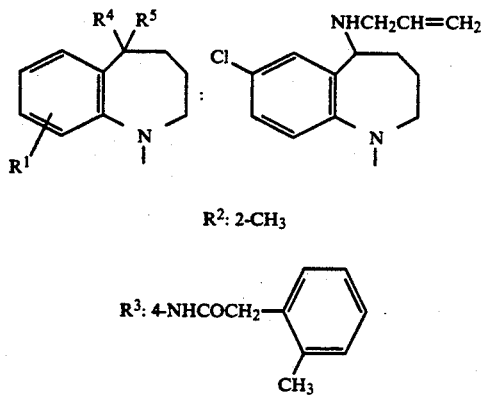

R²: 2-CH₃

R³: 4-NHCOCH₂-（2-methylphenyl）

Crystalline form: White powder.
Recrystallization solvent: Methanol/diethyl ether.
Melting point: 139°-140° C.
Form: Free.

EXAMPLE 75

Structure:

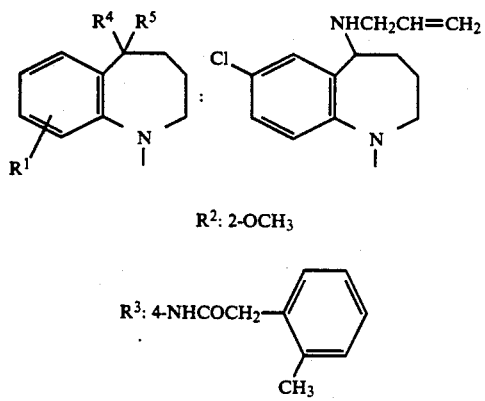

R²: 2-OCH₃

R³: 4-NHCOCH₂-（2-methylphenyl）

Crystalline form: Colorless amorphous.
Form: Free.
NMR analysis: 40).

EXAMPLE 76

Structure:

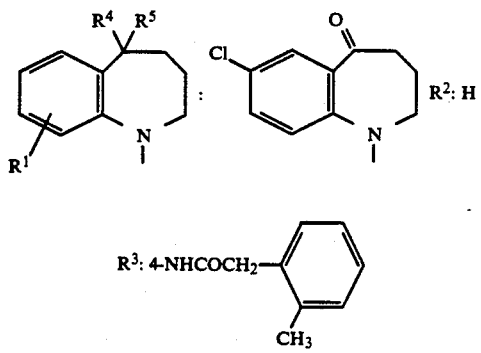

R³: 4-NHCOCH₂-（2-methylphenyl）

Crystalline form: White powder.
Recrystallization solvent: Methanol/diethyl ether.
Melting point: 194°-196° C.
Form: Free.

EXAMPLE 77

Structure:

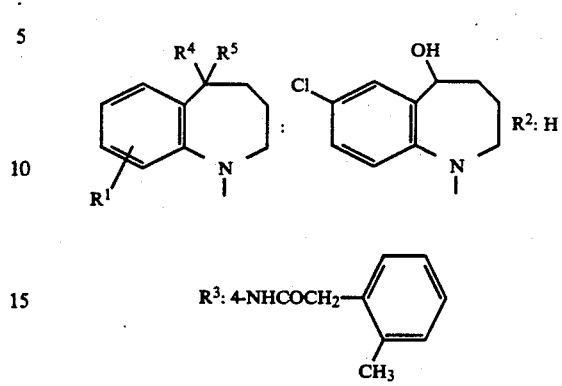

R²: H

R³: 4-NHCOCH₂-（2-methylphenyl）

Crystalline form: White powder.
Recrystallization solvent: methanol/diethyl ether.
Melting point: 241°-243° C.
Form: Free.

EXAMPLE 78

Structure:

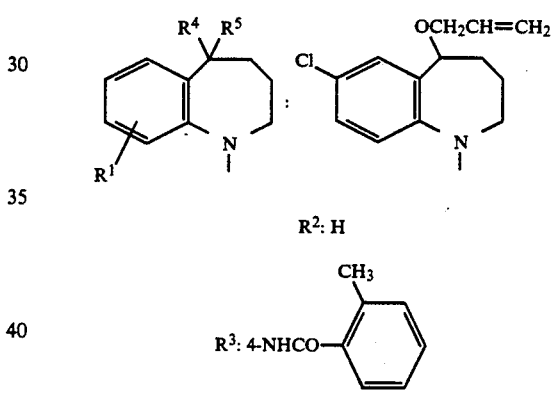

R²: H

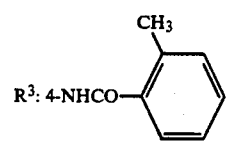

R³: 4-NHCO-（2-methylphenyl）

Crystalline form: White powder.
Recrystallization solvent: Dichloromethane/diethyl ether.
Melting point: 129.5°-131.5° C.
Form: Free.

EXAMPLE 79

Structure:

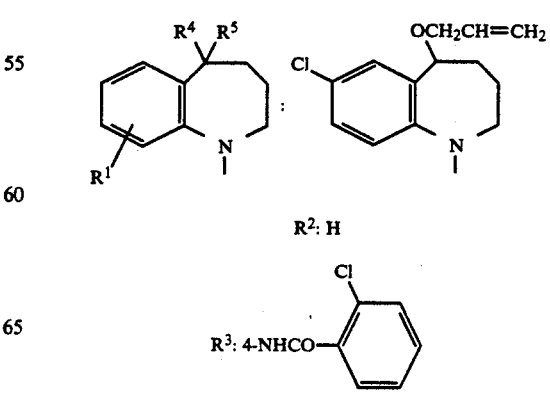

R²: H

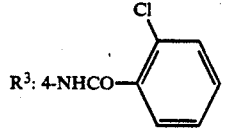

R³: 4-NHCO-（2-chlorophenyl）

Crystalline form: White powder.
Recrystallization solvent: Dichloromethane/diethyl ether.
Melting point: 136°–138° C.
Form: Free.

EXAMPLE 80
Structure:

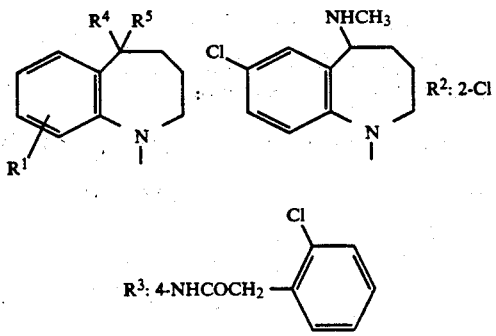

Crystalline form: White powder.
Recrystallization solvent: Methanol/diethyl ether.
Melting point: 178°–179° C.
Form: Free.

EXAMPLE 81
Structure:

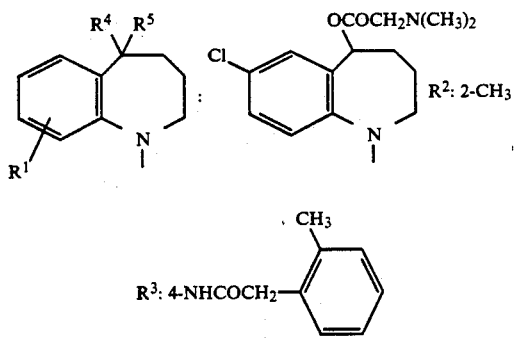

Crystalline form: Colorless amorphous.
Form: Free.
NMR analysis: 41).

EXAMPLE 82
Structure:

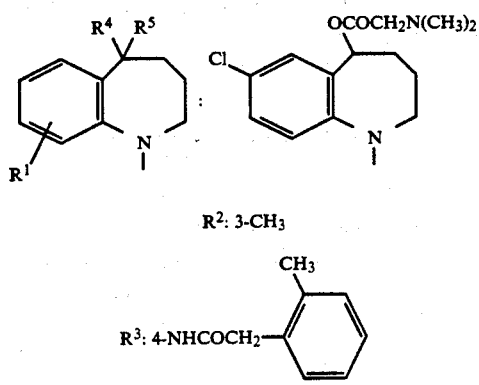

Crystalline form: Colorless amorphous.
Form: Free.
NMR analysis: 42).

EXAMPLE 83
Structure:

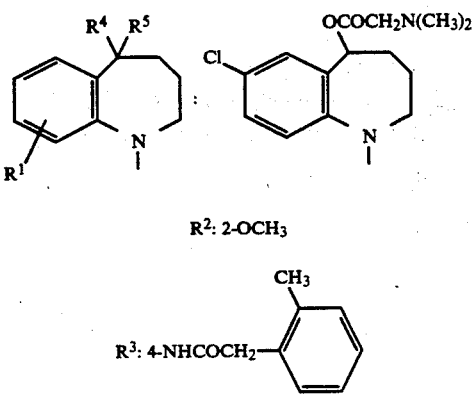

Crystalline form: Colorless amorphous.
Form: Free.
NMR analysis: 43).

EXAMPLE 84
Structure:

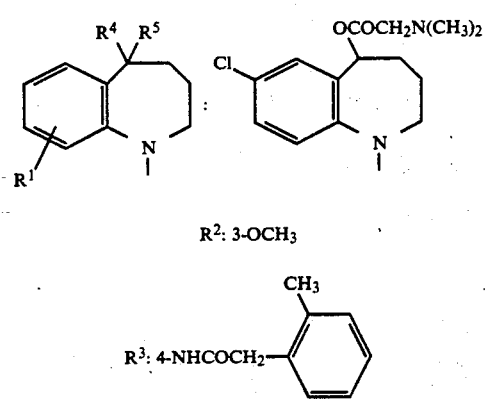

Crystalline form: Colorless amorphous.
Form: Free.
NMR analysis: 44).

EXAMPLE 85
Structure:

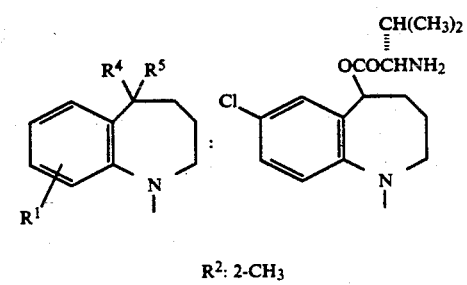

-continued

R³: 4-NHCO— 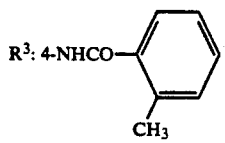
CH₃

Crystalline form: Colorless amorphous.
Form: Free.
NMR analysis: 45).

1) ¹H-NMR (CDCl₃) δ; 1.41–1.72 (2H, m), 1.86–2.13 (1H, m), 2.19–2.48 (1H, m), 2.64–3.18 (4H, m), 4.20–4.83 (2H, m), 6.44–7.10 (3H, m), 7.17–8.15 (7H, m), 9.32 (1H, brs), 9.91 (1H, s), 10.72 (1H, s)

2) ¹H-NMR (CDCl₃) δ; 1.40–3.20 (11H, m), 3.27–5.05 (2H, m), 6.38–8.37 (11H, m).

3) ¹H-NMR (CDCl₃) δ; 1.40–3.30 (14H, m), 3.30–5.20 (2H, m), 6.70–8.60 (11H, m).

4) ¹H-NMR (CDCl₃) δ; 1.47–5.16 (7H, m), 6.30–8.23 (11H, m), 8.90–9.10 (1H, m), 10.10–10.55 (1H, m).

5) ¹H-NMR (DMSO-d₆) δ; 1.30–5 28 (9H, m), 6.19–8.13 (11H, m), 9.44–9.60 (1H, m), 10.56–10.94 (1H, m).

6) ¹H-NMR (CDCl₃) δ; 1.46–5.10 (21H, m), 6.43–8.44 (11H, m).

7) ¹H-NMR (CDCl₃) δ; 1.00–2.55 (10H, m), 2.33 (3H, s), 2.57–3.14 (1H, m), 3.39–3.78 (1H, m), 3.61 (2H, s), 3.84–5.20 (1H, m), 6.40–7.71 (12H, m)

8) ¹H-NMR (CDCl₃) δ; 1.05–2.57 (10H, m), 2.35 (3H, s), 2.57–3.15 (1H, m), 3.30–3.82 (1H, m), 3.63 (2H, s), 3.89–5.19 (1H, m), 6.42–7.70 (12H, m).

9) ¹H-NMR (CDCl₃) δ; 1.10–3.18 (11H, m), 3.32–3.80 (1H, m), 3.57 (2H, s), 3.95–5.20 (1H, m), 6.43–7.68 (12H, m), 8.13–8.44 (1H, m).

10) ¹H-NMR (CDCl₃) δ; 1.06–3.21 (11H, m), 3.31–3.90 (1H, m), 3.54 (2H, s), 3.90–5.18 (1H, m), 6.38–7.65 (12H, m), 8.26–8.62 (1H, m).

11) ¹H-NMR (CDCl₃) δ; 1.10–3.14 (11H, m), 3.34–3.75 (1H, m), 3.65 (2H, s), 3.89 (3H, s), 3.95–5.20 (1H, m), 6.45–7.70 (12H, m), 7.72–8.05 (1H, m).

12) ¹H-NMR (CDCl₃) δ; 1.09–3.16 (11H, m), 3.35–5.20 (2H, m), 3.61 (2H, s), 3.78 (3H, s), 6.38–7.64 (12H, m), 7.70 (1H, s).

13) ¹H-NMR (CDCl₃) δ; 1.10–3.25 (11H, m), 3.36–3.71 (3H, m), 3.75–3.90 (3H, m), 3.95–5.20 (1H, m), 6.42–7.68 (12H, m).

14) ¹H-NMR (CDCl₃) δ; 1.08–3.21 (11H, m), 3.36–3.79 (1H, m), 3.59 (2H, s), 3.91–5.19 (1H, m), 6.45–7.65 (12H, m), 8.04–8.35 (1H, m).

15) ¹H-NMR (CDCl₃) δ; 1.08–3.20 (11H, m), 3.34–3.79 (1H, m), 3.58 (2H, s), 3.90–5.19 (1H, m), 6.43–7.65 (12H, m), 7.91–8.20 (1H, m).

16) ¹H-NMR (CDCl₃) δ; 1.11–3.13 (11H, m), 3.35–3.72 (1H, m), 3.61 (2H, s), 3.86 (3H, s), 3.88 (3H, s), 3.94–5.20 (1H, m), 6.45–7.69 (11H, m).

17) ¹H-NMR (CDCl₃) δ; 1.10–3.27 (11H, m), 3.36–3.75 (1H, m), 3.49 (2H, s), 3.90–5.20 (1H, m), 6.41–7.84 (11H, m), 8.81–9.59 (1H, m).

18) ¹H-NMR (CDCl₃) δ; 1.10–3.20 (11H, m), 3.35–3.66 (1H, m), 3.73 (2H, s), 3.91–5.20 (1H, m), 6.48–7.65 (11H, m), 7.68–7.94 (1H, m).

19) ¹H-NMR (CDCl₃) δ; 1.08–3.21 (11H, m), 3.38–3.68 (1H, m), 4.00 (2H, s), 3.95–5.20 (1H, m), 6.45–7.70 (11H, m), 8.15 (1H, s).

20) ¹H-NMR (CDCl₃) δ; 1.08–3.25 (11H, m), 3.36–3.69 (1H, m), 3.91 (2H, s), 3.88–5.20 (1H, m), 6.45–7.72 (11H, m), 7.85–8.13 (1H, m), 8.85 (1H, s).

21) ¹H-NMR (CDCl₃) δ; 1.10–3.30 (11H, m), 3.39–3.95 (3H, m), 3.9–5.20 (1H, m), 6.45–7.82 (10H, m), 7.94–8.36 (2H, m), 8.82–9.17 (1H, m).

22) ¹H-NMR (CDCl₃) δ; 1.06–3.11 (11H, m), 3.35–3.70 (1H, m), 3.62 (2H, s), 3.74 (3H, s), 3.86 (3H, s), 3.92–5.20 (1H, m), 6.45–7.67 (11H, m), 7.81–8.16 (1H, m).

23) ¹H-NMR (CDCl₃) δ; 1.04–5.10 (17H, m), 5.96–6.17 (1H, m), 6.52–7.86 (11H, m).

24) ¹H-NMR (CDCl₃) δ; 1.41–1.89 (2H, m), 1.90–2.24 (2H, m), 2.31 (3H, s), 2.47–2.89 (2H, m), 3.45 (3H, s), 3.69 (2H, s), 4.57–5.13 (2H, m), 6.39–6.76 (2H, m), 6.78–6.95 (1H, m), 6.95–7.41 (7H, m), 7.41–7.65 (1H, m).

25) ¹H-NMR (CDCl₃) δ; 1.45–1.92 (2H, m), 1.92–2.28 (2H, m), 2.50–2.96 (2H, m), 3.45 (3H, s), 3.81 (2H, s), 4.64–5.20 (2H, m), 6.28–7.12 (3H, m), 7.13–7.50 (5H, m), 7.50–7.64 (1H, m), 7.65–7.99 (1H, m).

26) ¹H-NMR (CDCl₃) δ; 1.52–2.54 (2H, m), 2.27 (3H, s), 2.70–2.98 (2H, m), 2.98–5.52 (2H, m), 3.65 (2H, s), 6.56–6.87 (1H, m), 6.97–7.43 (8H, m), 7.78 (1H, d, J=2.4 Hz), 7.91–8.15 (1H, m).

27) ¹H-NMR (CDCl₃) δ; 1.76–2.40 (2H, m), 2.29 (3H, s), 2.86 (2H, t, J=6.0 Hz), 3.00–5.32 (2H, m), 3.69 (2H, s), 6.46–8.05 (10H, m).

28) ¹H-NMR (CDCl₃) δ; 1.47–2.92, 3.44–4.11 (total 21H, m), 4.66–5.12 (1H, m), 5.85–6.30 (1H, m), 6.61–8.10 (11H, m).

$[α]_D^{24} = +90°$ (methanol, c=0.2) (measured as hydrochloride).

29) ¹H-NMR (CDCl₃) δ; 1.48–2.88, 3.45–4.09 (total 21H, m), 4.60–5.05 (1H, m), 5.85–6.31 (1H, m), 6.62–7.78 (10H, m), 7.92–8.41 (1H, m).

$[α]_D^{24} = -107°$ (methanol, c=0.2) (measured as hydrochloride).

30) ¹H-NMR (CDCl₃) δ; 1.21–3.06, 3.40–3.87 (total 14H, m), 4.54–5.05 (1H, m), 5.88–6.22 (1H, m), 6.83–8.09, 8.33–8.59, 8.82–9.03 (total 12H, m).

$[α]_D^{24} = +90°$ C. (methanol, c=0.2) (measured as hydrochloride).

31) ¹H-NMR (CDCl₃) δ; 1.50–3.22, 3.54–3.99 (total 16H, m), 4.41–4.90 (1H, m), 5.88–6.22 (1H, m), 6.79–8.04 (11H, m), 9.05–9.63 (1H, m).

$[α]_D^{24} = +54°$ (methanol, c=0.2) (measured as hydrochloride).

32) ¹H-NMR (CDCl₃) 4 ; 1.51–4.12 (16H, m), 4.60–5.17 (1H, m), 5.89–5.29 (1H, m), 6.71–8.50, 9.85–10.36 (total 12H, m).

$[α]_D^{24} = -68°$ (methanol, c=0.2) (measured as hydrochloride).

33) ¹H-NMR (CDCl₃) δ; 1.04–4.63 (20H, m), 6.42–7.74 (11H, m).

34) ¹H-NMR (DMSO-d₆) δ; 1.08–2.23 (4H, m), 2.23–2.55 (6H, m), 2.55–3.00 (3H, m), 3.00–5.10 (3H, m), 6.68–7.90 (10H, m), 10.13–10.50 (1H, m).

35) ¹H-NMR (CDCl₃) δ; 1.49–2.43 (3H, m), 2.43–2.61 (6H, m), 2.61–2.92 (2H, m), 2.92–3.99 (3H, m), 4.48–4.97 (1H, m), 5.80 (1H, brs), 6.44 (1H, brs), 6.53–7.83 (11H, m).

36) ¹H-NMR (CDCl₃) δ; 1.43–2.38 (3H, m), 2.38–2.77 (8H, m), 2.77–3.33 (8H, m), 3.33–5.10 (2H, m), 6.36–8.04 (11H, m).

37) ¹H-NMR (CDCl₃) δ; 1.43–2.13 (2H, m), 2.13–2.63 (7H, m), 2.63–3.75 (2H, m), 3.75–4.82 (4H, m), 4.97–5.50 (2H, m), 5.83–6.15 (1H, m), 6.51–7.73 (11H, m).

38) Isomer A: Colorless amorphous.
¹H-NMR (CDCl₃) δ; 0.95–4.18, 4.61–5.18 (total 19H, m), 5.85–6.29 (1H, m), 6.90–8.35 (12H, m).
Isomer B: Colorless amorphous.

¹H-NMR (CDCl₃) δ; 0.94–4.33, 4.61–5.23 (total 19H, m), 5.84–6.28 (1H, m), 6.76–7.91 (11H, m), 9.25–9.76 (1H, m).

39)

Isomer A: Colorless amorphous.

¹H-NMR (CDCl₃) δ; 1.46–2.98, 3.22–4.05 (total 21H, m), 4.67–5.19 (1H, m), 5.79–6.22 (1H, m), 6.50–7.81 (11H, m).

$[\alpha]_D^{24}$ = +112° (methanol, c=0.2) (measured as hydrochloride).

Isomer B: Colorless amorphous.

¹H-NMR (CDCl₃) δ; 1.42–2.98, 3.30–4.01 (total 21H, m), 4.58–5.20 (1H, m), 5.85–6.21 (1H, m), 6.43–8.14 (11H, m).

$[\alpha]_D^{24}$ = −143° (methanol, c=0.2) (measured as hydrochloride).

40) ¹H-NMR (CDCl₃) δ; 1.30–2.30 (4H, m), 2.31 (3H, s), 2.95–3.54 (3H, m), 2.71 (2H, s), 2.80–4.60 (2H, m), 5.01–5.39 (2H, m), 5.70–6.05 (1H, m), 6.41–6.63 (1H, m), 6.80–7.43 (9H, m), 7.50–7.67 (1H, m).

41) ¹H-NMR (CDCl₃) δ; 1.49–1.97 (2H, m), 2.02–2.30 (2H, m), 2.30–2.61 (12H, m), 2.68–2.95 (1H, m), 3.11–3.49 (2H, m), 3.62–3.86 (2H, m), 4.68–5.15 (1H, m), 5.90–6.19 (1H, m), 6.41–6.60 (1H, m), 6.60–7.02 (3H, m), 7.05–7.40 (6H, m), 7.40–7.52 (1H, m).

42) ¹H-NMR (CDCl₃) δ; 1.55–1.94 (2H, m), 1.95–2.59 (14H, m), 2.60–2.91 (1H, m), 2.91–3.47 (2H, m), 3.75 (2H, s), 4.60–5.20 (1H, m), 5.90–6.22 (1H, m), 6.40–6.66 (1H, m), 6.72–7.41 (9H, m), 7.77–8.04 (1H, m).

43) ¹H-NMR (CDCl₃) δ; 1.53–1.94 (2H, m), 2.00–2.25 (2H, m), 2.25–2.52 (9H, m), 2.58–2.92 (1H, m), 3.07–3.41 (2H, m), 3.53 (3H, s), 3.60–3.91 (2H, m), 4.66–5.13 (1H, m), 6.39–7.55 (10H, m), 7.60–7.80 (1H, m).

44) ¹H-NMR (CDCl₃) δ; 1.62–1.98 (2H, m), 1.98–2.58 (11H, m), 2.64–2.98 (1H, m), 2.99–3.44 (2H, m), 3.44–3.60 (3H, m), 3.72 (2H, s), 4.60–5.21 (1H, m), 5.91–6.28 (1H, m), 6.44–7.10 (4H, m), 7.10–7.49 (5H, m), 7.72 (1H, s), 8.00–8.36 (1H, m).

45) Isomer A: Colorless amorphous.

¹H-NMR (CDCl₃) δ; 0.67–3.62, 4.67–5.20 (total 22H, m), 5.87–6.31 (1H, m), 6.49–7.85 (11H, m)

$[\alpha]_D^{24}$ = −133° (methanol, c=0.2) (measured as hydrochloride).

Isomer B: Colorless amorphous.

¹H-NMR (CDCl₃) δ; 0.81–3.65, 4.65–5.18 (total 22H, m), 5.86–6.28 (1H, m), 6.44–8.03 (11H, m).

$[\alpha]_D^{24}$ = +126° (methanol, c=0.2) (measured as hydrochloride).

EXAMPLE 86

To tetrahydrofuran (200 ml) is added sodium hydride (60%, 0.85 g), and thereto is added dropwise ethyl diethylphosphonoacetate (4.68 ml) with stirring under ice-cooling, and the mixture is further stirred under ice-cooling for 10 minutes. To the reaction mixture is added 5-oxo-7-chloro-1-[2-methyl-4-(2-methylbenzoylamino)benzoyl]-2,3,4,5-tetrahydro-¹H-benzazepine (2.10 g), and the mixture is stirred at room temperature for 6 hours. The reaction solution is poured into ice-water (200 ml), and extracted with ethyl acetate (300 ml). The extract is washed with brine (300 ml), dried over magnesium sulfate, and the solvent is distilled off. The resulting residue is purified by silica gel column chromatography (eluent; ethyl acetate: n-hexane=1:2) to give 5-ethoxycarbonylmethylidene-7-chloro-1-[2-methyl-4-(2-methylbenzoylamino)benzoyl]-2,3,4,5-tetrahydro-¹H-benzazepine (2.22 g) in the form of a mixture of the E-type compound and the Z-type compound thereof, as colorless amorphous.

¹H-NMR (CDCl₃) δ; 1.04–5.10 (17H, m), 5.96–6.17 (1H, m), 6.52–7.86 (11H, m).

EXAMPLE 87

5-Ethoxycarbonylmethylidene-7-chloro-1-[2-methyl-4-(2-methylbenzoylamino)benzoyl]-2,3,4,5-tetrahydro-¹H-benzazepine (0.30 g) and nickel chloride hexahydrate (0.55 g) are dissolved in a mixture of tetrahydrofuran/methanol (1:1) (30 ml), and to the mixture is added slowly sodium borohydride (0.26 g) with stirring under ice-cooling, and then the mixture is further stirred for 10 minutes under ice-cooling. The insoluble materials are filtered with Celite, and the filtrate is concentrated. The resulting residue is purified by silica gel column chromatography (eluent; ethyl acetate:n-hexane=1:1) to give 5-ethoxycarbonylmethyl-7-chloro-1-[2-methyl-4-(2-methylbenzoylamino)benzoyl]-2,3,4,5-tetrahydro-¹H-benzazepine (0.13 g) as colorless amorphous.

¹H-NMR (CDCl₃) δ; 1.04–4.63 (20H, m), 6.42–7.74 (11H, m).

EXAMPLE 88

To a solution of 5-hydroxy-7-chloro-1-[2-methyl-4-(2-methylbenzoylamino)benzoyl]-2,3,4,5-tetrahydro-¹H-benzazepine (1.0 g), dimethylaminopyridine (1.26 g) and dimethylaminopyridine hydrochloride (1.10 g) in chloroform (20 ml) are added N-benzyloxycarbonyl-L-valine (672 mg) and dicyclohexylcarbodiimide (1.42 g), and the mixture is stirred at room temperature for 7 hours. To the mixture are added methanol (3 ml) and acetic acid (0.7 ml), and the mixture is stirred at room temperature for 30 minutes. The insoluble materials are removed by filtration, and to the filtrate is added 5% aqueous sodium hydrogen sulfate solution, and further extracted with dichloromethane. The extract is washed successively with saturated aqueous sodium hydrogen carbonate solution and saturated brine, dried over magnesium sulfate, and the solvent is distilled off under reduced pressure to give crude 5-N-benzyloxycarbonyl-L-valyloxy-7-chloro-1-[2-methyl-4-(2-methylbenzoylamino)-benzoyl]-2,3,4,5-tetrahydro-¹H-benzazepine (2.0 g). This product is dissolved in a mixture of acetic acid (15 ml) and ethyl acetate (15 ml), and thereto is added 5% Pd-C (0.3 g). The mixture is subjected to hydrogenation at ordinary room temperature under atmospheric pressure. After hydrogenation, the catalyst is removed by filtration, and the filtrate is concentrated. The resulting residue is purified by silica gel column chromatography (eluent; ethyl acetate) to give Isomer A (0.48 g) and Isomer B (0.47 g) of 5-L-valyloxy-7-chloro-1-[2-methyl-4-(2-methylbenzoylamino)-benzoyl]-2,3,4,5-tetrahydro-¹H-benzazepine.

Isomer A:

Rf value: 0.3 (developer; ethyl acetate:methanol=10:1).

¹H-NMR (CDCl₃) δ; 0.67–3.62, 4.67–5.20 (total 22H, m), 5.87–6.31 (1H, m), 6.49–7.85 (11H, m).

$[\alpha]_D^{24}$ = −133° (methanol, c=0.2) (measured as hydrochloride).

Isomer B:

Rf value: 0.4 (developer; ethyl acetate:methanol=10:1).

¹H-NMR (CDCl₃) δ; 0.81–3.65, 4.65–5.18 (total 22H, m), 5.86–6.28 (1H, m), 6.44–8.03 (11H, m).

[α$_D^{24}$ = +126° (methanol, c=0.2) (measured as hydrochloride).

EXAMPLE 89

A uniform solution of 5-(N-tert-butoxycarbonyl-L-methionyloxy)-7-chloro-1-[2-methoxy-4-(2-methylbenzoylamino)benzoyl]-2,3,4,5-tetrahydro-1H-benzazepine (1.27 g), trifluoroacetic acid (2.5 ml) and anisole (0.6 ml) is stirred at room temperature for 2 hours. The trifluoroacetic acid is almost distilled off under reduced pressure, and the residue is acidified with an 0.2 N aqueous sodium hydroxide solution, and the mixture is extracted with dichloromethane. The dichloromethane layer is washed with water, dried over magnesium sulfate and concentrated. The resulting residue is purified by silica gel column chromatography (eluent; ethyl acetate) to give Isomer A (0.34 g) and Isomer B (0.35 g) of 5-(L-methionyloxy)-7-chloro-1-[2-methoxy-4-(2-methylbenzoylamino)benzoyl]-2,3,4,5-tetrahydro-1H-benzazepine.

Isomer A: Colorless amorphous
Rf value: 0.5 (developer; ethyl acetate:methanol=10:1).
$^1$H-NMR (CDCl$_3$) δ; 1.47–2.92, 3.44–4.11 (total 21H, m), 4.66–5.12 (1H, m), 5.85–6.30 (1H, m), 6.61–8.10 (11H, m).
[α]$_D^{24}$: +96° (methanol, c=0.2) (measured as hydrochloride).

Isomer B: Colorless amorphous,
Rf value: 0.4 (developer; ethyl acetate:methanol=10:1).
$^1$H-NMR (CDCl$_3$) δ; 1.48–2.88, 3.45–4.09 (total 21H, m), 4.60–5.05 (1H, m), 5.85–6.31 (1H, m), 6.62–7.78 (10H, m), 7.92–8.41 (1H, m).
[α]$_D^{24}$: −107° (methanol, c=0.2) (measured as hydrochloride).

EXAMPLES 90-203

Using the appropriate starting compounds, the compounds of Table 2 are obtained in the same manner as in Examples 1 and 2.

TABLE 2

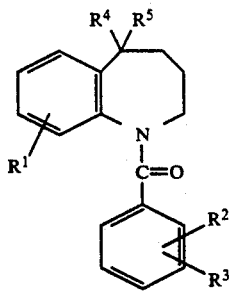

EXAMPLE 90

Structure:

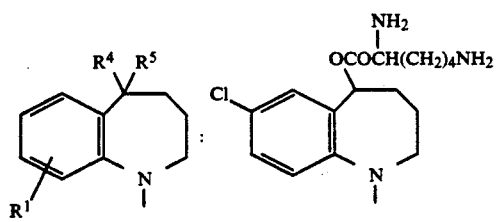

-continued
R$^2$: 2-OCH$_3$

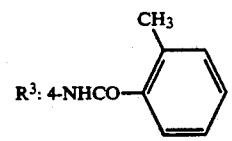
R$^3$: 4-NHCO—

Crystalline form: Colorless amorphous.
Form: Dihydrochloride.
NMR analysis: 46).

EXAMPLE 91

Structure:

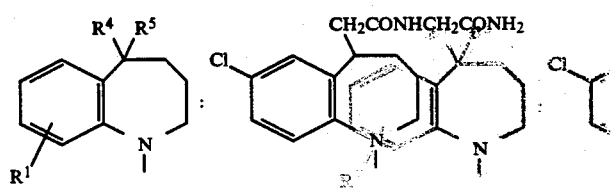

R$^2$: 2-CH$_3$

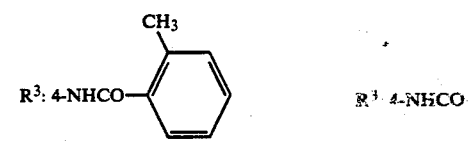
R$^3$: 4-NHCO—

Crystalline form: Colorless amorphous.
Form: Free.
NMR analysis: 144).

EXAMPLE 92

Structure:

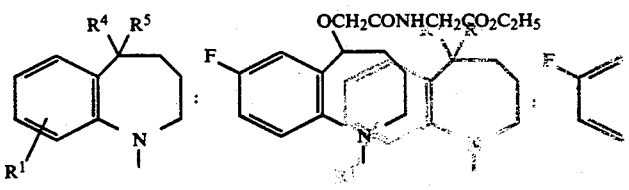

R$^2$: 2-Cl

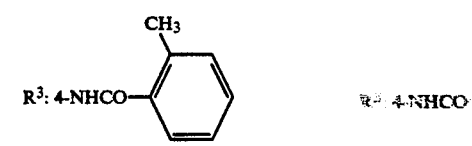
R$^3$: 4-NHCO—

Crystalline form: Colorless amorphous.
Form: Free.
NMR analysis: 47).

EXAMPLE 93

Structure:

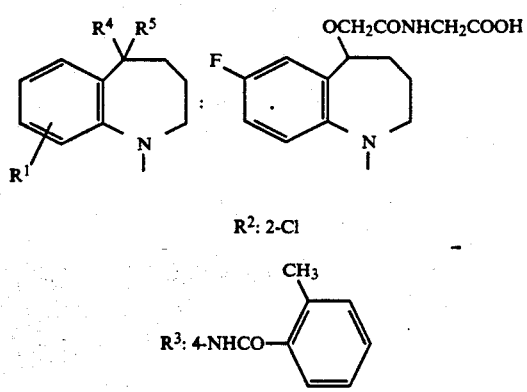

R²: 2-Cl

R³: 4-NHCO-(2-methylphenyl)

Crystalline form: colorless amorphous.
Form: Free.
NMR analysis: 48).

EXAMPLE 94

Structure:

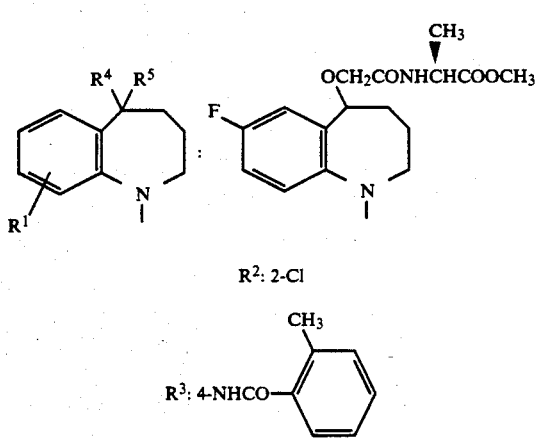

R²: 2-Cl

R³: 4-NHCO-(2-methylphenyl)

Crystalline form: colorless amorphous.
Form: Free.
NMR analysis: 49).

EXAMPLE 95

Structure:

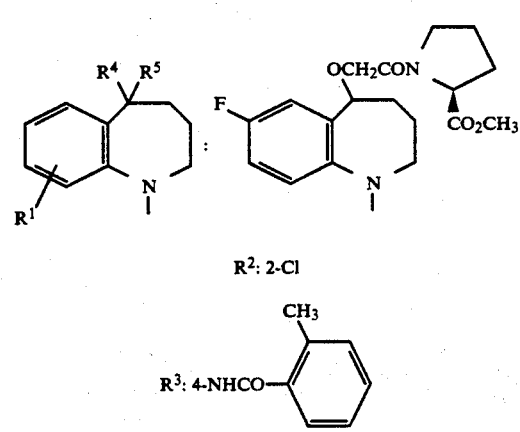

R²: 2-Cl

R³: 4-NHCO-(2-methylphenyl)

Crystalline form: Slightly yellow amorphous.
Form: Free.
NMR analysis: 50).

EXAMPLE 96

Structure:

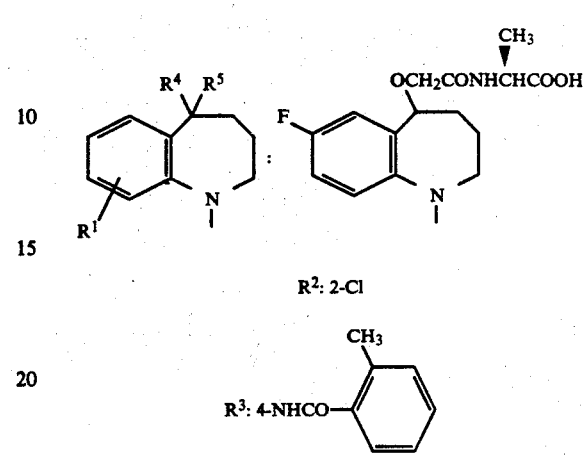

R²: 2-Cl

R³: 4-NHCO-(2-methylphenyl)

Crystalline form: Slightly yellow amorphous.
Form: Free.
NMR analysis: 51).

EXAMPLE 97

Structure:

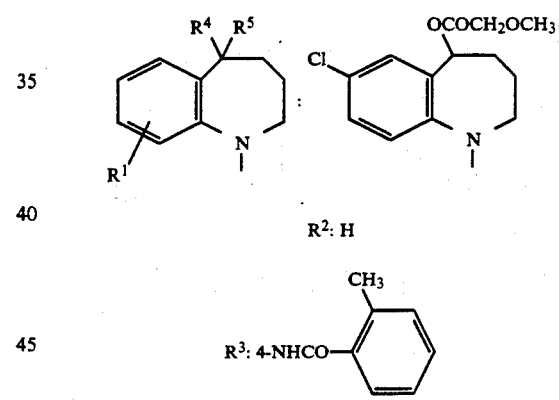

R²: H

R³: 4-NHCO-(2-methylphenyl)

Crystalline form: White powder.
Recrystallization solvent: Dichloromethane/diethyl ether.
Melting point: 149°–152° C.
Form: Free.

EXAMPLE 98

Structure:

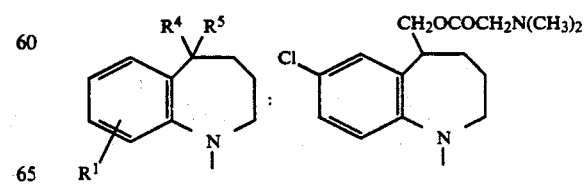

R²: H

-continued

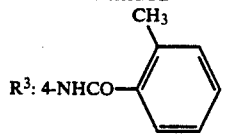

Crystalline form: Colorless amorphous.
Form: Hydrochloride.
NMR analysis: 96).

EXAMPLE 99

Structure:

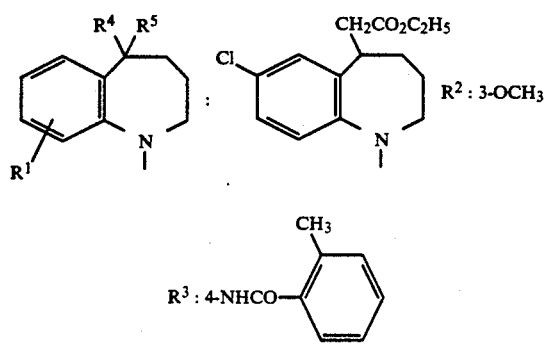

Crystalline form: Colorless amorphous.
Form: Free.
NMR analysis: 52).

EXAMPLE 100

Structure:

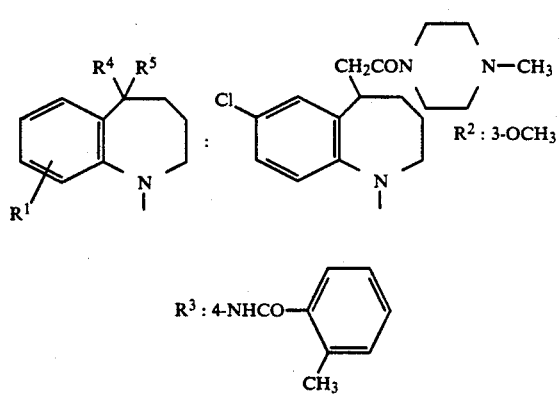

Crystalline form: Colorless needles.
Recrystallization solvent: Ethanol/diethylether/n-hexane.
Melting point: 182°-184° C.
Form: Free.

EXAMPLE 101

Structure:

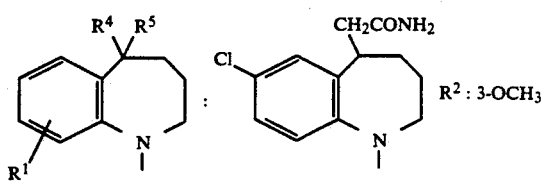

-continued

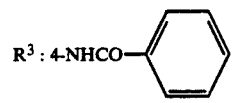

Crystalline form: Colorless amorphous.
Form: Free.
NMR analysis: 53).

EXAMPLE 102

Structure:

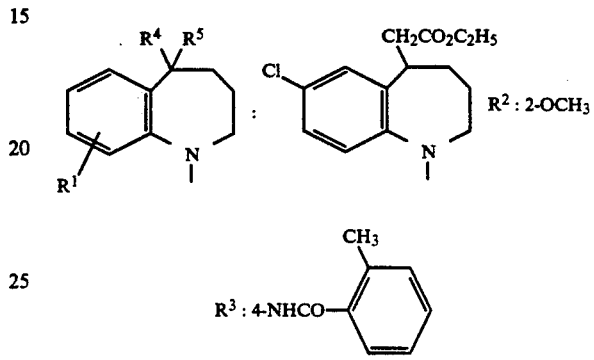

Crystalline form: Colorless prisms.
Recrystallization solvent: Ethanol.
Melting point: 191°-193° C.
Form: Free.

EXAMPLE 103

Structure:

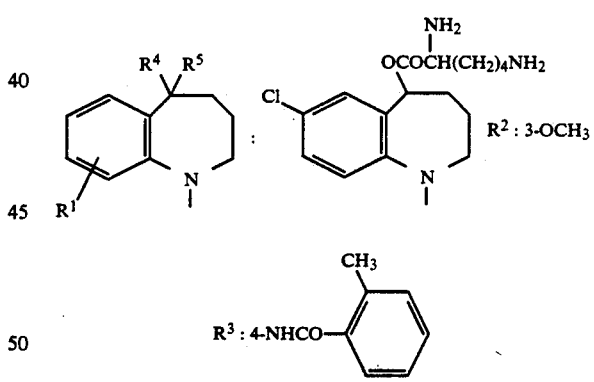

Crystalline form: Colorless amorphous.
Form: Dihydrochloride.
NMR analysis: 131).

EXAMPLE 104

Structure:

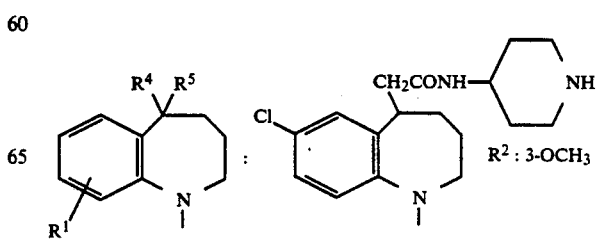

EXAMPLE 105

Structure:

R³: 4-NHCO-(2-CH₃-phenyl)

Substituent: CH₂CO₂H, R²: 2-OCH₃, 7-Cl

Crystalline form: White powder.
Recrystallization solvent: Ethyl acetate.
Melting point: 243.5°–244.5° C.
Form: Free.

EXAMPLE 106

Structure:

R³: 4-NHCO-(2-CH₃-phenyl)

Substituent: CH₂CON(CH₃)₂, R²: 3-OCH₃, 7-Cl

Crystalline form: Colorless needles.
Recrystallization solvent: Ethanol/diethyl ether.
Melting point: 164°–166° C.
Form: Free.

EXAMPLE 107

Structure:

Substituent: HO-, R²: H (R³: 4-NHCO-(2-CH₃-phenyl) — previous page continued: Crystalline form: Colorless amorphous. Form: Hydrochloride. NMR analysis: 54).)

Crystalline form: Colorless prisms.
Form: Free.
NMR analysis: 132).

EXAMPLE 108

Structure:

R³: 4-NHCO-(2-CH₃-phenyl), R²: H

Substituent: CH₃CO₂CH₂O-

Crystalline form: Colorless needles.
Recrystallization solvent: Methanol/diethyl ether.
Melting point: 141°–144° C.
Form: Free.

EXAMPLE 109

Structure:

R³: 4-NHCO-(2-CH₃-phenyl)

Substituent: =CH-CH₂-N(CH₃)₂, R²: 2-Cl, 7-F

Crystalline form: Yellow amorphous.
Form: Hydrochloride.
NMR analysis: 55).

EXAMPLE 110

Structure:

Substituent: =CH-CH₂-N(CH₃)₂, R²: 2-Cl, 7-F

-continued

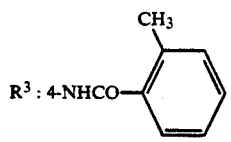

Crystalline form: Yellow amorphous.
Form: Hydrochloride.
NMR analysis: 56).

EXAMPLE 111

Structure:

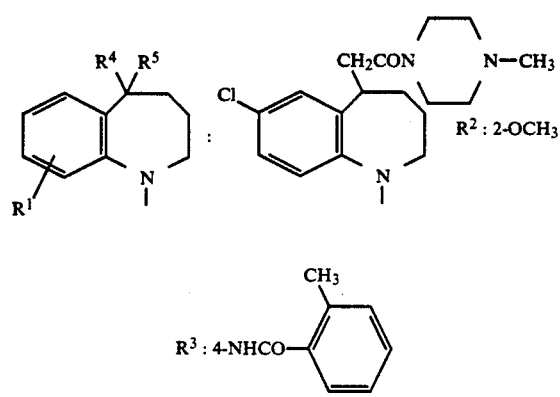

Crystalline form: Colorless amorphous.
Form: Hydrochloride.
NMR analysis: 57).

EXAMPLE 112

Structure:

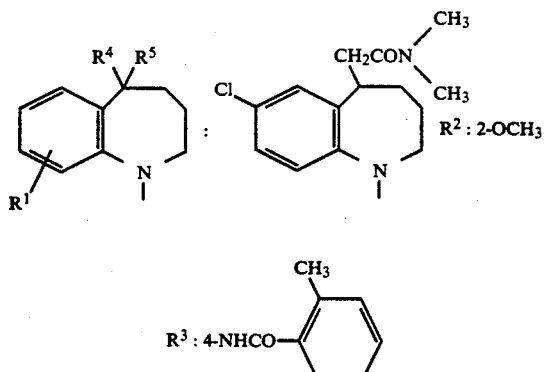

Crystalline form: Colorless amorphous.
Form: Free.
NMR analysis: 58).

EXAMPLE 113

Structure:

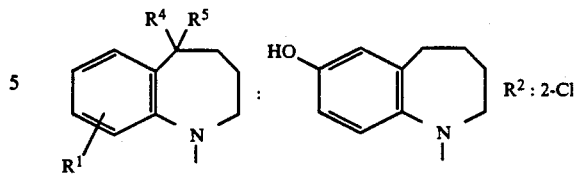

Crystalline form: White powder.
Recrystallization solvent: Ethanol/diethyl ether.
Melting point: 254°–258° C.
Form: free.

EXAMPLE 114

Structure:

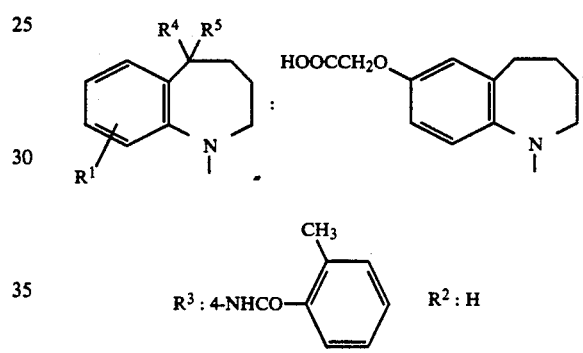

Crystalline form: White powder.
Recrystallization solvent: Ethanol.
Melting point: 258°–261° C.
Form: Free.

EXAMPLE 115

Structure:

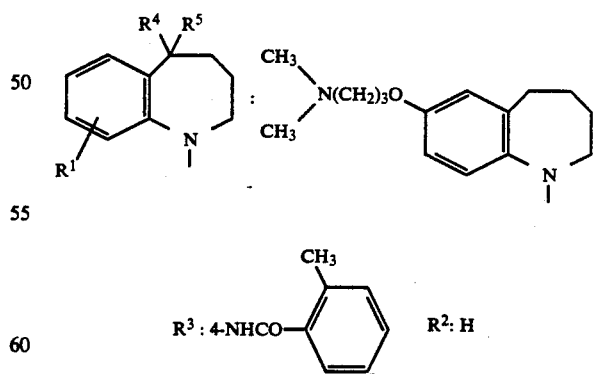

Crystalline form: Colorless amorphous.
Form: Free.
NMR analysis: 133).

EXAMPLE 116

Structure:

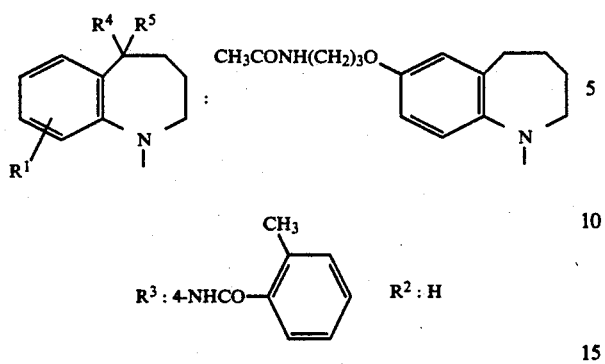

Crystalline form: Colorless amorphous.
Form: Free.
NMR analysis: 134).

EXAMPLE 117

Structure:

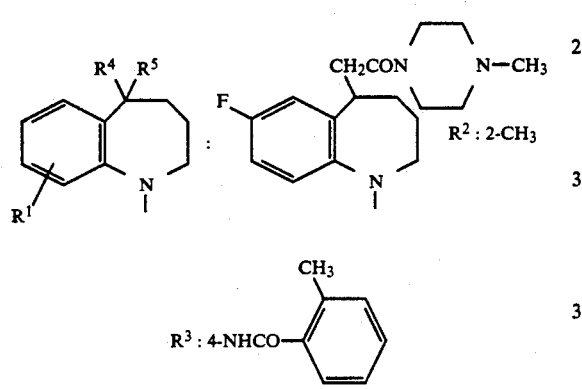

Crystalline form: colorless amorphous.
Form: Free.
NMR analysis: 108).

EXAMPLE 118

Structure:

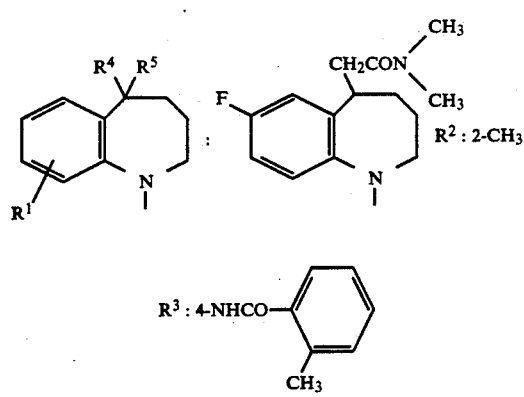

Crystalline form: Colorless amorphous.
Form: Free.
NMR analysis: 109).

EXAMPLE 119

Structure:

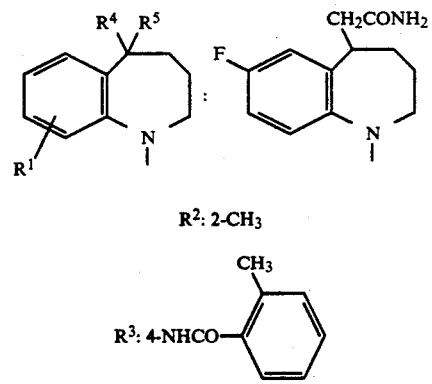

Crystalline form: White powder.
Recrystallization solvent: Ethanol/water.
Melting point: 260°–263° C. (decomposed).
Form: Free.

EXAMPLE 120

Structure:

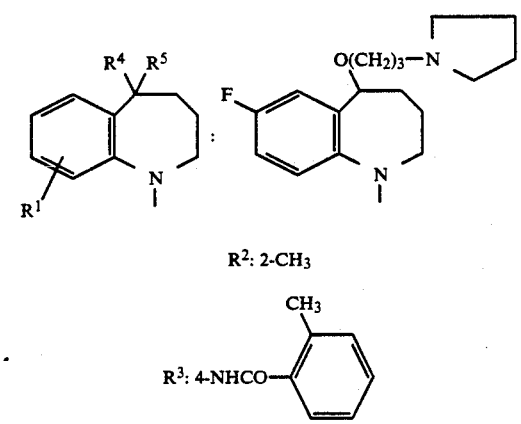

Crystalline form: Colorless amorphous.
Form: Free.
NMR analysis: 110).

EXAMPLE 121

Structure:

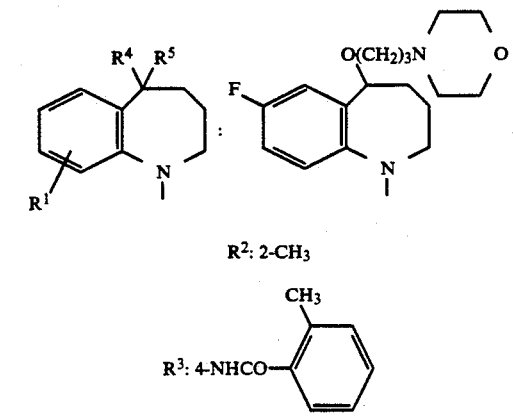

Crystalline form: Colorless amorphous.

EXAMPLE 122

Structure:

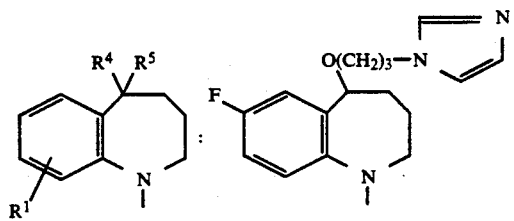

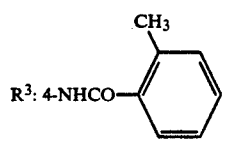

Crystalline form: Colorless amorphous.
Form: Free.
NMR analysis: 112).

EXAMPLE 123

Structure:

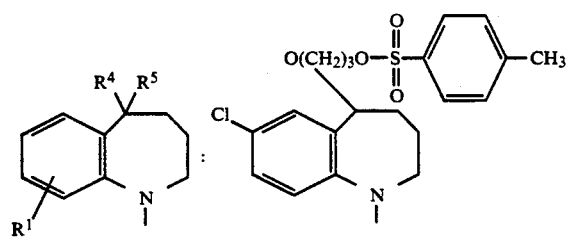

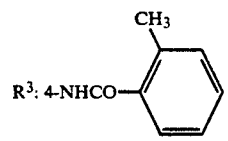

Crystalline form: Colorless amorphous.
Form: Free.
NMR analysis: 59).

EXAMPLE 124

Structure:

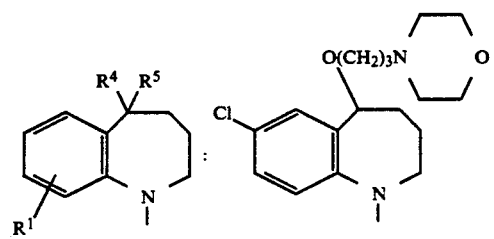

-continued $R^3$: 4-NHCO—⟨CH₃ phenyl⟩

Crystalline form: Pale yellow amorphous.
Form: Hydrochloride.
NMR analysis: 60).

EXAMPLE 125

Structure:

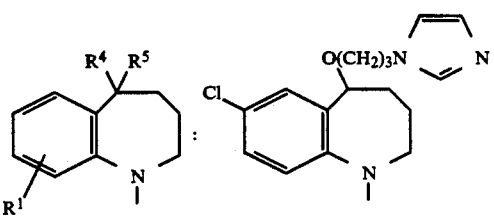

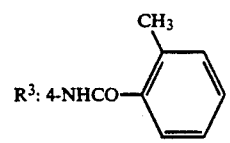

Crystalline form: Colorless amorphous.
Form: Hydrochloride.
NMR analysis: 61).

EXAMPLE 126

Structure:

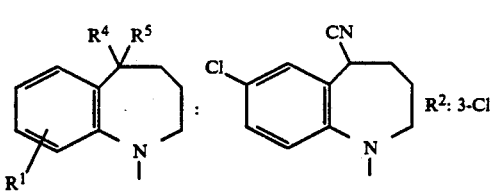

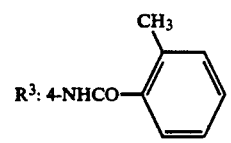

Crystalline form: Colorless prisms.
Recrystallization solvent: Ethanol/dichloromethane.
Melting point: 213°–215.5° C.
Form: Free.

EXAMPLE 127

Structure:

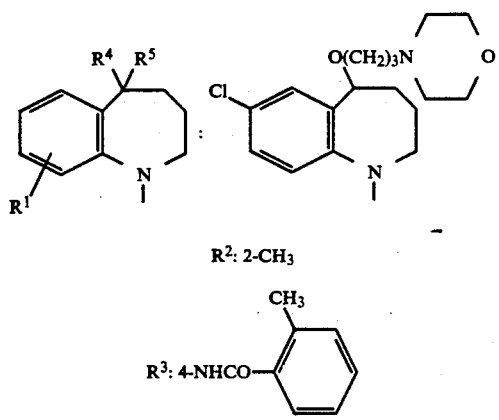

R²: 2-CH₃

R³: 4-NHCO-(2-CH₃-phenyl)

Crystalline form: Colorless amorphous.
Form: Hydrochloride.
NMR analysis: 62).

EXAMPLE 128

Structure:

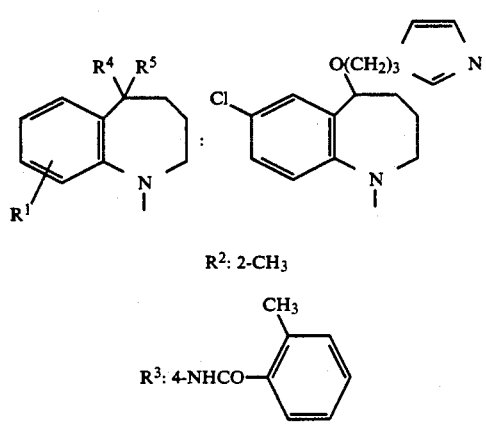

R²: 2-CH₃

R³: 4-NHCO-(2-CH₃-phenyl)

Crystalline form: Colorless amorphous.
Form: dihydrochloride.
NMR analysis: 63).

EXAMPLE 129

Structure:

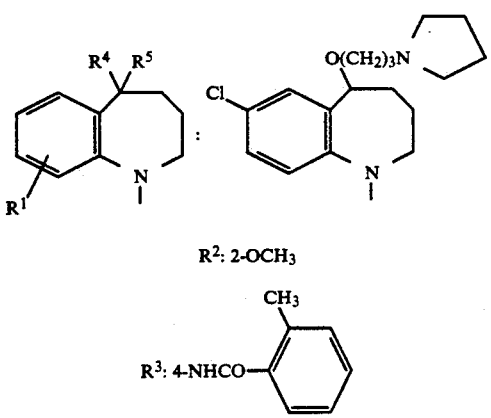

R²: 2-OCH₃

R³: 4-NHCO-(2-CH₃-phenyl)

Crystalline form: Pale yellow amorphous.

Form: Hydrochloride.
NMR analysis: 64).

EXAMPLE 130

Structure:

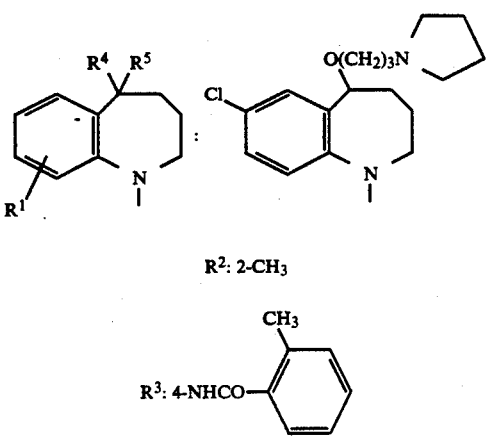

R²: 2-CH₃

R³: 4-NHCO-(2-CH₃-phenyl)

Crystalline form: Slightly yellow amorphous.
Form: Hydrochloride.
NMR analysis: 65).

EXAMPLE 131

Structure:

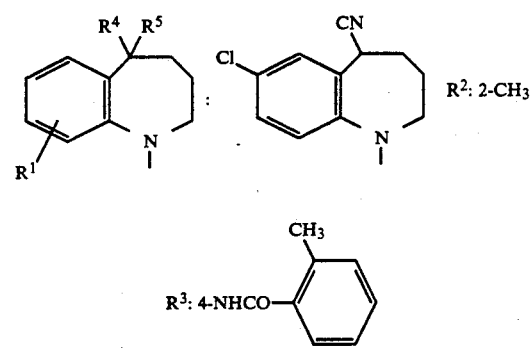

R²: 2-CH₃

R³: 4-NHCO-(2-CH₃-phenyl)

Crystaline form: Colorless amorphous.
Form: Free.
NMR analysis: 66).

EXAMPLE 132

Structure:

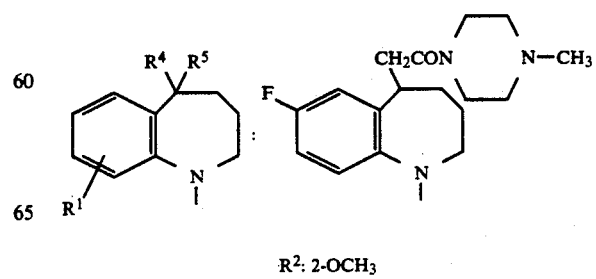

R²: 2-OCH₃

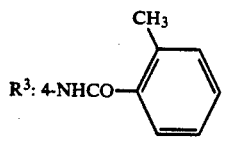

Crystalline form: Colorless amorphous.
Form: Free.
NMR analysis: 116).

EXAMPLE 133

Structure:

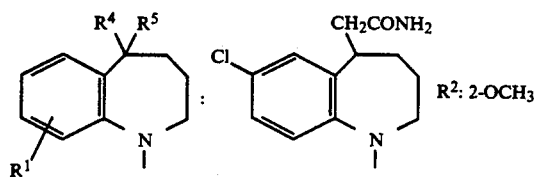

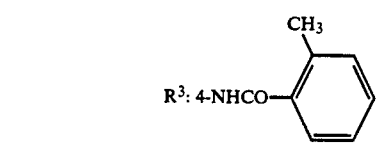

Crystalline form: Colorless needles.
Recrystallization solvent: Dichloromethane/methanol.
Melting point: 202.5°–203.5° C.
Form: Free.

EXAMPLE 134

Structure:

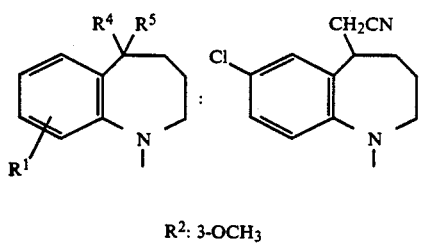

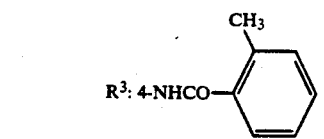

Crystaline form: Colorless needles.
Recrystallization solvent: Ethyl acetate/diethyl ether.
Melting point: 164°–167° C.
Form: Free.

EXAMPLE 135

Structure:

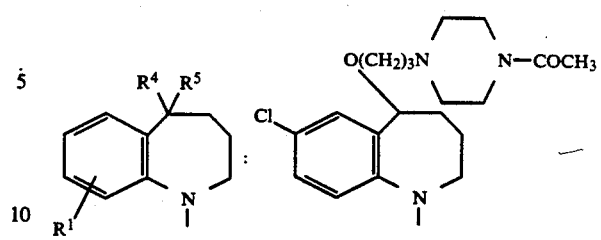

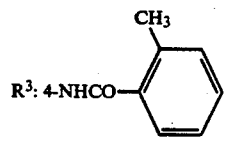

Crystalline form: Pale yellow amorphous.
Form: Hydrochloride.
NMR analysis: 67).

EXAMPLE 136

Structure:

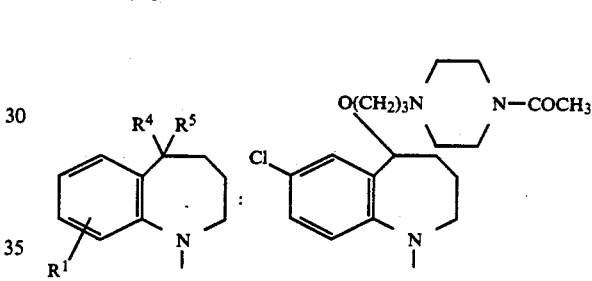

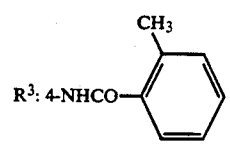

Crystalline form: Colorless amorphous.
Form: Hydrochloride.
NMR analysis: 68).

EXAMPLE 137

Structure:

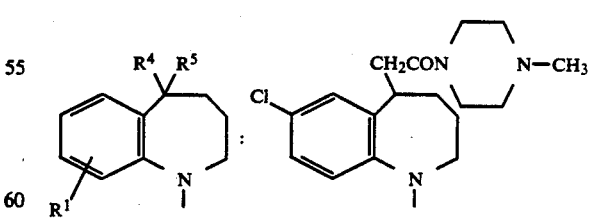

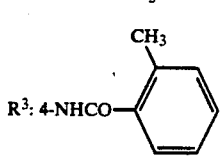

Crystalline form: colorless amorphous.
Form: Hydrochloride.
NMR analysis: 69).

EXAMPLE 138

Structure:

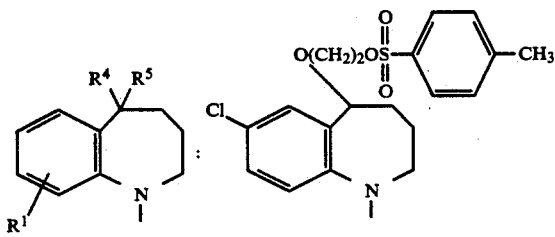

R$_2$: 2-OCH$_3$

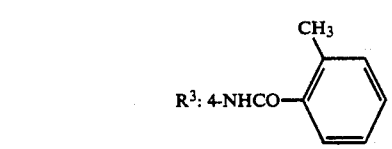

R$^3$: 4-NHCO—

Crystalline form: Colorless amorphous.
Form: Free.
NMR analysis: 70).

EXAMPLE 139

Structure:

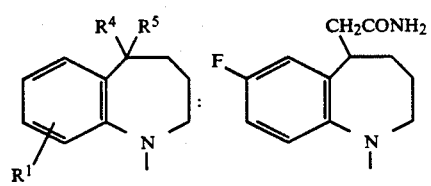

R$_2$: 2-OCH$_3$

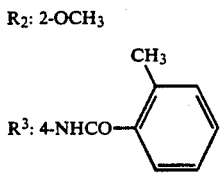

R$^3$: 4-NHCO—

Crystalline form: White powder.
Recrystallization solvent: Ethanol/water.
Melting point: 260°–261° C.
Form: Free.

EXAMPLE 140

Structure:

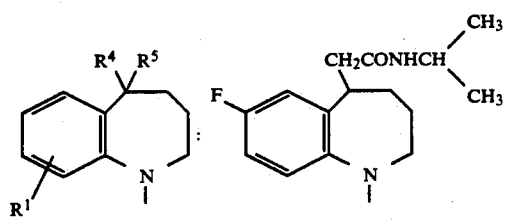

-continued
R$_2$: 2-OCH$_3$

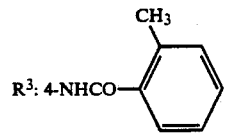

R$^3$: 4-NHCO—

Crystaline form: colorless amorphous.
Form: Free.
NMR analysis: 113).

EXAMPLE 141

Structure:

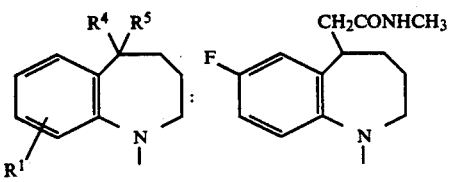

R$_2$: 2-OCH$_3$

R$^3$: 4-NHCO—

Crystalline form: Colorless amorphous.
Form: Free.
NMR analysis: 114).

EXAMPLE 142

Structure:

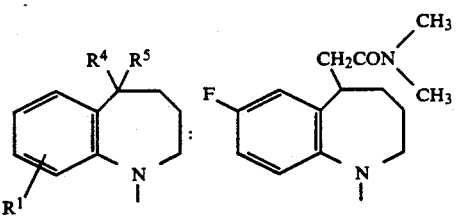

R$_2$: 2-OCH$_3$

R$^3$: 4-NHCO—

Crystaline form: Colorless amorphous.
Form: Free.
NMR analysis: 115).

EXAMPLE 143

Structure:

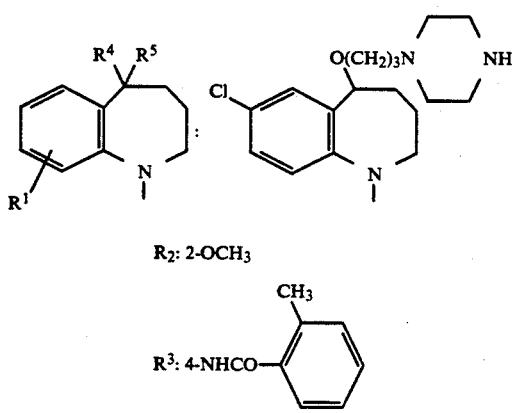

R₂: 2-OCH₃

R³: 4-NHCO-C₆H₄-CH₃ (o-tolyl)

Crystalline form: Colorless amorphous.
Form: Dihydrochloride.
NMR analysis: 71).

EXAMPLE b 144

Structure:

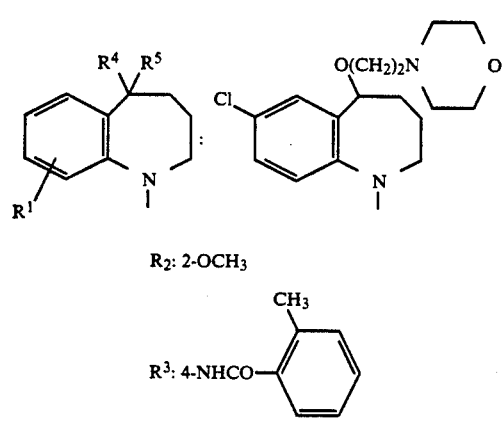

R₂: 2-OCH₃

R³: 4-NHCO-C₆H₄-CH₃ (o-tolyl)

Crystalline form: Colorless amorphous.
Form: Hydrochloride.
NMR analysis: 72).

EXAMPLE 145

Structure:

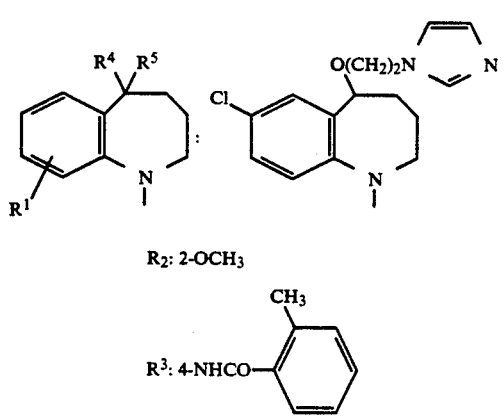

R₂: 2-OCH₃

R³: 4-NHCO-C₆H₄-CH₃ (o-tolyl)

Crystalline form: Colorless amorphous.
Form: Hydrochloride.
NMR analysis: 73).

EXAMPLE 146

Structure:

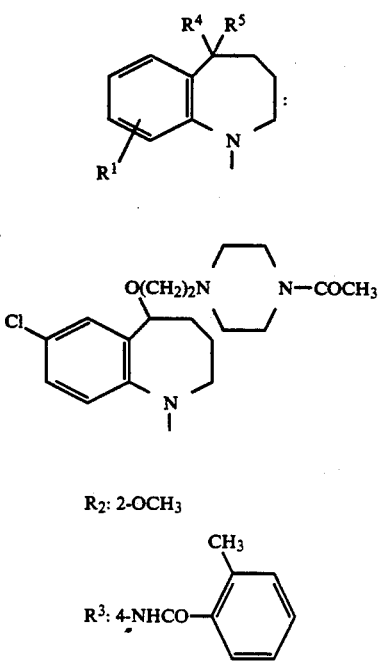

R₂: 2-OCH₃

R³: 4-NHCO-C₆H₄-CH₃ (o-tolyl)

Crystalline form: Pale yellow amorphous.
Form: Hydrochloride.
NMR analysis: 74).

EXAMPLE 147

Structure:

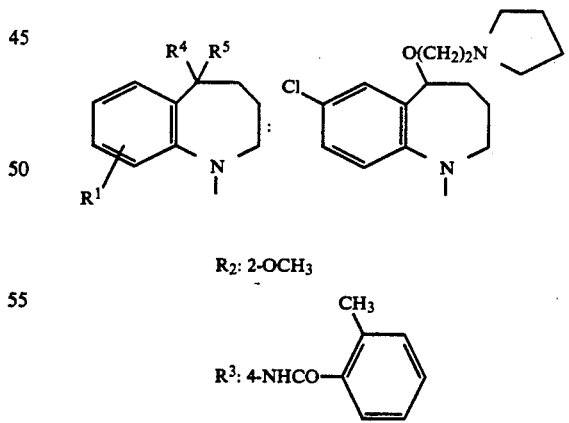

R₂: 2-OCH₃

R³: 4-NHCO-C₆H₄-CH₃ (o-tolyl)

Crystalline form: Pale yellow amorphous.
Form: Hydrochloride.
NMR analysis: 75).

EXAMPLE 148

Structure:

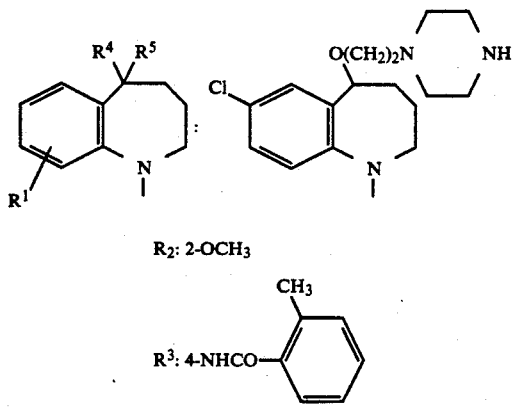

R₂: 2-OCH₃

R³: 4-NHCO-

Crystalline form: Colorless amorphous.
Form: Dihydrochloride.
NMR analysis: 76).

EXAMPLE 149

Structure:

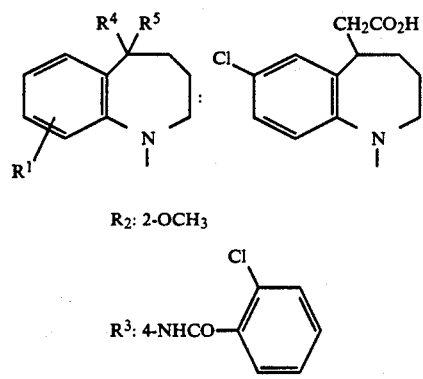

R₂: 2-OCH₃

R³: 4-NHCO-

Crystalline form: White powder.
Recrystallization solvent: Dichloromethane/diethyl ether.
Melting point: 190°-193° C.
Form: Free.

EXAMPLE 150

Structure:

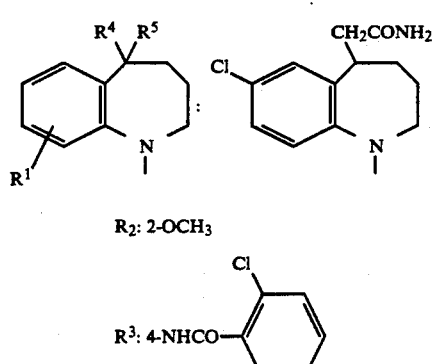

R₂: 2-OCH₃

R³: 4-NHCO-

Crystalline form: Colorless prisms.
Recrystallization solvent: Ethanol/n-hexane.
Melting point: 168°-175° C.

Form: Free.
NMR analysis: 146).

EXAMPLE 151

Structure:

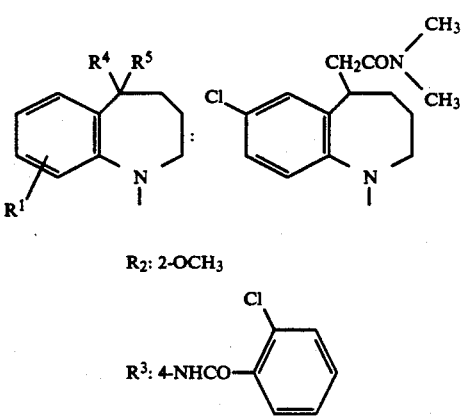

R₂: 2-OCH₃

R³: 4-NHCO-

Crystalline form: Colorless prisms.
Recrystallization solvent: Ethyl acetate/diethyl ether.
Melting point: 153°-155° C.
Form: Free.

EXAMPLE 152

Structure:

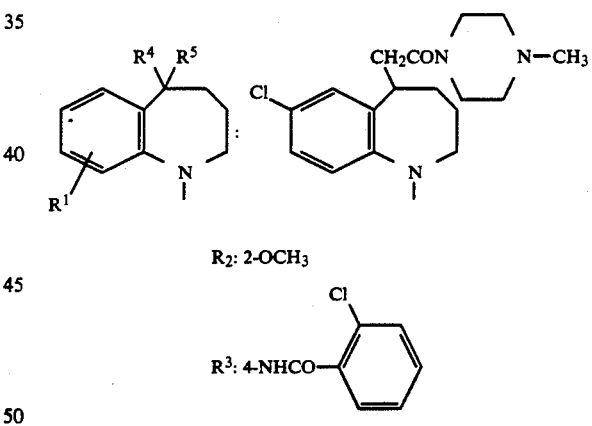

R₂: 2-OCH₃

R³: 4-NHCO-

Crystalline form: Colorless amorphous.
Form: Hydrochloride.
NMR analysis: 77).

EXAMPLE 153

Structure:

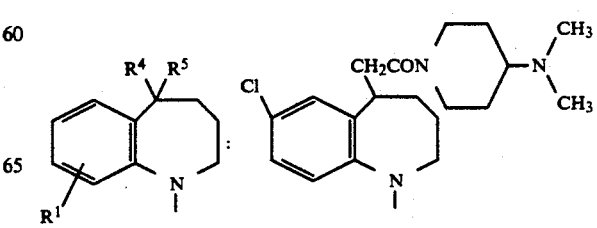

-continued

R₂: 2-OCH₃

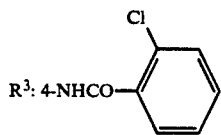

R³: 4-NHCO-

Crystalline form: Colorless amorphous.
Form: Hydrochloride.
NMR analysis: 78).

EXAMPLE 154

Structure:

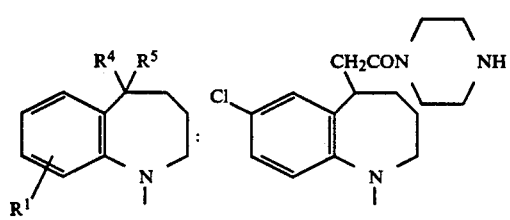

R₂: 2-OCH₃

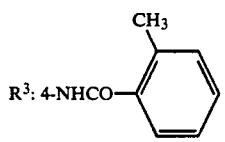

R³: 4-NHCO-

Crystalline form: Colorless amorphous.
Form: Hydrochloride.
NMR analysis: 79).

EXAMPLE 155

Structure:

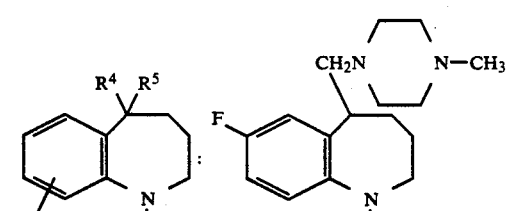

R₂: 2-OCH₃

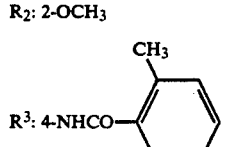

R³: 4-NHCO-

Crystalline form: Colorless amorphous.
Form: Free.
NMR analysis: 117).

EXAMPLE 156

Structure:

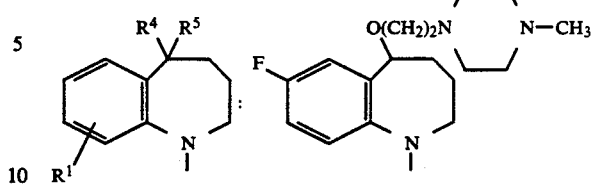

R₂: 2-OCH₃

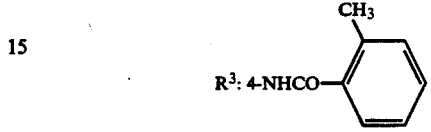

R³: 4-NHCO-

Crystalline form: Colorless amorphous.
Form: Free.
NMR analysis: 118).

EXAMPLE 157

Structure:

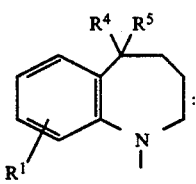

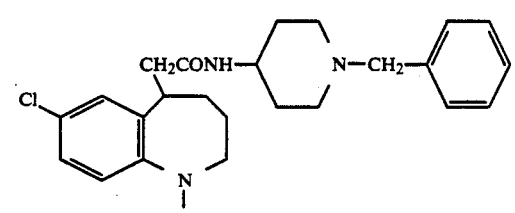

R₂: 2-OCH₃

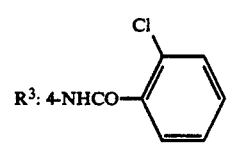

R³: 4-NHCO-

Crystalline form: Colorless amorphous.
Form: Hydrochloride.
NMR analysis: 80).

EXAMPLE 158

Structure:

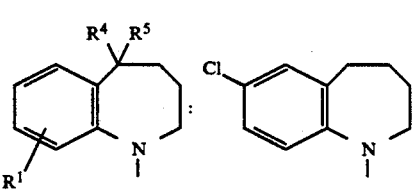

-continued

R₂: 2-OCH₃

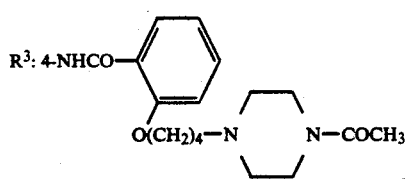

Crystalline form: colorless needles.
Recrystallization solvent: Ethanol/diethyl ether.
Melting point: 99°–102° C.
Form: Free.

EXAMPLE 159 I

Structure:

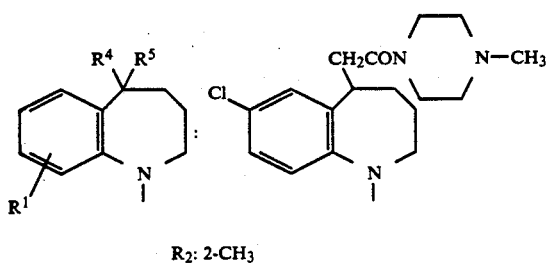

R₂: 2-CH₃

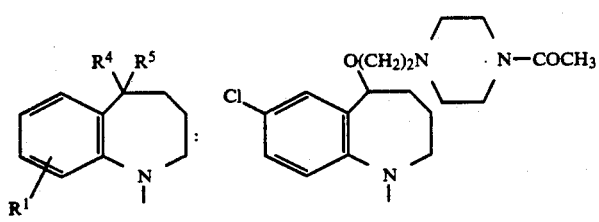

Crystalline form: colorless amorphous.
Form: Hydrochloride.
NMR analysis: 81).

EXAMPLE 160

Structure:

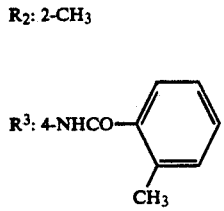

R₂: 2-CH₃

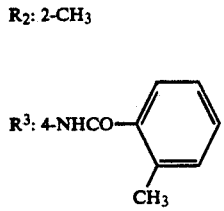

Crystalline form: Slightly yellow amorphous.
Form: Hydrochloride.
NMR analysis: 82).

EXAMPLE 161

Structure:

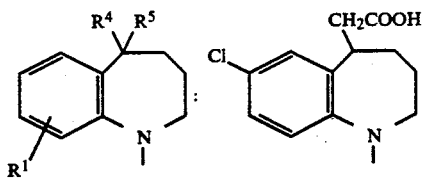

R₂: 2-Cl

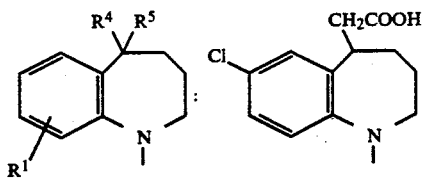

Crystalline form: White powder;
Recrystallization solvent: Ethyl acetate/diethyl ether.
Melting point: 227° C.
Form: Free.
NMR analysis: 102).

EXAMPLE 162

Structure:

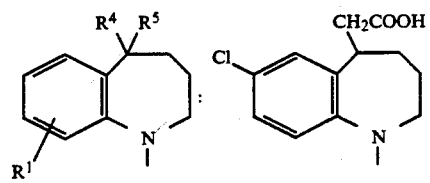

R₂: 2-CH₃

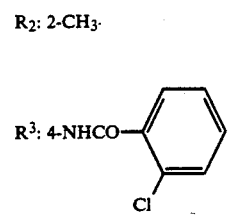

Crystalline form: white powder.
Recrystallization solvent: Ethyl acetate/n-hexane.
Melting point: 231°–232° C.
Form: Free.
NMR analysis: 101).

EXAMPLE 163

Structure:

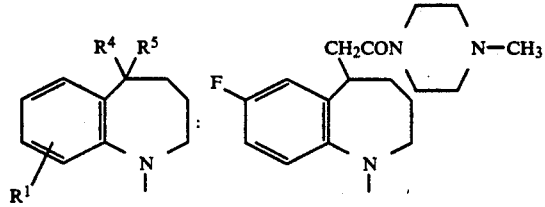

R₂: H

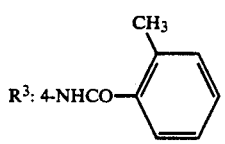

R³: 4-NHCO-

Crystalline form: Colorless amorphous.
Form: Free.
NMR analysis: 119).

EXAMPLE 164

Structure:

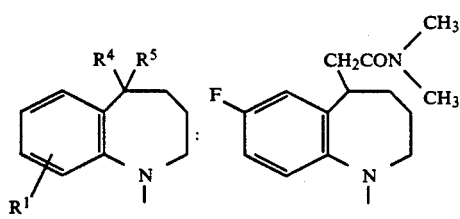

R₂: H

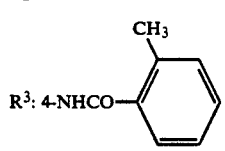

R³: 4-NHCO-

Crystalline form: Colorless amorphous.
Form: Free.
NMR analysis: 120).

EXAMPLE 165

Structure:

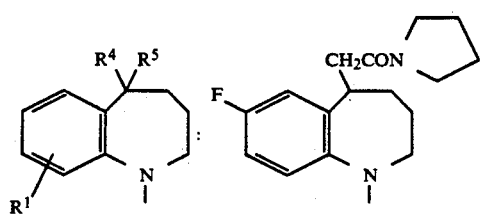

-continued

R₂: H

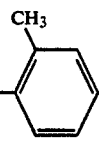

R³: 4-NHCO-

Crystalline form: Colorless amorphous.
Form: Free.
NMR analysis: 121).

EXAMPLE 166

Structure:

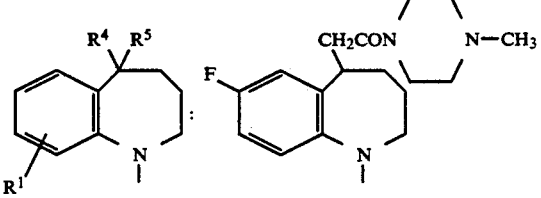

R₂: 2-OCH₃

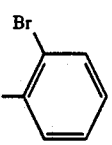

R³: 4-NHCO-

Crystalline form: Colorless amorphous.
Form: Free.
NMR analysis: 122).

EXAMPLE 167

Structure:

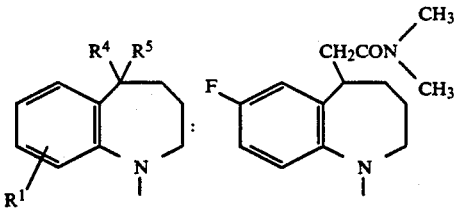

R₂: 2-OCH₃

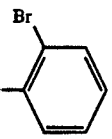

R³: 4-NHCO-

Crystalline form: Colorless amorphous.
Form: Free.
NMR analysis: 123).

EXAMPLE 168

Structure:

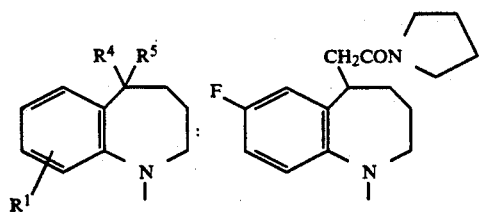

R₂: 2-OCH₃

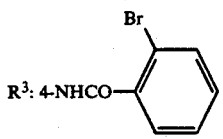

Crystalline form: colorless amorphous.
Form: Free.
NMR analysis: 124).

EXAMPLE 169

Structure:

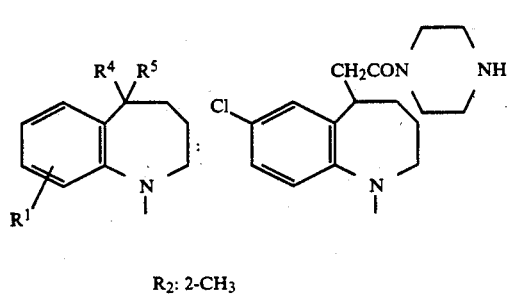

R₂: 2-CH₃

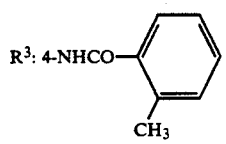

Crystalline form: White powder.
Recrystallization solvent: Ethanol/diethyl ether.
Melting point: 196° C.
Form: hydrochloride.

EXAMPLE 170 1

Structure:

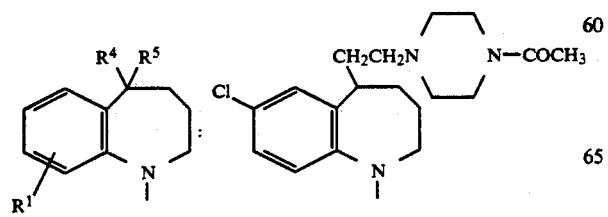

-continued

R₂: 2-CH₃

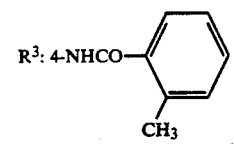

Crystalline form: colorless amorphous.
Form: hydrochloride.
NMR analysis: 83).

EXAMPLE 171

Structure:

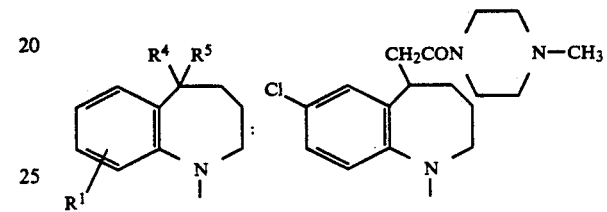

R₂: 2-Cl

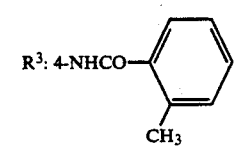

Crystalline form: White powder.
Recrystallization solvent: Ethanol/diethyl ether.
Melting point: 182°–183° C.
Form: Hydrochloride.

EXAMPLE 172

Structure:

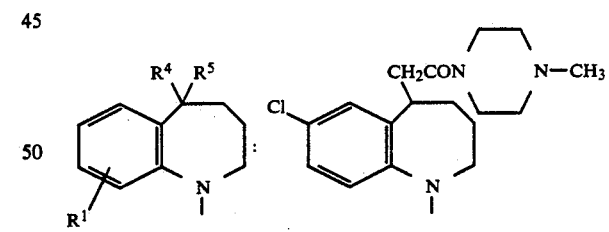

R₂: H

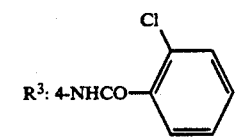

Crystalline form: colorless prisms.
Recrystallization solvent: Ethanol/diethyl ether.
Melting point: 193°–195° C. (decomposed).
Form: Hydrochloride.

EXAMPLE 173

Structure:

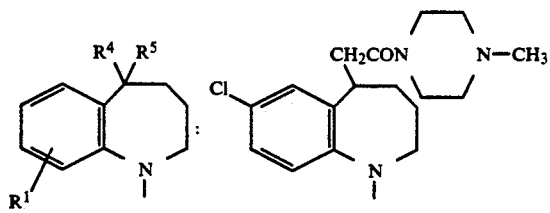

R₂: H

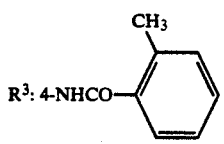

R³: 4-NHCO-

Crystalline form: Colorless prisms.
Recrystallization solvent: Ethanol/diethyl ether.
Melting point: 190°-193° C. (decomposed).
Form: hydrochloride.

EXAMPLE 174

Structure:

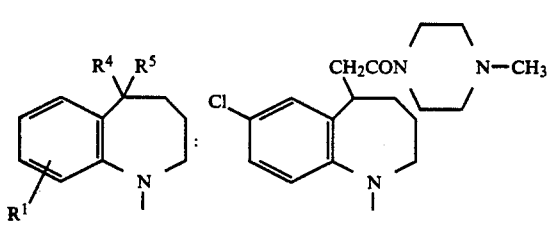

R₂: 3-OCH₃

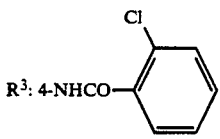

R³: 4-NHCO-

Crystalline form: White powder.
Recrystallization solvent: Ethanol/diethyl ether.
Melting point: 208°-209° C.
Form: Hydrochloride.

EXAMPLE 175

Structure:

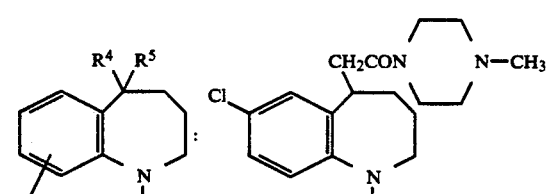

R₂: 3-OCH₃

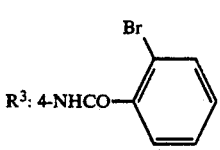

R³: 4-NHCO-

Crystalline form: White powder.
Recrystallization solvent: Ethanol/acetone/diethyl ether.
Melting point: 215°-217° C.
Form: Hydrochloride.

EXAMPLE 176

Structure:

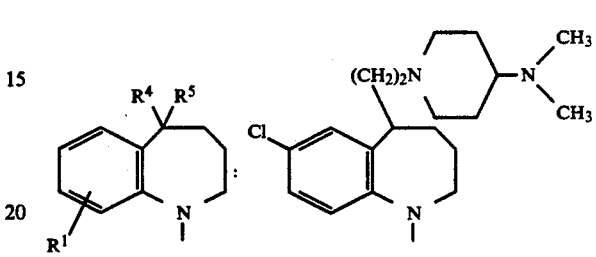

R₂: 2-OCH₃

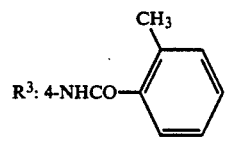

R³: 4-NHCO-

Crystalline form: Colorless needles.
Recrystallization solvent: Ethanol/diethyl ether.
Melting point: 222°-224° C.
Form: Dihydrochloride.

EXAMPLE 178

Structure:

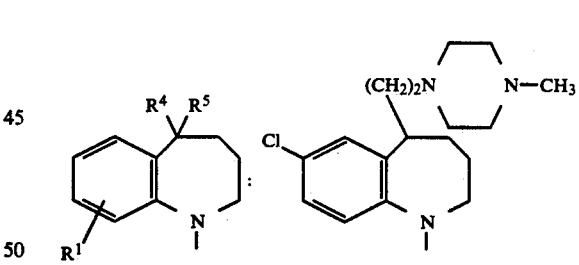

R₂: 2-OCH₃

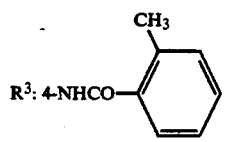

R³: 4-NHCO-

Crystalline form: Colorless needles.
Recrystallization solvent: Ethanol/diethyl ether.
Melting point: 214°-216° C.
Form: Dihydrochloride.

EXAMPLE 179

Structure:

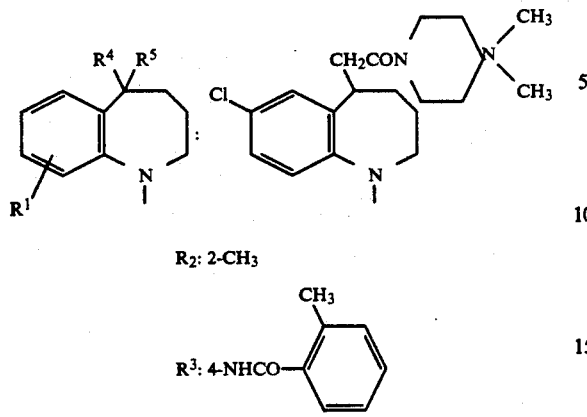

R²: 2-CH₃

R³: 4-NHCO-(o-tolyl)

Crystalline form: White powder.
Recrystallization solvent: Ethanol/diethyl ether.
Melting point: 254°–256° C.
Form: Hydrochloride.

EXAMPLE 180

Structure:

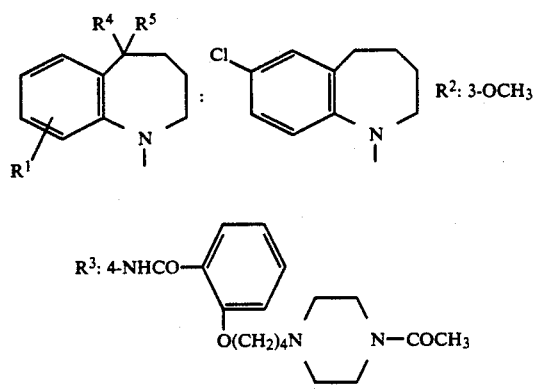

R²: 3-OCH₃

R³: 4-NHCO-phenyl-O(CH₂)₄N(piperazine)N—COCH₃

Crystalline form: Colorless needles.
Recrystallization solvent: Ethanol/diethyl ether.
Melting point: 148°–150° c.
Form: Free.

EXAMPLE 181

Structure:

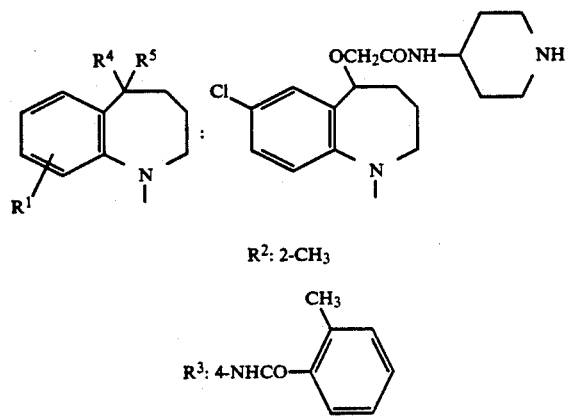

R²: 2-CH₃

R³: 4-NHCO-(o-tolyl)

Crystalline form: Colorless amorphous.
Form: Hydrochloride.
NMR analysis: 145).

EXAMPLE 182

Structure:

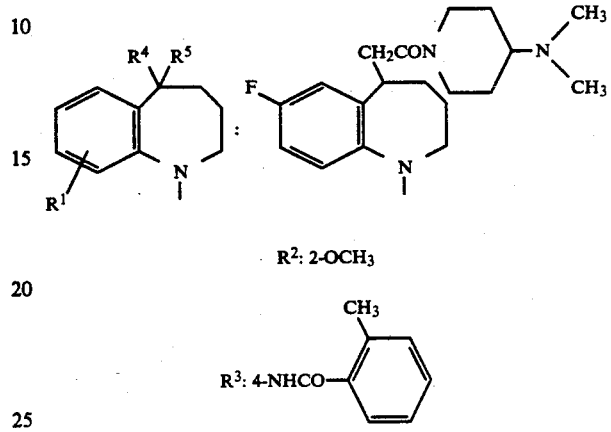

R²: 2-OCH₃

R³: 4-NHCO-(o-tolyl)

Crystalline form: Colorless amorphous.
Form: Free.
NMR analysis: 125).

EXAMPLE 183

Structure:

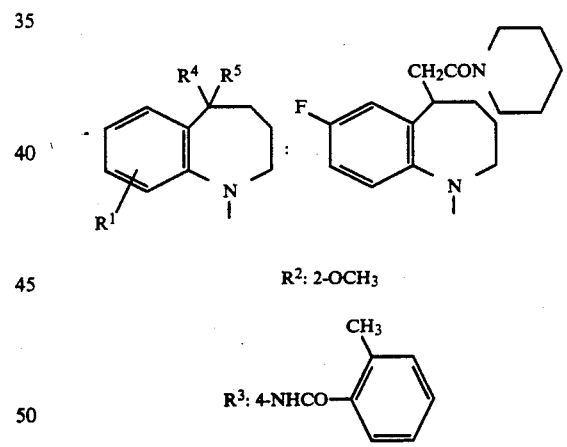

R²: 2-OCH₃

R³: 4-NHCO-(o-tolyl)

Crystalline form: Colorless amorphous.
Form: Free.
NMR analysis: 126).

EXAMPLE 184

Structure:

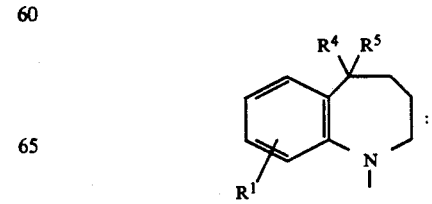

-continued

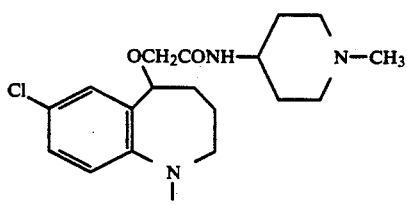

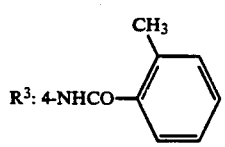

Crystalline form: White powder.
Recrystallization solvent: Ethanol/diethyl ether.
Melting point: 186°–188° C.
Form: Hydrochloride.

EXAMPLE 185
Structure:

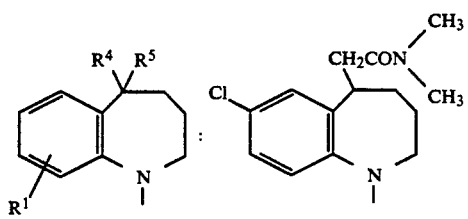

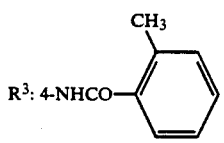

Crystalline form: White powder.
Recrystallization solvent: Dichloromethane/diethyl ether.
Melting point: 239.5°–240.5° C.
Form: Free.

EXAMPLE 186
Structure:

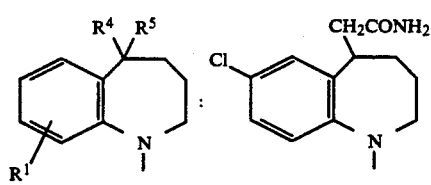

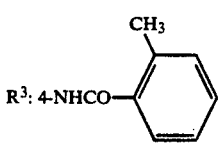

Crystalline form: White powder.
Recrystallization solvent: Dichloromethane/diethyl ether.
Melting point: 253°–255° C.
Form Free.

EXAMPLE 187
Structure:

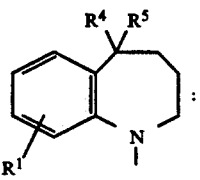

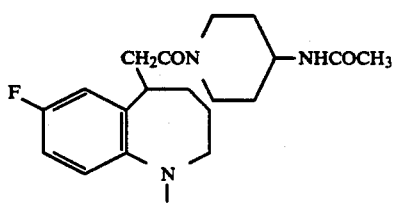

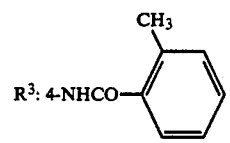

Crystalline form: Colorless amorphous.
Form: Free.
NMR analysis: 127).

EXAMPLE 188
Structure:

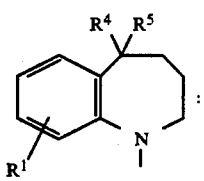

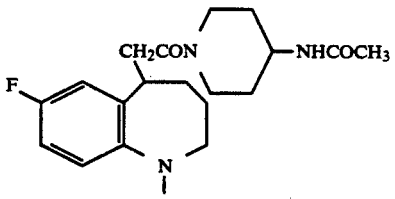

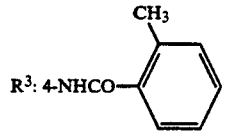

Crystalline form: Colorless amorphous.
Form: Free.

NMR analysis: 128).

EXAMPLE 189

Structure:

[Structure with R⁴, R⁵ at top and R¹ on benzazepine ring]

[Structure with F, CH₂CON-piperidine-NHCOCH₃ group]

R²: 2-OCH₃

R³: 4-NHCO- (2-Br phenyl)

Crystalline form: Colorless amorphous.
Form: Free.
NMR analysis: 129).

EXAMPLE 190

Structure:

[Structure with R⁴, R⁵ benzazepine and Cl-benzazepine with OCH₂CH₂OH]

R²: H

R³: 4-NHCO- (2-CH₃ phenyl)

Crystalline form: White powder.
Recrystallization solvent: Dichloromethane/diethyl ether.
Melting point: 185°–187.5° C.
Form: Free.

EXAMPLE 191

Structure

[Structure with R⁴, R⁵ benzazepine and Cl-benzazepine with =CO₂C₂H₅ group]

R²: 2-OCH₃

R³: 4-NHCO- (2-CH₃ phenyl)

Crystalline form: pale yellow oil.
Form: Free.
NMR analysis: 84).

EXAMPLE 192

Structure:

[Structure with R⁴, R⁵ benzazepine and Cl-benzazepine with O(CH₂)₃N-piperazine-N-CO₂C(CH₃)₃]

R²: 2-OCH₃

R³: 4-NHCO- (2-CH₃ phenyl)

Crystalline form: Pale yellow amorphous.
Form: Free.
NMR analysis: 85).

EXAMPLE 193

Structure:

[Structure with R⁴, R⁵ benzazepine and Cl-benzazepine with CH₂CO₂CH₃ group]

R²: 2-OCH₃

-continued

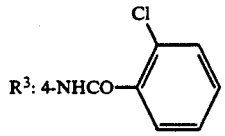
R³: 4-NHCO-

Crystalline form: Pale yellow amorphous.
Form: Free.
NMR analysis: 86).

EXAMPLE 194
Structure:

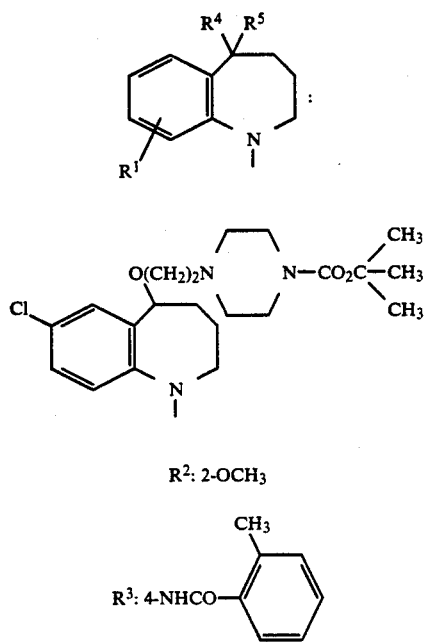

R²: 2-OCH₃

R³: 4-NHCO-

Crystalline form: Colorless amorphous.
Form: Free.
NMR analysis: 87).

EXAMPLE 195
Structure:

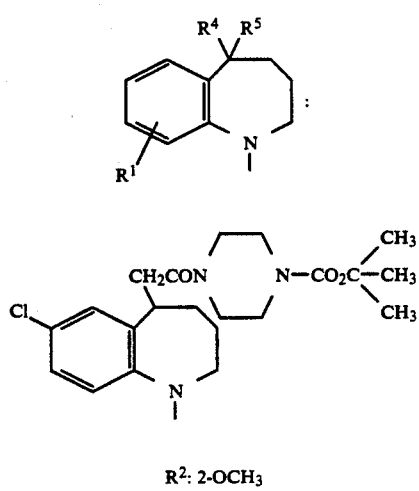

R²: 2-OCH₃

-continued

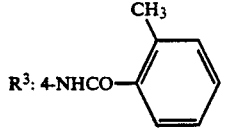
R³: 4-NHCO-

Crystalline form: White powder.
Melting point: 145°–147° C.
Form: Free.

EXAMPLE 196
Structure

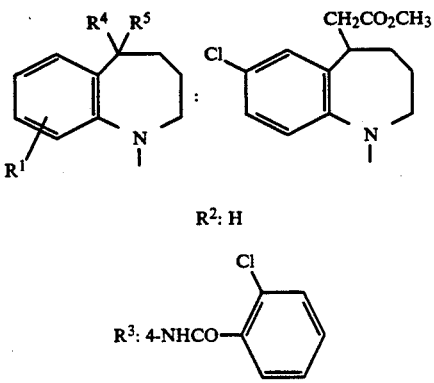

R²: H

R³: 4-NHCO-

Crystalline form: colorless amorphous.
Form: Free.
NMR analysis: 88).

EXAMPLE 197
Structure:

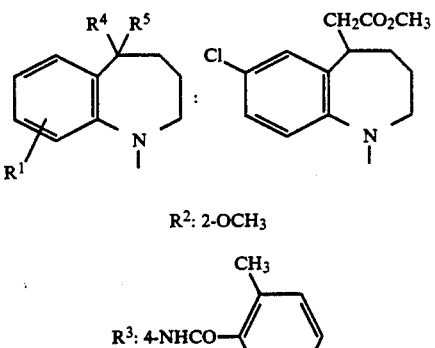

R²: 2-OCH₃

R³: 4-NHCO-

Crystalline form: colorless amorphous.
Form: Free.
NMR analysis: 89).

EXAMPLE 198
Structure:

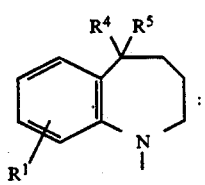

-continued

R[2]: 2-OCH$_3$

R[3]: 4-NHCO-(2-methylphenyl)

Crystalline form: Pale yellow amorphous.
Form: Free.
NMR analysis: 90).

EXAMPLE 199

Structure:

R[2]: H

R[3]: 4-NHCO-(2-methylphenyl)

Crystalline form: Colorless amorphous.
Form: Free.
NMR analysis: 91).

EXAMPLE 200

Structure:

R[2]: H

R[3]: 4-NHCO-(2-chlorophenyl)

Crystalline form: colorless amorphous.
Form: Free.
NMR analysis: 92).

EXAMPLE 201

Structure:

R[2]: 2-OCH$_3$

R[3]: 4-NHCO-(2-methylphenyl)

Crystalline form: White powder.
Form: Free.
NMR analysis: 93).

EXAMPLE 202

Structure:

R[2]: 3-OCH$_3$

R[3]: 4-NHCO-(2-methylphenyl)

Crystalline form: Colorless amorphous.
Form: Free.
NMR Analysis: 94).

EXAMPLE 203

Structure:

-continued
R₂: 3-OCH₃

R³: 4-NHCO—[2-methylphenyl]

Crystaline form: Colorless powder.
Form: Free.
NMR analysis: 95).

EXAMPLE 204

Structure:

[benzazepine core with R⁴, R⁵ at C5; Cl and CH₂CON-piperazine-N—COOC(CH₃)₃ substituent]

R₂: 2-CH₃

R³: 4-NHCO—[2-methylphenyl]

Crystalline form: colorless amorphous.
Form: Free.
NMR analysis: 97).

EXAMPLE 205

Structure:

[benzazepine core with R⁴, R⁵; Cl and O(CH₂)₂OSO₂—[4-methylphenyl] substituent]

-continued
R₂: 2-CH₃

R³: 4-NHCO—[2-methylphenyl]

Crystalline form: colorless amorphous.
Form: Free.
NMR analysis: 98).

EXAMPLE 206

Structure:

[benzazepine core with R⁴, R⁵; Cl and O(CH₂)₃O—C(=O)—[4-methylphenyl] substituent]

R₂: 2-CH₃

R³: 4-NHCO—[2-methylphenyl with CH₃]

Crystalline form: Colorless amorphous.
Form: Free.
NMR analysis: 99).

EXAMPLE 207

Structure:

[two benzazepine cores: one with R⁴, R⁵ and R¹; other with Cl and CH₂CO₂CH₃]

R₂: 2-CH₃

R³: 4-NHCO—[2-chlorophenyl]

Crystalline form: Colorless amorphous.
Form: Free.

EXAMPLE 208

Structure:

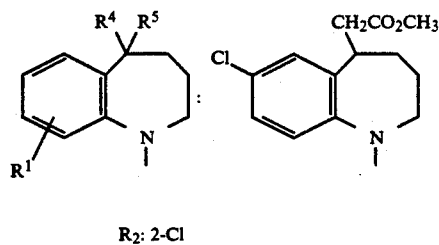

R$_2$: 2-Cl

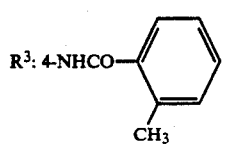

Crystaline form: Colorless amorphous.
From: Free.
NMR analysis: 103).

EXAMPLE 209

Structure:

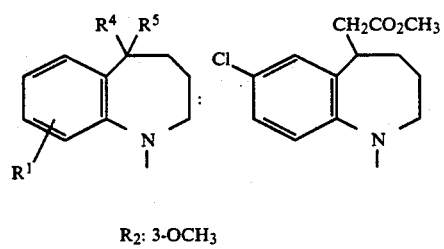

R$_2$: 3-OCH$_3$

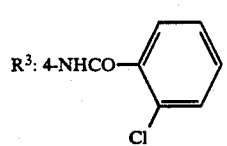

Crystalline form: Colorless amorphous.
Form: Free.
NMR analysis: 104).

EXAMPLE 210

Structure:

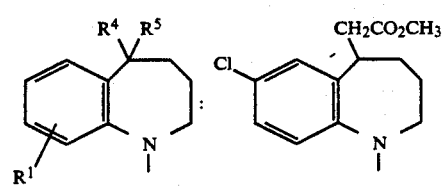

R$_2$: 3-OCH$_3$

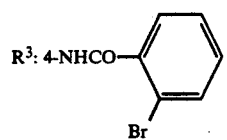

Crystalline form: colorless amorphous.
Form: Free.
NMR analysis: 105).

EXAMPLE 211

Structure:

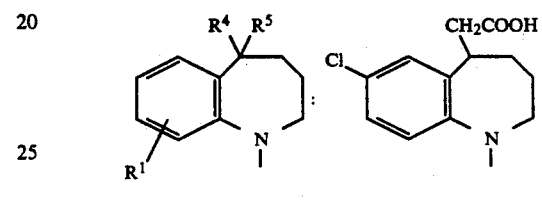

R$_2$: 3-OCH$_3$

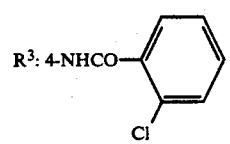

Crystalline form: colorless amorphous.
Form: Free.
NMR analysis: 106).

EXAMPLE 212

Structure:

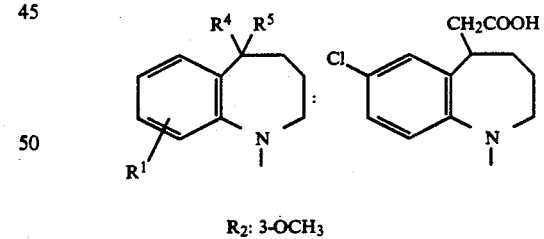

R$_2$: 3-OCH$_3$

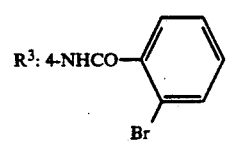

Crystalline form: colorless amorphous.
Form: Free.
NMR analysis: 107).

EXAMPLE 213

Structure:

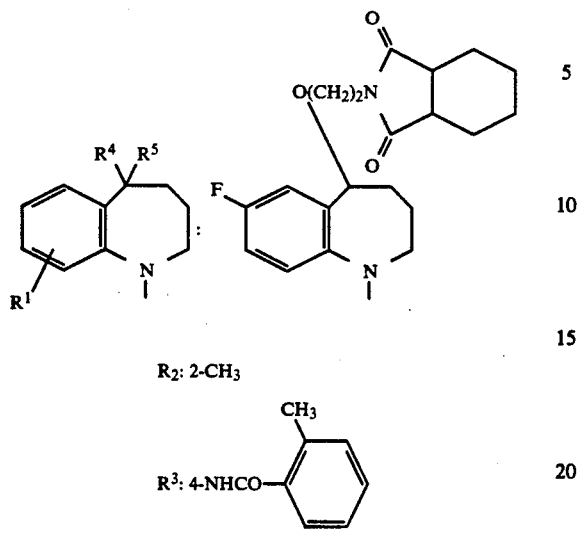

R₂: 2-CH₃

R³: 4-NHCO- (2-methylphenyl)

Crystalline form: Colorless amorphous.
Form: Free.
NMR analysis: 130).

EXAMPLE 214

Structure:

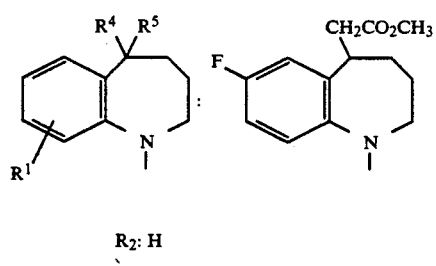

R₂: H

R³: 4-NHCO- (2-methylphenyl)

Crystalline form: Colorless amorphous.
Form: Free.
NMR analysis: 135).

EXAMPLE 215

Structure:

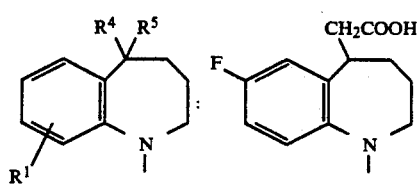

-continued
R₂: H

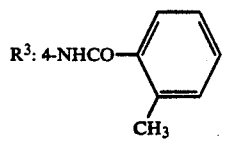
R³: 4-NHCO- (2-methylphenyl)

Crystaline form: Colorless amorphous.
Form: Free.
NMR analysis: 136).

EXAMPLE 216

Structure:

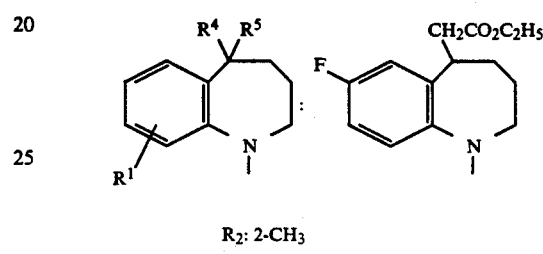

R₂: 2-CH₃

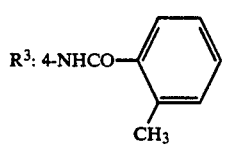
R³: 4-NHCO- (2-methylphenyl)

Crystalline form: colorless amorphous.
Form: Free.
NMR analysis: 137).

EXAMPLE 217

Structure:

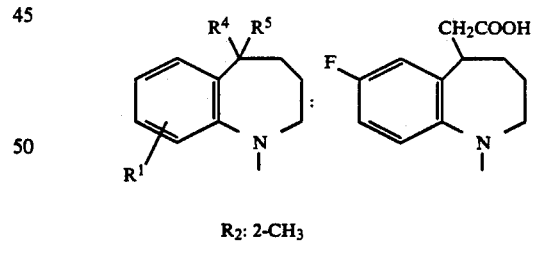

R₂: 2-CH₃

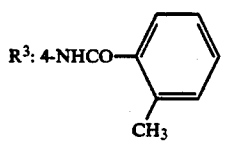
R³: 4-NHCO- (2-methylphenyl)

Crystalline form: Colorless amorphous.
Form: Free.
NMR analysis: 138).

EXAMPLE 218

Structure:

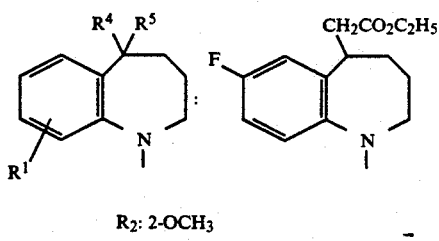

R₂: 2-OCH₃

R₃: 4-NHCO— (2-methylphenyl)

Crystalline form: Colorless amorphous.
Form: Free.
NMR analysis: 139).

EXAMPLE 219

Structure:

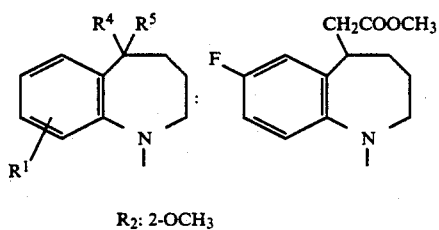

R₂: 2-OCH₃

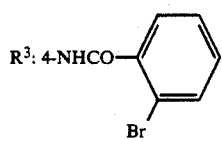

R₃: 4-NHCO— (2-bromophenyl)

Crystalline form: Colorless amorphous.
Form: Free.
NMR analysis: 140).

EXAMPLE 220

Structure:

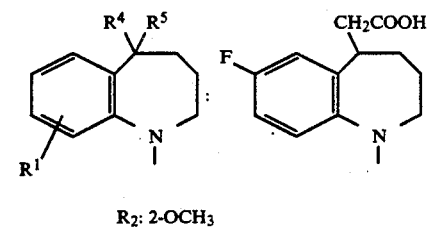

R₂: 2-OCH₃

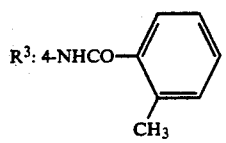

R₃: 4-NHCO— (2-methylphenyl)

Crystalline form: Colorless amorphous.
Form: free.

NMR analysis: 141).

EXAMPLE 221

Structure:

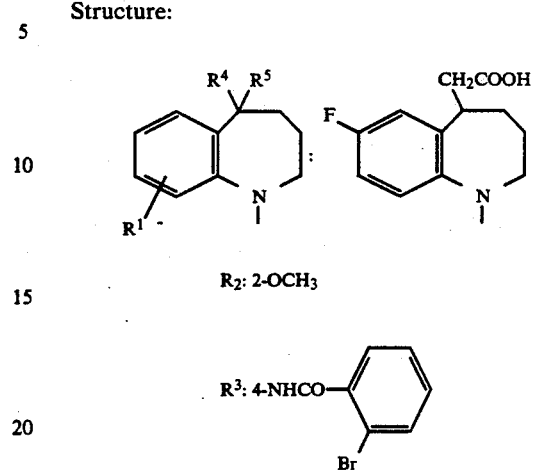

R₂: 2-OCH₃

R₃: 4-NHCO— (2-bromophenyl)

Crystalline form: Colorless amorphous.
Form: Free.
NMR analysis: 142).

EXAMPLE 222

Structure:

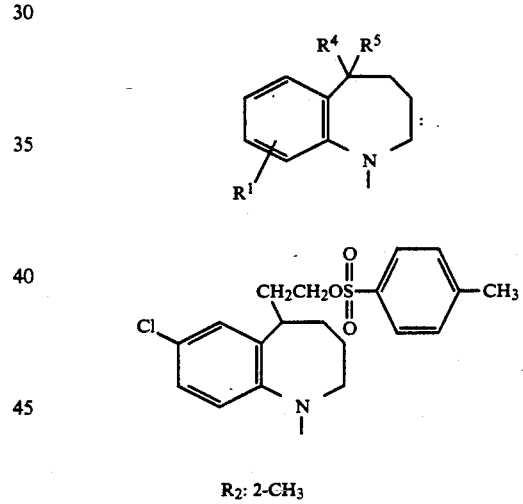

R₂: 2-CH₃

R₃: 4-NHCO— (2-methylphenyl)

Crystalline form: White amorphous.
Form: Free.
NMR analysis: 143).

46) $^1$H-NHR (DMSO-$d_6$) δ; 1.35–2.45 (12H, m), 2.55–2.95 (3H, m), 3.1–4.0 (4H, m), 4.05–4.45 (1H, m), 4.5–4.8 (1H, m), 5.95–6.3 (1H, m), 6.89 (1H, d, J=8.6 Hz), 7.05–7.8 (9H, m), 8.17 (3H, brs), 8.90 (3H, brs), 10.25–10.6 (1H, m).

47) $^1$H-NHR (CDCl$_3$) δ; 1.22–2.52 (10H, m), 2.70–3.05 (1H, m), 3.30–5.10 (8H, m), 6.60–8.05 (12H, m).

48) ¹H-NHR (CDCl₃) δ; 1.21–2.46 (7H, m), 2.70–2.95 (1H, m), 2.95–5.60 (7H, m), 6.60–8.32 (11H, m), 8.60–9.40 (1H, m).

49) ¹H-NHR (CDCl₃) δ; 1.35–2.52 (10H, m), 2.70–3.02 (1H, m), 3.02–5.05 (8H, m), 6.60–7.85 (11H, m), 7.85–8.23 (1H, m).

50) ¹H-NHR (CDCl₃) δ; 1.44–2.51 (11H, m), 2.67–3.77 (7H, m), 3.88–5.00 (4H, m), 6.66–9.05 (11H, m).

51) ¹H-NHR (DMSO-d₆) δ; 1.02–1.43 (3H, m), 1.43–4.98 (10H, m), 6.80–8.25 (11H, m), 10.35–10.72 (1H, m), 12.37–13.00 (1H, m).

52) ¹H-NHR (CDCl₃) δ; 1.15–5.30 {20H, m [1.28 (3H, t, J=7.1 Hz), 2.50 (s), 3.73 (3H, s)]}, 6.50–7.61 (9H, m), 8.32 (1H, brs), 8.34 (1H, d, J=8.1 Hz).

53) ¹H-NHR (CDCl₃) δ; 1.21–5.34 [15H, m (2.50 (s), 3.78 (s))], 5.91–8.78 [13H, m (6.56 (1H, d, J=8.3 Hz))].

54) ¹H-NHR (CDCl₃) δ; 1.06–4.66, 5.02–5.26, 5.54–5.79 [total 25H, m (2.48 (s), 2.56 (s), 3.98 (s))], 6.61–7.64, 8.04–8.39, 8.57–8.76 (total 12H, m).

55) ¹H-NHR (CDCl₃) δ; 1.26–4.82 (19H, m), 5.68 (1H, t, J=7.1 Hz), 6.64–7.47 (9H, m), 7.80–8.30 (2H, m).

56) ¹H-NHR (CDCl₃) δ; 1.26–4.68 (19H, m), 5.58 (1H, t, J=6.9 Hz), 6.63–8.50 (11H, m).

57) ¹H-NHR (DMSO-d₆) δ; 1.02–2.04 (4H, m), 2.33, 2.40 (total 3H, s), 2.50–4.22 (14H, m), 2.75, 2.77 (total 3H, s), 4.29–4.68 (2H, m), 6.73–7.78 (10H, m), 10.30, 10.50 (total 1H, brs), 11.50 (1H, brs).

58) ¹H-NHR (CDCl₃) δ; 1.0–1.4 (1H, m), 1.4–2.25 (3H, m), 2.25–3.3 (12H, m), 3.35–4.15 (4H, m), 4.3–4.95 (1H, m), 6.6–8.0 (10H, m), 8.6–9.25 (1H, m).

59) ¹H-NHR (CDCl₃) δ; 1.2–2.35 (6H, m), 2.35–2.6 (6H, m), 2.6–2.95 (1H, m), 3.1–4.05 (5H, m), 4.05–4.45 (2H, m), 4.45–5.1 (2H, m), 6.55–6.8 (1H, m), 6.8–7.55 (11H, m), 7.6–7.95 (3H, m).

60) ¹H-NHR (DMSO-d₆) δ; 1.3–2.45 (9H, m), 2.6–2.85 (1H, m), 2.9–4.1 (14H, m), 4.4–4.8 (2H, m), 6.88 (1H, d, J=8.4 Hz), 7.0–7.75 (10H, m), 10.25–10.55 (1H, m), 11.01 (1H, brs).

61) ¹H-NHR (DMSO-d₆) δ; 1.2–2.45 (8H, m), 2.6–2.85 (1H, m), 3.2–4.0 (6H, m), 4.2–4.8 (4H, m), 6.87 (1H, d, J=8.4 Hz), 7.0–8.0 (11H, m), 9.05–9.3 (1H, m), 10.2–10.55 (1H, m).

62) ¹H-NHR (DMSO-d₆) δ; 1.10–2.48 (12H, m), 2.65–4.10 (13H, m), 4.48–5.00 (2H, m), 6.58–7.22 (2H, m), 7.22–7.86 (8H, m), 10.29, 10.45 (total 1H, brs), 11.07 (1H, brs).

63) ¹H-NHR (DMSO-d₆) δ; 1.24–1.82 (3H, m), 1.82–2.48 (9H, m), 2.66–3.94 (3H, m), 4.22–4.93 (2H, m), 6.63–7.98 (14H, m), 9.08, 9.18 (total 1H, brs), 10.29, 10.44 (total 1H, brs).

64) ¹H-NHR (DMSO-d₆) δ; 1.2–2.45 (13H, m), 2.6–2.8 (1H, m), 2.8–3.8 (10H, m), 3.83 (1H, d, J=7.2 Hz), 4.4–4.8 (2H, m), 6.88 (1H, d, J=8.4 Hz), 7.0–7.75 (9H, m), 10.2–10.8 (2H, m).

65) ¹H-NHR (DMSO-d₆) δ; 0.96–2.63 (19H, m), 2.63–4.04 (6H, m), 4.07–4.95 (2H, m), 6.57–7.99 (11H, m), 10.29, 10.44 (total 1H, brs), 10.49 (1H, brs).

66) ¹H-NHR (CDCl₃) δ; 1.44–2.59 (10H, m), 2.60–5.25 (3H, m), 6.42–8.33 (11H, m).

67) ¹H-NHR (DMSO-d₆) δ; 1.2–2.3 (9H, m), 2.3–2.45 (3H, m), 2.6–2.8 (1H, m), 2.8–3.9 (14H, m), 3.9–4.15 (1H, m), 4.3–4.8 (2H, m), 6.88 (1H, d, J=8.4 Hz), 6.95–7.7 (9H, m), 10.2–10.5 (1H, m), 10.95 (1H, brs).

68) ¹H-NHR (DMSO-d₆) δ; 0.97–2.62 [15H, m (2.07, 3H, s)], 2.63–4.19 (13H, m), 4.31–5.01 (2H, m), 6.54–8.07 (10H, m), 10.30, 10.46 (total 1H, brs), 10.98 (1H, brs).

69) ¹H-NHR (DMSO-d₆) δ; 1.02–2.15 (4H, m), 2.15–2.48 (6H, m), 2.80 (3H, s), 2.64–3.88 [10H, m (2.80, 3H, s-like)], 3.95–4.78 (3H, m), 6.45–8.12 (10H, m), 10.26, 10.47 (total 1H, brs), 11.30 (1H, brs).

70) ¹H-NHR (CDCl₃) δ; 1.3–1.8 (2H, m), 1.85–2.35 (2H, m), 2.35–2.6 (6H, m), 2.65–2.9 (1H, m), 3.35–4.0 (5H, m), 4.1–5.05 (4H, m), 6.5–6.8 (1H, m), 6.8–7.6 (10H, m), 7.6–8.05 (4H, m).

71) ¹H-NHR (DMSO-d₆) δ; 1.25–2.45 (9H, m), 2.55–2.85 (1H, m), 2.9–4.1 (15H, m), 4.3–4.8 (2H, m), 6.88 (1H, d, J=8.4 Hz), 7.0–7.8 (9H, m), 9.84 (2H, brs), 10.15–10.55 (1H, m), 12.02 (1H, brs).

72) ¹H-NHR (DMSO-d₆) δ; 1.3–2.15 (3H, m), 2.15–2.45 (4H, m), 2.6–2.85 (1H, m), 3.0–4.25 (15H, m), 4.45–4.9 (2H, m), 6.89 (1H, d, J=8.4 Hz), 7.0–7.75 (9H, m), 10.25–10.6 (1H, m), 11.05–11.65 (1H, m).

73) ¹H-NHR (DMSO-d₆) δ; 1.15–2.2 (4H, m), 2.25–2.4 (3H, m), 2.6–2.85 (1H, m), 3.0–3.95 (4H, m), 3.95–4.15 (1H, m), 4.35–4.8 (4H, m), 6.6–6.95 (1H, m), 6.95–8.0 (12H, m), 9.15–9.45 (1H, m), 0.25–10.6 (1H, m).

74) ¹H-NHR (DMSO-d₆) δ; 1.3–2.2 (7H, m), 2.2–2.45 (4H, m), 2.55–2.85 (1H, m), 2.85–4.25 (11H, m), 4.25–4.85 (5H, m), 6.89 (1H, d, J=8.4 Hz), 7.0–7.8 (9H, m), 10.25–10.6 (1H, m), 11.45–12.0 (1H, m).

75) ¹H-NHR (DMSO-d₆) δ; 1.3–2.2 (7H, m), 2.2–2.45 (4H, m), 2.55–2.9 (1H, m), 2.9–4.15 (11H, m), 4.4–4.9 (2H, m), 6.8–7.0 (1H, m), 7.0–7.8 (9H, m), 10.2–10.7 (1H, m), 10.88 (1H, brs).

76) ¹H-NHR (DMSO-d₆) δ; 1.3–2.1 (3H, s), 2.15–2.45 (4H, m), 2.55–2.85 (1H, m), 2.9–4.25 (15H, m), 4.4–4.85 (2H, m), 6.75–7.0 (1H, m), 7.0–7.9 (9H, m), 9.90 (2H, brs), 10.2–10.55 (1H, m), 11.65–12.50 (1H, m).

77) ¹H-NHR (DMSO-d₆) δ; 0.94–2.05 (4H, m), 2.45–4.90 (22H, m), 2.77 (3H, s), 6.80 (1H, d, J=8.6 Hz), 6.94–7.77 (9H, m), 10.52, 10.72 (total 1H, brs), 11.47 (1H, brs).

78) ¹H-NHR (DMSO-d₆) δ; 1.0–2.3 (8H, m), 2.4–3.2 (1H, m), 3.2–4.2 (6H, m), 4.2–4.8 (2H, m), 6.80 (1H, d, J=8.4 Hz), 6.95–7.8 (9H, m), 10.5–10.75 (1H, m), 10.86 (1H, brs).

79) ¹H-NHR (DMSO-d₆) δ; 0.9–1.3 (1H, m), 1.3–2.0 (3H, m), 2.05–2.45 (3H, m), 2.55–3.3 (6H, m), 3.3–4.55 (10H, m), 6.8–7.8 (10H, m), 9.51 (2H, brs), 10.2–10.6 (1H, m).

80) ¹H-NHR (DMSO-d₆) δ; 0.75–2.25 (10H, m), 2.25–4.4 (13H, m), 6.79 (1H, d, J=8.2 Hz), 6.9–7.9 (14H, m), 8.25–8.8 (1H, m), 10.45–10.85 (1H, m), 10.85–11.35 (1H, m).

81) ¹H-NHR (DMSO-d₆) δ; 1.07–2.10 (4H, m), 2.19–2.62 (3H, m), 2.62–4.72 (16H, m), 6.60–7.84 (10H, m), 10.48, 10.68 (total 1H, brs), 11.32 (1H, brs).

82) ¹H-NHR (DMSO-d₆) δ; 1.04–2.68 [13H, m (2.08, 3H, s)], 2.68–4.24 (13H, m), 4.32–5.00 (2H, m), 6.54–7.91 (10H, m), 10.29, 10.44 (total 1H, brs), 11.14 (1H, brs).

83) ¹H-NHR (DMSO-d₆) δ; 1.02–2.59 [16H, m (2.09, 3H, s-like)], 2.59–3.83 (9H, m), 3.87–4.63 (2H, m), 6.56–8.12 (10H, m), 10.27, 10.45 (total 1H, brs), 11.00 (1H, brs).

84) ¹H-NHR (CDCl₃) δ; 1.34 (3H, t, J=5.6 Hz), 1.55–2.3 (3H, m), 2.46 (3H, s), 2.8–3.9 (6H, m), 4.24 (2H, q, J=5.6 Hz), 5.96 (1H, s), 6.6–7.6 (10H, m), 8.10 (1H, s).

85) ¹H-NHR (CDCl₃) δ; 1.3–2.6 (28H, m), 2.6–2.9 (1H, m), 3.0–4.0.(5H, m), 4.3–5.1 (2H, m), 6.6–7.6 (10H, m), 7.70 (1H, brs).

86) ¹H-NHR (CDCl₃) δ; 1.1–2.25 (4H, m), 2.55–3.15 (3H, m), 3.3–4.0 (7H, m), 4.05–5.1 (1H, m), 6.7–7.9 (10H, m), 8.3–8.75 (1H, m).

87) ¹H-NHR (CDCl₃) δ; 1.3-2 9 (23H, m), 3.25-4.0 (9H, m), 4.3-5.1 (2H, m), 6.6-7.55 (10H, m), 7.6-7.95 (1H, m).

88) ¹H-NHR (CDCl₃) δ; 1.15-2.2 (4H, m), 2.5-3.3 (3H, m), 3.4-3.9 (4H, m), 4.3-5.25 (1H, m), 6.45-6.7 (1H, m), 6.8-7.05 (1H, m), 7.05-7.6 (8H, m), 7.6-7.8 (1H, m), 8.1-8.4 (1H, m).

89) ¹H-NHR (CDCl₃)δ; 1.2-2.5 (7H, m), 2.55-3.25 (3H, m), 3.3-3.85 (4H, m), 4.35-5.2 (1H, m), 6.59 (1H, d, J=6.7 Hz), 6.95 (1H, dd, J=6.7 Hz, 1.6 Hz), 7.11 (1H, d, J=1.7 Hz), 7.15-8.05 (9H, m).

90) ¹H-NHR (CDCl₃) δ; 0.95-2.35 (6H, m), 2.35-2.6 (6H, m), 2.6-3.3 (2H, m), 3.35-5.05 (6H, m), 6.55-6.8 (1H, m), 6.8-8.15 (14H, m).

91) ¹H-NHR (CDCl₃) δ; 1.2-2.2 (4H, m), 2.35 (3H, s), 2.55-3.05 (2H, m), 3.05-3.25 (1H, m), 3.45-3.75 (1H, m), 4.2-5.15 (1H, m), 6.45-6.6 (1H, m), 6.75-6.95 (1H, m), 7.0-8.05 (9H, m), 8.15-8.45 (1H, m).

92) ¹H-NHR (CDCl₃) δ; 1.2-2.2 (4H, m), 2.5-3.0 (2H, m), 3.0-3.25 (1H, m), 3.3-3.75 (1H, m), 4.2-5.2 (1H, m), 6.45-6.65 (1H, m), 6.8-7.0 (1H, m), 7.0-7.5 (8H, m), 7.55 (1H, d, J=6.9 Hz), 8.4-8.6 (1H, m).

93) ¹H-NHR (CDCl₃) δ; 1.15-1.45 (1H, m), 1.45-2.4 (5H, m), 2.4-2.7 (3H, m), 3.05-3.35 (2H, m), 3.45-4.1 (5H, m), 4.35-5.2 (1H, m), 6.6-7.6 (10H, m), 7.6-7.8 (3H, m), 7.8-8.05 (2H, m).

94) ¹H-NHR (CDCl₃)δ; 1.23-2.30, 2.56-3.98, 4.27-5.65 [total 16H, 2.47 (3H, s), 3.72 (3H, s)], 6.61 s), 8.31 (1H, d, J=8.1 Hz).

95) ¹H-NHR (CDCl₃) δ; 1.56-5.10 (6H, m), 2.50 (3H, s), 3.80 (3H, s), 5.59 (1H, s), 6.51-6.86 (2H, m), 6.91-7.06 (1H, m), 7.13 (1H, dd, J=2.4 Hz, 8.4 Hz), 7.19-7.58 (5H, m), 8.15 (1H, s), 8.32 (1H, d, J=8.4 Hz).

96) ¹H-NMR (DMSO-d₆) δ; 1.2-2.2 (3H, m), 2.35 (3H, s), 2.83 (6H, s), 2.7-3.2 (1H, m), 3.3-3.6 (3H, m), 4.29 (2H, s), 4.2-5.1 (2H, m), 6.80 (1H, d, J=8.2 Hz), 7.0-7.8 (10H, m), 10.4-10.6 (1H, m), 10.6-10.9 (1H, br).

97) ¹H-NMR (CDCl₃) δ; 0.88-4.12 (16H, m), 1.44, 1.46, 1.48 (9H, each s), 2.45, 2.51 (6H, each s), 4.31-4.62 (1H, m), 6.58 (1H, d, J=8.2 Hz), 6.78-8.31 (10H, m).

98) ¹H-NMR (CDCl₃) δ; 0.81-2.98 (5H, m), 2.35, 2.37, 2.43, 2.49 (9H, each s), 3.02-4.75 (6H, m), 6.61 (1H, dd, J=18 Hz, 8.4 Hz), 6.93 (1H, d, J=8.4 Hz, 2.3 Hz), 7.08-8.40 (9H, m).

99) ¹H-NMR (CDCl₃) δ; 1.33-3.00 (7H, m), 2.41, 2.43, 2.46 (9H, each s), 3.05-5.14 (6H, m), 6.57 (1H, d, J=8.2 Hz), 6.71 (1H, d, J=8.2 Hz), 6.82-8.28 (13H, m).

100) ¹H-NMR (CDCl₃) δ; 0.83-2.52 (4H, m), 2.42, 2.45 (3H, each s), 2.56-5.18 (5H, m), 3.72 (3H, s), 6.57 (1H, d, J=8.3 Hz), 6.87 (1H, d, J=8.3 Hz), 7.06 (1H, dd, J=5.7 Hz, 2.3 Hz), 6.67-8.49 (8H, m).

101) ¹H-NMR (DMSO-d₆) δ; 1.06-2.14 (4H, m), 2.39 (3H, m), 2.48-3.65 (4H, m), 4.21-4.50 (1H, m), 6.75 (1H, d, J=8.2 Hz), 6.94 (1H, d, J=8.2 Hz), 7.07 (1H, dd, J=2.2 Hz, 8.2 Hz), 7.14-7.82 (7H, m), 10.44, 10.64 (1H, each s), 12.42 (1H, brs).

102) ¹H-NMR (CDCl₃+DMSO-d₆) δ; 1.00-2.21 (4H, m), 2.54-2.99 (2H, m), 2.42, 2.49 (3H, each s), 3.00-5.14 (3H, m), 6.78-8.23 (11H, m), 10.04, 10.29 (1H, each s).

103) ¹H-NMR (CDCl₃) δ; 1.05-2 23 (4H, m), 2.24-5.07 (5H, m), 2.43, 2.49 (3H, each s), 3.71 (3H, s), 6.75-9.00 (11H, m).

104) ¹H-NMR (CDCl₃)δ; 0.78-2.31 (4H, m), 2.48-3.35 (3H, m), 3.36-5.39 (2H, m), 3.73, 3.75 (each 3H, each s), 6.61 (1H, d, J=8.3 Hz), 6.35-7.93 (8H, m), 8.35 (1H, d, J=8.4 Hz), 8.61, 8.86 (1H, each s).

105) ¹H-NMR (CDCl₃) δ; 1.03-2.28 (4H, m), 2.50-3.33 (3H, m), 3.34-5.48 (2H, m), 3.73, 3.75 (each 3H, each s), 6.62 (1H, d, J=8.3 Hz), 6.43-7.82 (8H, m), 8.18-8.70 (2H, m).

106) ¹H-NMR (CDCl₃) δ; 1.02-2.30 (4H, m), 2.49-3.40 (3H, m), 3.41-5.42 (2H, m), 3.73 (3H, s), 6.61 (1H, d, J=8.2 Hz), 6.34-7.99 (8H, m), 8.33 (1H, d, J=8.3 Hz), 8.61, 8.86 (1H, each s).

107) ¹H-NMR (CDCl₃) δ; 0.98-2.35 (4H, m), 2.36-5.47 (5H, m), 3.72 (3H, s), 6.61 (1H, d, J=8.2 Hz), 6.47-7.91 (9H, m), 8.12-8.72 (1H, m).

108) ¹H-NMR (CDCl₃) δ; 1.20-3.18 (11H, m), 2.33 (3H, s), 2.47 (3H, s), 2.48 (3H, s), 3.20-5.12 (6H, m), 6.40-7.93 (11H, m).

109) ¹H-NMR (CDCl₃) δ; 1.21-2.22 (2H, m), 2.35-3.21 (3H, m), 2.98 (3H, s), 2.48 (3H, s), 2.98 (3H, s), 3.15 (3H, s), 3.45-4.63 (4H, m), 6.47-7.83 (11H, m).

110) ¹H-NMR (CDCl₃) δ; 1.42-2.95 (16H, m), 2.40 (3H, s), 2.46 (3H, s), 3.35-4.45 (3H, m), 4.50-5.03 (2H, m), 6.51-8.02 (11H, m).

111) ¹H-NMR (CDCl₃) δ; 1.43-2.96 (12H, m), 7.42 (3H, s), 2.47 (3H, s), 3.36-3.83 (7H, m), 4.32-5.08 (2H, m), 6.51-7.76 (11H, m).

112) ¹H-NMR (CDCl₃)δ; 1.42-2.60 (9H, m), 2.45 (3H, s), 2.66-3.83 (4H, m), 4.03-5.13 (3H, m), 6.50-8.39 (14H, m).

113) ¹H-NMR (CDCl₃)δ; 1.10-1.38 (1H, m), 1.23 (6H, d, J=5.6 Hz), 1.53-2.09 (3H, m), 2.13-3.46 (3H, m), 2.53 (3H, s), 3.56-4.52 (6H, m), 6.32-8.21 (12H, m).

114) ¹H-NMR (CDCl₃) δ; 1.45-2.10 (3H, m), 2.13-3.40 (4H, m), 2.39 (3H, d, J=4.7 Hz), 2.53 (3H, s), 3.42-4.68 (5H, m), 6.38-7.59 (10H, m), 7.79 (1H, brs), 8.16 (1H, brs).

115) ¹H-NMR (CDCl₃) δ; 1.13-2.21 (3H, m), 2.41-3.24 (2H, m), 2.45 (3H, s), 2.99, 3.14 (total 6H, s), 3.47-4.65 (4H, m), 6.53-8.14 (11H, m).

116) ¹H-NMR (CDCl₃) δ; 1.06-2.54 (8H, m), 2.33 (3H, s), 2.45 (3H, s), 2.57-5.02 (12H, m), 6.53-8.38 (11H, m).

117) ¹H-NMR (CDCl₃) δ; 1.42-2.36 (14H, m), 2.36 (3H, s), 2.46 (3H, s), 2.86-3.96 (5H, m), 4.43-5.03 (1H, m), 6.52-8.33 (11H, m), 6.54-7.58 (10H, m), 7.80 (1H, brs). 118) ¹H-NMR (CDCl₃) δ; 1.37-2.90 (15H, m), 2.33 (3H, s), 2.47 (3H, s), 3.38-3.99 (5H, m), 4.31-5.08 (2H, m), 6.56-7.98 (11H, m).

119) ¹H-NMR (CDCl₃) δ; 1.20-2.81 (9H, m), 2.33 (3H, s), 2.47 (3H, s), 2.85-3.93 (7H, m), 4.43-5.21 (1H, m), 6.53-6.87 (3H, m), 7.15-7.86 (9H, m).

120) ¹H-NMR (CDCl₃) δ; 1.22-2.21 (4H, m), 2.42-3.24 (3H, m), 2.47 (3H, s), 2.98 (3H, s), 3.15 (3H, s), 3.58-4.03 (1H, m), 4.40-5.22 (1H, m), 6.53-6.72 (3H, m), 7.13-7.67 (9H, m).

121) ¹H-NMR (CDCl₃) δ; 1.21-2.23 (8H, m), 2.40-4.10 (7H, m), 2.47 (3H, s), 4.35-5.22 (2H, m), 6.53-6.85 (3H, m), 7.13-7.70 (9H, m).

122) ¹H-NMR (CDCl₃) δ; 1.08-2.63 (9H, m), 2.32, 2.34 (total 3H, s), 2.63-4.11 (10H, m), 4.35-5.06 (1H, m), 6.53-8.24 (11H, m).

123) ¹H-NMR (CDCl₃) δ; 1.11-2.28 (4H, m), 2.45-3.23 (3H, m), 3.01 (3H, s), 3.16 (3H, s), 3.45-4.15 (4H, m), 4.38-5.07 (1H, m), 6.53-8.16 (11H, m)

124) ¹H-NMR (CDCl₃)δ; 1.06-2.23 (8H, m), 2.50-4.12 (7H, m), 3.76 (3H, s), 4.34-5.10 (2H, m), 6.52-8.23 (11H, m).

125) ¹H-NMR (CDCl₃) δ; 1.04-2.10 (8H, m), 2.16-3.25 (6H, m), 2.28 (3H, s), 2.30 (3H, s), 2.44, 2.51 (total 3H, s), 3.36-4.18 (5H, m), 4.32-5.02 (2H, m), 6.50-7.90 (10H, m), 8.32, 8.64 (total 1H, brs).

126) ¹H-NMR (CDCl₃) δ; 1.06-2.17 (10H, m), 2.45, 2.51 (total 3H, s), 2.47-3.06 (2H, m), 3.13-4.06 (8H, m), 4.30–5.00 (2H, m), 6.52–7.82 (10H, m), 8.36, 8.72 (total 1H, brs).

127) $^1$H-NMR (CDCl$_3$) δ; 1.12–2.20 (8H, m), 1.91, 1.93 (total 3H, s), 2.34∝3.41 (5H, m), 2.44 (3H, m), 3.55–4.13 (3H, m), 4.32–5.25 (2H, m), 5.96–7.55 (11H, m), 8.16, 8.23 (total 1H, brs), 8.52 (1H brs).

128) $^1$H-NMR (CDCl$_3$) δ; 1.06–2.20 (8H, m), 1 92, 1.93 (total 3H, s), 2.36–3.30 (5H, m), 2.43, 2.52 (total 3H, m), 3.46–4.09 (6H, m), 4.35–5.03 (1H, m), 6.00–7.58 (10H, m), 8.25 (1H, brs), 8.44 (1H, brs).

129) $^1$H-NMR (CDCl$_3$) δ; 1.06–2.25 (8H, m), 1.90 (3H, s), 2.35–1.30 (5H, m), 3.36–4.07 (7H, m), 4.30–4.97 (1H, m), 6.23–7.92 (10H, m), 8.83 (1H, brs), 9.90 (1H, brs).

130) $^1$ H-NMR (CDCl$_3$) δ; 1.28–2.55 (12H, m), 2.34 (3H, s), 2.42 (3H, s), 2.65–2.94 (2H, m), 3.03–3.98 (5H, m), 4.35–5.03 (2H, m), 6.50–8.54 (11H, m).

131) $^1$H-NMR (CDCl$_3$) δ; 1.22–3.04, 3.15–3.89 (total 25H, m), 4.65–5.21 (1H, m), 5.86–6.33 (1H, m), 6.49–7.78 (8H, m), 8.01–8.52 (2H, m).

132) $^1$H-NMR (CDCl$_3$) δ; 1.23–3.23 (7H, m), 2.35 (3H, m), 4.64–5.01 (1H, m), 6.32 (1H, dd, J=2.6 Hz, 8.4 Hz), 6.50 (1H, d, J=8.4 Hz), 6.66 (1H, d, J=2.6 Hz), 7.08 (2H, d, J=8.6 Hz), 7.14–7.80 (4H, m), 7.54 (2H, d, J=8.4 Hz), 9.40 (1H, brs), 10.32 (1H, s).

133) $^1$H-NMR (CDCl$_3$) δ; 1.25–3.36 (11H, m), 2.31 (6H, s), 2.40 (3H, s), 3.92 (2H, t, J=5.0 Hz), 4.77–5.00 (1H, m), 6.42 (1H, dd, J=2.1 Hz, 6.9 Hz), 6.52 (1H, d, J=6.9 Hz), 6.75 (1H, d, J=2.1 Hz), 6.98–7.61 (8H, m), 8.42 (1H, s).

134) $^1$H-NMR (CDCl$_3$) δ; 1.35–3.16 (9H, m), 1.91 (3H, s), 2.43 (3H, m), 3.25–3.58 (2H, m), 3.76–4.12 (2H, m), 4.80–5.09 (1H, m), 5.06 (1H, brs), 6.42 (1H, dd, J=2.2 Hz, 6.8 Hz), 6.56 (1H, d, J=6.8 Hz), 6.74 (1H, d, J=2.2. Hz), 6.98–7.64 (8H, m), 7.96 (1H, s).

135) $^1$H-NMR (CDCl$_3$) δ; 1.17–2.17 (4H, m), 2.43 (3H, s), 2.53–3.21 (3H, m), 3.31–3.82 (1H, m), 3.71 (3H, s), 4.31–5.20 (1H, m), 6.50–6.73 (2H, m), 6.77–7.53 (8H, m), 7.99, 8.00, 8.08 (total 1H, brs).

136) $^1$H-NMR (CDCl$_3$) δ; 1.18–2.15 (4H, m), 2.34 (3H, s), 2.52–3.27 (3H, m), 3.47–3.73 (1H, m), 4.22–5.18 (1H, m), 6.50–6.72 (2H, m), 6.78–6.94 (1H, m), 7.07–7.50 (7H, m), 8.45 (2H, brs).

137) $^1$H-NMR (CDCl$_3$) δ; 1.11–2.23 (7H, m), 2.45 (3H, s), 2.46 (3H, s), 2.63–3.82 (4H, m), 4.10–5.20 (3H, m), 6.55–7.83 (10H, m).

138) $^1$H-NMR (CDCl$_3$)δ; 1.13–2.09 (4H, m), 2.36 (6H, s), 2.56–3.68 (4H, m), 4.28–5.13 (1H, m), 5.92 (1H, brs), 6.55–7.66 (10H, m), 8.17 (1H, brs).

139) $^1$H-NMR (CDCl$_3$) δ; 1.12–1.41 (4H, m), 1.43–2.18 (3H, m), 2.28–3.03 (3H, m), 2.44 (3H, s), 3.32–3.90 (1H, m), 3.60 (3H, s), 4.02–4.96 (3H, m), 6.55–7.56 (10H, m), 8.53 (1H, brs).

140) $^1$H-NMR (CDCl$_3$) δ; 1.10–2.12 (4H, m), 2.53–3.03 (3H, m), 3.34–3.95 (1H, m), 4.27–4.95 (1H, m), 6.53–7.70 (10H, m), 8.57, 8.59, 8.86 (total 1H, brs).

141) $^1$H-NMR (CDCl$_3$) δ; 1.13–2.13 (4H, m), 2.45 (3H, s), 2.53–3.14 (3H, m), 3.27–4.10 (4H, m), 4.30–5.02 (1H, m), 6.52–7.05 (5H, m), 7.07–7.53 (5H, m), 8.70 (1H, brs), 9.13 (1H, brs).

142) $^1$H-NMR (CDCl$_3$) δ; 1.08–2.15 (4H, m), 2.50–3.12 (3H, m), 3.25–4.02 (4H, m), 4.28–5.00 (1H, m), 6.52–7.05 (5H, m), 7.11–7.67 (5H, m), 8.91 (1H, brs), 9.13 (1H, brs).

143) $^1$H-NMR (CDCl$_3$) δ; 1.12–2.75 (16H, m). 2.76–3.92 (3H, m), 3.93–4.42 (1H, m), 6.32–8.25 (15H, m).

144) $^1$H-NMR (CDCl$_3$) δ; 1.47–2.17 (3H, m), 2.32–2.92 (8H, m), 2.92–4.57 (6H, m), 5.17 (1H, brs), 5.76 (1H, brs), 6.17–8.14 (12H, m).

145) $^1$H-NMR (DMSO-d$_6$) δ; 1.38–5.08 [25H, m (2.36, s-like)], 6.60–9.20 (12H, m), 10.29, 10.43 (total 1H, brs).

146) $^1$H-NMR (DMSO-d$_6$) δ; 0.91–2 16 (4H, m) 2.22–4.98 (8H, m), 6.61–7.85 (12H, m), 10.35–10.81 (1H, m).

EXAMPLE 223

In a solution of 5-hydroxymethyl-7-chloro-1-[4-(2-methylbenzoylamino)benzoyl]-2,3,4,5-tetrahydro-1H-benzazepine (0.4 g) in chloroform (10 ml) are dissolved with heating dimethylaminopyridine (0.41 g) and dimethylaminopyridine hydrochloride (0.35 g), and thereto is added N,N-dimethylglycine hydrochloride (0.15 g) at room temperature with stirring, and further added dicyclohexylcarbodiimide (0.46 g). The mixture is stirred at room temperature overnight. To the mixture are added methanol (1.3 ml) and acetic acid (0.4 ml), and the mixture is stirred at room temperature for two hours. Saturated aqueous sodium hydrogen carbonate solution is added to the reaction solution, and the mixture is extracted with dichloromethane, and the extract is dried over magnesium sulfate. The solvent is distilled off under reduced pressure, and the resulting residue is purified by silica gel column chromatography (eluent; methyl acetate), and thereto is added a mixture of hydrochloric acid/methanol. The mixture is stirred at room temperature for one hour to give 5-[(2-dimethylaminoacetyloxy)methyl]-7-chloro-1-[4-(2-methylbenzoylamino)benzoyl]-2,3,4,5-tetrahydro-1H-benzazepine hydrochloride (0.36 g) as colorless amorphous.

$^1$H-NMR (DMSO-d$_6$) δ; 1.2–2.2 (3H, m), 2.35 (3H, s), 2.83 (6H, s), 2.7–3.2 (1H, m), 3.3–3.6 (3H, m), 4.29 (2H, s), 4.2–5.1 (2H, m), 6.80 (1H, d, J=8.2 Hz), 7.0–7.8 (10H, m), 10.4–10.6 (1H, m), 10.6–10.9 (1H, br).

EXAMPLE 224

To a solution of 5-ethoxycarbonylmethoxy-7-chloro-1-[4-(2-methylbenzoylamino)benzoyl]-2,3,4,5-tetrahydro-1H-benzazepine (2.2 g) in tetrahydrofuran (50 ml) is added with stirring lithium borohydride (0.28 g) at room temperature, and the mixture is refluxed for 30 minutes. The reaction solution is poured into diluted hydrochloric acid and extracted with dichloromethane. The extract is dried over magnesium sulfate and the solvent is distilled off under reduced pressure. The resulting residue is purified by silica gel column chromatography (eluent; dichloromethane:methanol=100:1→50:1), and recrystallized from dichloromethane/diethyl ether to give 5-(2-hydroxyethoxy)-7-chloro-1-[4-(2-methylbenzoylamino)benzoyl]-2,3,4,5-tetrahydro-1H-benzazepine (1.6 g) as white powder, mp. 185°–187.5° C.

EXAMPLE 225

5-[2-(p-Toluenesulfonyloxy)ethoxy]-7-fluoro-1-[2-methoxy-4-(2-methylbenzoylamino)benzoyl]-2,3,4,5-tetrahydro-1H-benzazepine (0.4 g), N-methylpiperazine (0.38 ml) and sodium iodide (0.3 g) are dispersed in dimethylformamide (10 ml), and the mixture is stirred at room temperature for 3 days. The reaction mixture is concentrated, and thereto is added water. The mixture is extracted with ethyl acetate, and the extract is dried over sodium carbonate, and purified by silica gel column chromatography (eluent; dichloromethane:methanol=10:1) to give 5-[2-(4-methyl-1-piperazinyl)- ethoxy]-7-fluoro-1-[2-methoxy-4-(2-methylbenzoylamino)benzoyl]-2,3,4,5-tetrahydro-1H-benzazepine (0.15 g) as colorless amorphous.

$^1$H-NMR (CDCl$_3$) δ; 1.37–2.90 (15H, m), 2.33 (3H, s), 2.47 (3H, s), 3.38–3.99 (5H, m), 4.31–5.08 (2H, m), 6.56–7.98 (11H, m).

EXAMPLE 226

To a solution of 5-[2-(p-toluenesulfonyloxy)ethyl]-7-chloro-1-[2-methyl-4-(2-methylbenzoylamino)benzoyl]-2,3,4,5-tetrahydro-1H-benzazepine (0.25 g) in dry dimethylformamide (20 ml) are added sodium iodide (0.178 g) and 4-acetylpiperazine (0.152 g), and the mixture is stirred at room temperature for one hour. The mixture is heated at 50° C. for 2 hours, and further at 60° C. for 3 hours. To the reaction solution are added 1N-hydrochloric acid and diethyl ether, and the aqueous layer is collected and neutralized with saturated aqueous sodium hydrogen carbonate solution, and extracted with dichloromethane. The dichloromethane layer is washed with water, dried, and the solvent is distilled off. To the resulting residue is added hydrochloric acid/ethanol to give 5-[2-(4-acetyl-1-piperazinyl)ethyl]-7-chloro-1-[2-methyl-4-(2-methylbenzoylamino)benzoyl]-2,3,4,5-tetrahydro-1H-benzazepine hydrochloride (150 mg) as colorless amorphous.

$^1$H-NMR (DMSO-d$_6$) δ; 1.02–2.59 [16H, m (2.09, 3H, s-like)], 2.59–3.83 (9H, m), 3.87–4.63 (2H, m), 6.56–8.12 (10H, m), 10.27, 10.45 (total 1H, brs), 11.00 (1H, brs).

PHARMACOLOGICAL TEST

Experiment 1: V$_1$ Receptor Binding Assay

Using rat liver plasma membrane preparations prepared according to Ichihara's method [cf: Akira Ichihara, J. Bio. Chem., 258, 9283 (1983)], the plasma membrane (50000 dpm, 2×10$^{-10}$M) of [$^3$H]-Arg-vasopressin and a test compound (60 μg, 10$^{-8}$–10$^{-4}$M) are incubated at 37° C. for 10 minutes in 100 mM Tris-HCl buffer pH: 8.0 (250 μl) containing 5 mM MgCl$_2$, 1 mM EDTA and 0.1 % BSA. After incubation, the mixture is filtered three times using the glass filter (GF/F) so as to separate the membrane preparation combining with vasopressin and then washed with the buffer (5 ml). This glass filter is taken out and mixed with liquid scintillation cocktail. The amount of [$^3$H]-vasopressin combining with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

$C_1$: The amount of [$^3$H]-vasopressin combining with the membrane in the presence of the test compound of a known amount.

$C_0$: The amount of [$^3$H]-vasopressin combining with the membrane in the absence of the test compound.

$B_1$: The amount of [$^3$H]-vasopressin combining with the membrane in the presence of the excess amount of vasopressin (10$^{-6}$M).

The results are expressed as IC$_{50}$ value, which is the concentration of the test compound required to achieve the inhibitory effect in the rate of 50%.

The results are shown in the following Table 3.

TEST COMPOUNDS 1. 5-Dimethylamino-1-[4-(3-carbamoylbenzoylamino)benzoyl]- 2,3,4,5-tetrahydro-1H-benzazepine
2. 5-Dimethylamino-1-{4-[2-(2-methylphenyl)acetylamino]benzoyl}-2,3,4,5-tetrahydro-1H-benzazepine
3. 5-Dimethylamino-1-{4-[2-(2-chlorophenyl)acetylamino]benzoyl}-2,3,4,5-tetrahydro-1H-benzazepine
4. 5-Dimethylamino-1-{4-[2-(2-methoxyphenyl)acetylamino]benzoyl}-2,3,4,5-tetrahydro-1H-benzazepine
5. 5-Dimethylamino-1-{4-[2-(2-fluorophenyl)acetylamino]benzoyl}-2,3,4,5-tetrahydro-1H-benzazepine
6. 5-Dimethylamino-1-{4-[2-(2,6-dichlorophenyl)acetylamino]benzoyl}-2,3,4,5-tetrahydro-1H-benzazepine
7. 5-Dimethylamino-1-{4-[2-(2-nitrophenyl)acetylamino]benzoyl}-2,3,4,5-tetrahydro-1H-benzazepine
8. 5-Dimethylamino-7-hydroxy-1-[2-chloro-4-(2-chlorobenzoylamino)benzoyl]-2,3,4,5-tetrahydro-1H-benzazepine
9. 5-(L-Alanyloxy)-1-[2-chloro-4-(2-methylbenzoylamino)benzoyl]-2,3,4,5-tetrahydro-1H-benzazepine hydrochloride
10. 5-(L-Methionyloxy)-1-[2-chloro-4-(2-methylbenzoylamino)benzoyl]-2,3,4,5-tetrahydro-1H-benzazepine hydrochloride
11. 5-Dimethylamino-7-acetyloxy-1-[2-chloro-4-(2-chlorobenzoyl)-2,3,4,5-tetrahydro-1H-benzazepine
12. 5-(L-Prolyloxy)-1-[2-chloro-4-(2-methylbenzoylamino)benzoyl]-2,3,4,5-tetrahydro-1H-benzazepine hydrochloride (Example 64)
13. 5-(L-Methionyloxy)-7-chloro-1-[2-methoxy-4-(2-methylbenzoylamino)benzoyl]-2,3,4,5-tetrahydro-1H-benzazepine hydrochloride (Example 61)
14. 5-(L-Methionyloxy)-7-chloro-1-[2-methyl-4-(2-methylbenzoylamino)benzoyl]-2,3,4,5-tetrahydro-1H-benzazepine hydrochloride (Isomer A of Example 72)
15. 5-(L-Valyloxy)-7-chloro-1-[2-methyl-4-(2-methylbenzoylamino)benzoyl]-2,3,4,5-tetrahydro-1H-benzazepine hydrochloride (Isomer A of Example 86).
16. 5-Hydroxy-7-chloro-1-{2-methyl-4-[2-(2-methylphenyl)acetylamino]benzoyl}-2,3,4,5-tetrahydro-1H-benzazepine
17. 5-(2-Morpholinoacetyloxy)-7-chloro-1-[2-methoxy-4-(2-methylbenzoylamino)benzoyl]-2,3,4,5-tetrahydro-1H-benzazepine hydrochloride
18. 5-Hydroxy-7-chloro-1-{2-methoxy-4-[2-(2-methylphenyl)acetylamino]benzoyl}-2,3,4,5-tetrahydro-1H-benzazepine
19. 5,7-Dihydroxy-5-hydroxymethyl-1-[2-chloro-4-(2-chlorobenzoylamino)benzoyl]-2,3,4,5-tetrahydro-1H-benzazepine
20. 5-Dimethylamino-7-dimethylaminocarbonylmethoxy-1-[2-chloro-4-(2-chlorobenzoylamino)benzoyl]-2,3,4,5 tetrahydro-1H-benzazepine
21. 5-Ethoxycarbonylmethylaminocarbonylmethoxy-7-fluoro- 1-[2-chloro-4-(2-methylbenzoylamino)benzoyl]-2,3,4,5-tetrahydro-1H-benzazepine
22. 5-Carboxymethylaminocarbonylmethoxy-7-fluoro-1-[2-chloro-4-(2-methylbenzoylamino)benzoyl]-2,3,4,5-tetrahydro-1H-benzazepine 23. 5-[(2-β-Methoxycarbonyl)-1-pyrrolidinylcarbonylmethoxy]-7-fluoro-1-[2-chloro-4-(2-methylbenzoylamino)benzoyl]-2,3,4,5-tetrahydro-1H-benzazepine
24. 5-(2-Methoxyacetyloxy)-7-chloro-1-[4-(2-methylbenzoylamino)benzoyl]-2,3,4,5-tetrahydro-1H-benzazepine
25. 5-[2-(Dimethylaminoacetyloxy)methyl]-7-chloro-1-[4-(2-methylbenzoylamino)benzoyl]-2,3,4,5-tetrahydro-1H-benzazepine hydrochloride
26. 5-Ethoxycarbonylmethyl-7-chloro-1-[2-methoxy-4-(2-methylbenzoylamino)benzoyl]-2,3,4,5-tetrahydro-1H-benzazepine
27. 5-[(4-Methyl-1-piperazinyl)carbonylmethyl]-7-chloro-1-[3-methoxy-4-(2-methylbenzoylamino)benzoyl]-2,3,4,5-tetrahydro-1H-benzazepine
28. 5-Carbamoylmethyl-7-chloro-1-[2-ethoxy-4-(2-chlorobenzoylamino)benzoyl]-2,3,4,5-tetrahydro-1H-benzazepine
29. 5-(L-Lysyloxy)-7-chloro-1-[2-methoxy-4-(2-methylbenzoylamino)benzoyl]-2,3,4,5-tetrahydro-1H-benzazepine dihydrochloride
30. 5-[(4-Piperidinyl)aminocarbonylmethyl]-7-chloro-1-[3-methoxy-4-(2-methylbenzoylamino)benzoyl]-2,3,4,5-tetrahydro-1H-benzazepine hydrochloride
31. 5-Carboxymethyl-7-chloro-1-[2-methoxy-4-(2-chlorobenzoylamino)benzoyl]-2,3,4,5-tetrahydro-1H-benzazepine
32. 5-Dimethylaminocarbonylmethyl-7-chloro-1-[3-methoxy-4-(2-methylbenzoylamino)benzoyl]-2,3,4,5-tetrahydro-1H-benzazepine
33. 5-(3-Dimethylaminopropylidene)-7-fluoro-1-[2-chloro-4-(2-methylbenzoylamino)benzoyl]-2,3,4,5-tetrahydro-1H-benzazepine hydrochloride
34. 5-[2-(1-Pyrrolidinyl)ethoxy]-7-chloro-1-[2-methoxy-4-(2-methylbenzoylamino)benzoyl]-2,3,4,5-tetrahydro-1H-benzazepine hydrochloride
35. 5-(3-Morpholinopropoxy)-7-fluoro-1-[2-methyl-4-(2-methylbenzoylamino)benzoyl]-2,3,4,5-tetrahydro-1H-benzazepine
36. 5-[3-(1-Imidazolyl)propoxy]-7-fluoro-1-[2-methyl-4-(2-methylbenzoylamino)benzoyl]-2,3,4,5-tetrahydro-1H-benzazepine
37. 5-[3-(p-Toluenesulfonyloxy)propoxy]-7-chloro-1-[2-methoxy-4-(2-methylbenzoylamino)benzoyl]-2,3,4,5-tetrahydro-1H-benzazepine
38. 5-Cyano-7-chloro-1-[3-chloro-4-(2-methylbenzoylamino)benzoyl]-2,3,4,5-tetrahydro-1H-benzazepine
39. 5-Cyanomethyl-7-chloro-1-[3-methoxy-4-(2-methylbenzoylamino)benzoyl]-2,3,4,5-tetrahydro-1H-benzazepine
40. 5-[2-(4-Acetyl-1-piperazinyl)ethoxy]-7-chloro-1-[2-methoxy-4-(2-methylbenzoylamino)benzoyl]-2,3,4,5-tetrahydro-1H-benzazepine hydrochloride
41. 5-[(4-Methyl-1-piperazinyl)carbonylmethyl]-7-chloro-1-[2-methyl-4-(2-methylbenzoylamino]benzoyl]-2,3,4,5-tetrahydro-1H-benzazepine
42. 5-Methylaminocarbonylmethyl-7-fluoro-1-[2-methoxy-4-(2-methylbenzoylamino)benzoyl]-2,3,4,5-tetrahydro-1H-benzazepine
43. 5-[2-(1-Piperazinyl)ethoxy]-7-chloro-1-[2-methoxy-4-(2-methylbenzoylamino)benzoyl]-2,3,4,5-tetrahydro-1H-benzazepine dihydrochloride
44. 5-[(4-Methyl-1-piperazinyl)carbonylmethyl]-7-chloro-1-[2-methoxy-4-(2-chlorobenzoylamino)benzoyl]-2,3,4,5-tetrahydro-1H-benzazepine hydrochloride
45. 5-[(4-Dimethylamino-1-piperidinyl)carbonylmethyl]-7-chloro-1-[2-methoxy-4-(2-chlorobenzoylamino)benzoyl]-2,3,4,5-tetrahydro-1H-benzazepine hydrochloride
46. 5-[(4-Methyl-1-piperazinyl)methyl]-7-fluoro-1-[2-methoxy-4-(2-methylbenzoylamino)benzoyl]-2,3,4,5-tetrahydro-1H-benzazepine
47. 5-[2-(4-Methyl-1-piperazinyl)ethoxy]-7-fluoro-1-[2-methoxy-4-(2-methylbenzoylamino)benzoyl]-2,3,4,5-tetrahydro- 1H-benzazepine
48. 5-[(1-Benzyl-4-piperidinyl)aminocarbonylmethyl]-7-chloro-1-[2-methoxy-4-(2-chlorobenzoylamino)benzoyl]-2,3,4,5-tetrahydro-1H-benzazepine hydrochloride
49. 7-Chloro-1-[2-methoxy-4-{2-[4-(4-acetyl-1-[4-(2-methylbenzoylamino}benzoly]-2,3,4,5-tetrahydro-1H-benzazepine
50. 5-[(1-Pyrrolidinyl)carbonylmethyl]-7-fluoro-1-[4-(2-methylbenzoylamino)benzoyl]-2,3,4,5-tetrahydro-1H-benzazepine
51. 5-Dimethylaminocarbonylmethyl-7-fluoro-1-[2-methoxy-4-(2-bromobenzoylamino)benzoyl]-2,3,4,5-tetrahydro-1H-benzazepine
52. 5-[(1-Piperazinyl)carbonylmethyl]-7-chloro-1-[2-methoxy-4-(2-methylbenzoylamino)benzoyl]-2,3,4,5-tetrahydro-1H-benzazepine hydrochloride
53. 5-[2-(1-Acetyl-1-piperazinyl)ethyl]-7-chloro-1-[2-methyl-4-(2-methylbenzoylamino)benzoyl]-2,3,4,5-tetrahydro-1H-benzazepine hydrochloride
54. 5-[2-(4-Dimethylamino-1-piperidinyl)ethyl]-7-chloro-1-[2-methoxy-4-(2-methylbenzoylamino)benzoyl]-2,3,4,5-tetrahydro-1H-benzazepine dihydrochloride
55. 5-[2-(4-Methyl-1-piperazinyl)ethyl]-7-chloro-1-[2-methoxy-4-(2-methylbenzoylamino)benzoyl]-2,3,4,5-tetrahydro-1H-benzazepine dihydrochloride
56. 7-Chloro-1-[3-methoxy-4-{2-[4-(4-acetyl-1-piperazinyl)butoxy] benzoylamino}benzoyl]-2,3,4,5-tetrahydro-1H-benzazepine
57. 7-Chloro-5-[(4-piperidinyl)aminocarbonylmethoxy]-1-[2-methyl-4-(2-methylbenzoylamino)benzoyl]-2,3,4,5-tetrahydro-1H-benzazepine hydrochloride
58. 5-[(1-piperidinyl)carbonylmethyl]-7-fluoro-1-[2-methoxy-4-(2-methylbenzoylamino)benzoyl]-2,3,4,5-tetrahydro-1H-benzazepine
59. 5-[(1-Methyl-4-piperidinyl)aminocarbonyl-methoxy]-7-chloro-1-[2-methyl-4-(2-methylbenzoylamino)benzoyl]-2,3,4,5-tetrahydro-1H-benzazepine
60. 5-[(4-Acetylamino-1-piperidinyl)carbonylmethyl]-7-fluoro-1-[2-methoxy-4-(2-bromobenzoylamino)benzoyl]-2,3,4,5-tetrahydro-1H-benzazepine
61. 5-(2-Hydroxyethoxy)-7-chloro-1-[4-(2-methylbenzoylamino)benzoyl]-2,3,4,5-tetrahydro-1H-benzazepine
62. 5-(Carbamoylmethylaminocarbonylmethyl)-7-chloro-1-[2-methyl-4-(2-methylbenzoylamino)benzoyl]-2,3,4,5-tetrahydro-1H-benzazepine
63. 5-[(4-Methyl-1-piperazinyl)carbonylmethyl]-7-chloro-1-[2-methoxy-4-(2-methylbenozylamino)benzoyl]-2,3,4,5-tetrahydro-1H-benzazepine

TABLE 3

| Test Comp. No. | IC$_{50}$ (μM) | Test Comp. No. | IC$_{50}$ (μM) |
|---|---|---|---|
| 6 | 0.12 | 13 | 0.020 |
| 14 | 0.22 | 15 | 0.18 |
| 16 | 0.32 | 17 | 0.021 |
| 18 | 0.055 | 24 | 0.018 |

TABLE 3-continued

| Test Comp. No. | IC$_{50}$ ($\mu$M) | Test Comp. No. | IC$_{50}$ ($\mu$M) |
| --- | --- | --- | --- |
| 25 | 0.021 | 26 | 0.077 |
| 27 | 0.034 | 28 | 0.030 |
| 29 | 0.04 | 30 | 0.031 |
| 32 | 0.011 | 33 | 0.084 |
| 34 | 0.009 | 37 | 0.21 |
| 38 | 0.16 | 39 | 0.044 |
| 40 | 0.073 | 42 | 0.16 |
| 43 | 0.070 | 44 | 0.024 |
| 45 | 0.008 | 46 | 0.089 |
| 47 | 0.33 | 48 | 0.037 |
| 50 | 0.11 | 51 | 0.018 |
| 52 | 0.016 | 54 | 0.054 |
| 55 | 0.062 | 56 | 0.007 |
| 58 | 0.095 | 60 | 0.045 |
| 61 | 0.019 | 63 | 0.030 |

Experiment 2: V$_2$ Receptor Binding Assay

Using rat kidney plasma membrane preparations prepared according to O. Hechter's method [cf: J. Bio. Chem., 253, 3211 (1978)], the plasma membrane (100000 dpm, 4×10−10M) of [$^3$H]-Arg-vasopressin and a test compound (0.6 mg, 10$^{-10}$−10$^{-5}$M) are incubated at 4° C. for 3 hours in 100 mM Tris-HCl buffer pH: 8.0 (250 $\mu$l) containing 5 mM MgCl$_2$, 1 mM EDTA and 0.1 % BSA. After incubation, the mixture is filtered using the glass filter (GF/F) so as to separate the membrane preparation combining with vasopressin and then washed twice with the buffer (5 ml). This glass filter is taken out and mixed with liquid scintillation cocktail. The amount of [$^3$H]-vasopressin combining with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_1} \times 100$$

C$_1$: The amount of [$^3$H]-vasopressin combining with the membrane in the presence of the test compound of a known amount.

C$_0$: The amount of [$^3$H]-vasopressin combining with the membrane in the absence of the test compound.

B$_1$: The amount of [3H-vasopressin combining with the membrane in the presence of the excess amount of vasopressin (10$^{-6}$M).

The results are expressed as IC$_{50}$ value, which is the concentration of the test compound required to achieve the inhibitory effect in the rate of 50%.

The results are shown in the following Table 4.

TABLE 4

| Test Comp. No. | IC$_{50}$ ($\mu$M) | Test Comp. No. | IC$_{50}$ ($\mu$M) |
| --- | --- | --- | --- |
| 1 | 0.56 | 2 | 0.018 |
| 3 | 0.061 | 4 | 0.061 |
| 5 | 0.059 | 6 | 0.024 |
| 7 | 0.14 | 8 | 0.25 |
| 9 | 0.017 | 10 | 0.083 |
| 11 | 0.11 | 12 | 0.009 |
| 13 | 0.006 | 14 | 0.011 |
| 15 | 0.014 | 16 | 0.004 |
| 17 | 0.012 | 18 | 0.004 |
| 19 | 2.8 | 20 | 5.6 |
| 21 | 0.006 | 22 | 0.018 |
| 23 | 0.011 | 24 | 0.007 |
| 25 | 0.004 | 26 | 0.009 |
| 27 | 0.007 | 28 | 0.002 |
| 29 | 0.006 | 30 | 0.009 |
| 31 | 0.019 | 32 | 0.004 |
| 33 | 0.002 | 34 | 0.006 |
| 35 | 0.0062 | 36 | 0.0076 |
| 37 | 0.0054 | 38 | 0.15 |
| 39 | 0.014 | 40 | 0.007 |
| 41 | 0.013 | 42 | 0.006 |
| 43 | 0.006 | 44 | 0.006 |
| 45 | 0.004 | 46 | 0.009 |
| 47 | 0.008 | 48 | 0.012 |
| 49 | 0.052 | 50 | 0.015 |
| 51 | 0.003 | 52 | 0.006 |
| 53 | 0.029 | 54 | 0.004 |
| 55 | 0.012 | 57 | 0.009 |
| 58 | 0.016 | 59 | 0.009 |
| 60 | 0.010 | 61 | 0.016 |
| 62 | 0.003 | 63 | 0.010 |

Experiment 3: Vasopressin Antagonistic Activity

In order to test the vasopressin antagonistic activity of the compound of the present invention when administered orally to rats under awakening, the following experiment was made. Cannulas were inserted into the aorta abdominalis and the carotid arteries of male SD-rats (body weight; 300–450 g) under pentobarbital-anesthetization. A few days thereafter, vasopressin (30 mU/kg) was administered intravenously to the rats under awakening with measuring the blood pressure at the cannula inserted into the aorta abdominalis by a piezoelectric transducer. The test compound was dissolved in polyethylene glycol or water, or suspended in 5% gum arabic solution, and orally administered by force to the rats.

The increase in the diastolic pressure of the rats was periodically measured at 30 minutes' interval after the administration of vasopressin for 8 hours. The rate of inhibitory effect (%) of the test compound on the increase in the diastolic pressure caused by vasopressin (30 mU/kg) was estimated based on the increase in the diastolic pressure when vasopressin (30 mU/kg) was intravenously administered without a test compound.

The results are expressed as ID$_{50}$ value, which is the oral dose of the test compound required to achieve the inhibitory effect in the rate of 50%.

The results are shown in the following Table 5.

TABLE 5

| Test Compound No. | ID$_{50}$ (mg/kg) |
| --- | --- |
| 63 | 3.4 |

Experiment 4: Water Diuretic Activity in Vivo

The test compound of the present invention was dissolved in polyethylene glycol 400 or water, or suspended in 5% gum arabic solution, and the mixture was orally administered by force to male SD-rats (body weight; 300–400 g) under untreated and unrestrained. After administration, the rats were kept in a metabolism cage and the amount of urine spontaneously excreted by the rats was measured at 2 hours' inteval, during which the rats could freely feed and water.

In the control group, a solvent was administered instead of a test compound solution (or suspension).

The results are expressed as $ED_3$, which is the oral dose of the test compound which is required to increase the amount of the urine excreted in the test compound-treated group for the first 2 hours by three times based on the amount of urine excreted for the first 2 hours in the control group.

The results are shown in the following Table 6.

TABLE 6

| Test Compound No. | $ED_3$ (mg/kg) |
|---|---|
| 41 | 1.4 |
| 63 | 3.2 |

What is claimed is:

1. A benzoheterocyclic compound of the formula:

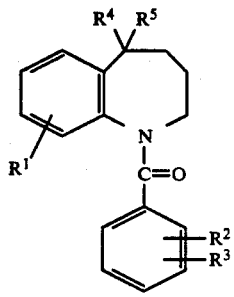

wherein $R^1$ is hydrogen atom; a halogen atom; hydroxy group; a lower alkanoyloxy group; an amino-lower alkoxy group which may optionally be substituted by a group selected from a lower alkyl group and a lower alkanoyl group; a carboxy-substituted lower alkoxy group; a lower alkoxycarbonyl-substituted lower alkoxy group; or an aminocarbonyl-lower alkoxy group which may optionally be substituted by a lower alkyl group, $R^4$ is hydrogen atom; a group of the formula: —$NR^6R^7$ (wherein $R^4$ and $R^7$ are the same or different and are hydrogen atom, a lower alkyl group or a lower alkenyl group); a lower alkenyloxy group; a hydroxy-substituted lower alkyl group; a group of the formula —O—CO—A—$NR^8R^9$ (wherein A is a lower alkylene group, $R^8$ and $R^9$ are the same or different and are hydrogen atom or a lower alkyl group, and $R^8$ and $R^9$ may bind together with the adjacent nitrogen atom to which they bind to form a 5- or 6-membered, saturated or unsaturated heterocyclic ring which may be intervened or not with nitrogen or oxygen atom selected from the group consisting of pyrrolidinyl, piperidinyl, piperazinyl, morpholino, pyrrolyl, imidazolyl, 1,2,4-triazolyl, 1,3,4-triazolyl, pyrazolyl, 2-pyrrolyl, 2-imidazolynyl, imidazolyidinyl, 2-pyrazolynyl, pyrazolydinyl, 1,2-dihydropyridyl and 1,2,3,4-tetrahydropyridyl, wherein said heterocyclic ring may optionally have a lower alkyl substituent); a group of the formula: —O—$R^{10}$ (wherein $R^{10}$ is an amino acid residue); a lower alkoxycarbonyl-substituted lower alkylidene group; a lower alkoxycarbonyl-substituted lower alkyl group; a carboxy-substituted lower alkyl group; a group of the formula: —A—$CONR^{11}R^{12}$ (wherein A is the same as defined above, $R^{11}$ and $R^{12}$ are the same or different and are hydrogen atom, a lower alkyl group, a piperidinyl group which may optionally be substituted by a phenyl-lower alkyl group on the piperidine ring, or a carbamoyl-lower alkyl group, and $R^{11}$ and $R^{12}$ may bind together with the adjacent nitrogen atom to which they bind to form a 5-or 6-membered, saturated heterocyclic ring which may be intervened or not with nitrogen or oxygen atom selected from the group consisting of pyrrolidinyl, piperidinyl, piperazinyl and morpholino, wherein said heterocyclic ring may optionally be substituted by a group selected from a lower alkyl group, a lower alkoxycarbonyl group and an amino group optionally having a substituent selected from a lower alkyl group and a lower alkanoyl group); a group of the formula:

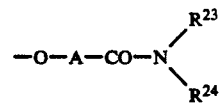

(wherein A is the same as defined above, $R^{23}$ and $R^{24}$ are the same or different and are hydrogen atom, a lower alkoxycarbonyl-substituted lower alkyl group, a carboxy-substituted lower alkyl group, or a piperidinyl group which may optionally be substituted by a lower alkyl group on the piperidine ring); a pyrrolidinylcarbonyl-lower alkoxy group which is substituted by a lower alkoxycarbonyl group on the pyrrolidine ring; a lower alkoxy-substituted lower alkanoyloxy group; a group of the formula:

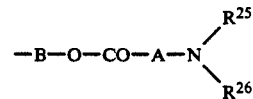

(wherein A is the same as defined above, B is a lower alkylene group, $R^{25}$ and $R^{26}$ are the same or different and are hydrogen atom or a lower alkyl group); an amino-substituted lower alkylidene group wherein the amino moiety may optionally be substituted by a lower alkyl group; a group of the formula:

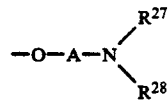

(wherein A is the same as defined above, $R^{27}$ and $R^{28}$ bind together with the adjacent nitrogen atom to which they bind to form a 5- or 10-membered, saturated or unsaturated heteromonocyclic ring or heterodicyclic ring which may be intervened or not with nitrogen or oxygen atom selected from the group consisting of pyrrolidinyl, piperidinyl, piperazinyl, morpholino, imidazolyl, isoindolyl and 1,2,3,4,5,6,7-octahydroisoindolyl, wherein said heterocyclic ring may optionally be substituted by a group selected from an oxo group, a lower alkyl group, a lower alkoxycarbonyl group and a lower alkanoyl group); cyano group; a cyano-substituted lower alkyl group; a lower alkoxy group having a substituent selected from hydroxy group and a phenylsulfonyloxy group optionally being substituted by a lower alkyl group on the phenyl ring; a group of the formula:

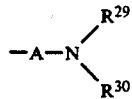

(wherein a is the same as defined above, $R^{29}$ and $R^{30}$ bind together with the adjacent nitrogen atom to which they bind to form a 5- or 6-membered, saturated heterocyclic ring which may be intervened or not with nitrogen or oxygen atom selected from the group consisting of pyrrolidinyl, piperidinyl, piperazinyl and morpholino, wherein said heterocyclic ring may optionally be substituted by a group selected from a lower alkyl group, a lower alkanoyl group and an amino group optionally having a lower alkyl substituent); a phenylsulfonyloxy-substituted lower alkyl group which may optionally be substituted by a lower alkyl group on the phenyl ring; a phthalimido-substituted lower alkyl group; or a cyano-substituted lower alkylidene group, $R^5$ is hydrogen atom or hydroxy group, and $R^4$ and $R^5$ may combine together to form an oxo group, $R^2$ is hydrogen atom, a lower alkyl group, a halogen atom or a lower alkoxy group, $R^3$ is a group of the formula:

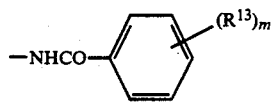

(wherein $R^{13}$ is a halogen atom, carbamoyl group, a lower alkyl group, a piperazinyl-lower alkoxy group which is substituted by a lower alkanoyl group on the 4-position of the piperazine ring, m is 0 or an integer of 1 to 3) or a phenyl-lower alkanoylamino group which is substituted by 1 to 3 groups selected from a halogen atom, a lower alkoxy group, a lower alkyl group and nitro group on the phenyl ring, provided than when $R^1$ is hydrogen atom or a halogen atom, $R^4$ is hydrogen atom, a group of the formula: $-NR^6R^7$ (wherein $R^6$ and $R^7$ are the same as defined above), a group of the formula:

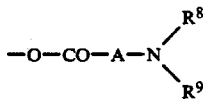

(wherein A is the same as defined, above, and $R^8$ and $R^9$ are the same or different and are hydrogen atom or a lower alkyl group) or a hydroxy-substituted lower alkyl group, and $R^5$ is hydrogen atom, hydroxy group or $R^4$ and $R^5$ combine together to form an oxo group, $R^3$ is a group of the formula:

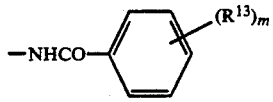

(wherein $R^{13}$ is carbamoyl group, or a piperazinyl-lower alkoxyl group which is substituted by a lower alkanoyl group on the 4-position of the piperazine ring, and m is the same as defined above), or a salt thereof.

2. The benzoheterocyclic compound according to claim 1, wherein $R^1$ is hydrogen atom or a halogen atom, or a salt thereof.

3. The benzoheterocyclic compound according to claim 1, wherein $R^1$ is hydroxy group, a lower alkanoyloxy group, an amino-lower alkoxy group which may optionally be substituted by a group selected from a lower alkyl group and a lower alkanoyl group, a carboxy-substituted lower alkoxy group, a lower alkoxycarbonyl-substituted lower alkoxy group or an aminocarbonyl-lower alkoxy group which may optionally have a lower alkyl substituent, or a salt thereof.

4. The benzoheterocyclic compound according to claim 2, wherein $R^4$ is hydrogen atom; a group of the formula $-NR^6R^7$ (wherein $R^6$ and $R^7$ are the same as defined in claim 1); a lower alkenyloxy group; a lower alkoxycarbonyl-substituted lower alkylidene group; a lower alkoxycarbonyl-substituted lower alkyl group; a carboxy-substituted lower alkyl group; a pyrrolidinylcarbonyl-lower alkoxy group having a lower alkoxycarbonyl substituent on the pyrrolidine ring; a lower alkoxy-substituted lower alkanoyloxy group; an amino-substituted lower alkylidene group wherein the amino moiety may optionally be substituted by a lower alkyl group; cyano group; a cyano-substituted lower alkyl group; a lower alkoxy group having a substituent selected from hydroxy group and a phenylsulfonyloxy group optionally being substituted by a lower alkyl group on the phenyl ring; a phenylsulfonyloxy-substituted lower alkyl group which may optionally be substituted by a lower alkyl group on the phenyl ring; a phthalimido-substituted lower alkyl group; or a cyano-substituted lower alkylidene group, or a salt thereof.

5. The benzoheterocyclic compound according to claim 2, wherein $R^4$ is a hydroxy-substituted lower alkyl group, or a salt thereof.

6. The benzoheterocyclic compound according to claim 2, wherein $R^4$ is a group of the formula: $-O-CO-A-NR^8R^9$ (wherein A, $R^8$ and $R^9$ are the same as in claim 1), or a salt thereof.

7. The benzoheterocyclic compound according to claim 2, wherein $R^4$ is a group of the formula: $-O-R^{10}$ (wherein $R^{10}$ is the same as defined in claim 1), or a salt thereof.

8. The benzoheterocyclic compound according to claim 2, wherein $R^4$ is a group of the formula: $-A-CONR^{11}R^{12}$ (wherein A, $R^{11}$ and $R^{12}$ are the same as defined in claim 1), or a salt thereof.

9. The benzoheterocyclic compound according to claim 2, wherein $R^4$ is a group of the formula:

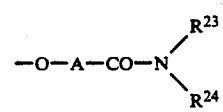

(wherein A, $R^{23}$ and $R^{24}$ are the same as defined in claim 1) or a group of the formula:

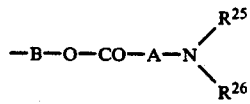

(wherein A, B, $R^{25}$ and $R^{26}$ are the same as defined in claim 1) or a salt thereof.

10. The benzoheterocyclic compound according to claim 2, wherein $R^4$ is a group of the formula:

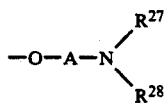

(wherein A, $R^{27}$ and $R^{28}$ are the same as defined in claim 1) or a salt thereof.

11. The benzoheterocyclic compound according to claim 2, wherein $R^4$ is a group of the formula:

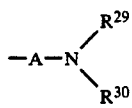

(wherein A, $R^{29}$ and $R^{30}$ are the same as defined in claim 1) or a salt thereof.

12. The benzoheterocyclic compound according to claim 3, wherein $R^4$ is a group of the formula: —A—CO—$NR^{11}R^{12}$ (wherein A, $R^{11}$, $R^{12}$ are the same as defined in claim 1) or a salt thereof.

13. The benzoheterocyclic compound according to claim 3, wherein $R^4$ is a group of the formula:

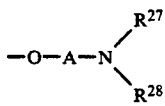

(wherein A, $R^{27}$ and $R^{28}$ are the same as defined in claim 1) or a salt thereof.

14. The benzoheterocyclic compound according to claim 3, wherein $R^4$ is a group of the formula:

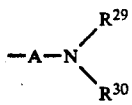

(wherein A, $R^{29}$ and $R^{30}$ are the same as defined in claim 1) or a salt thereof.

15. The benzoheterocyclic compound according to any one of claims 4 to 14, wherein $R^5$ is hydrogen atom, $R^2$ is a lower alkyl group or a lower alkoxy group, and $R^3$ is a group of the formula:

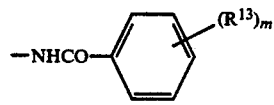

(wherein $R^{13}$ is a halogen atom or a lower alkyl group, and m is the same as defined in claim 1), or a salt thereof.

16. The benzoheterocyclic compound according to any one of claims 4 to 14, wherein $R^5$ is hydrogen atom, $R^2$ is hydrogen atom or a halogen atom, and $R^3$ is a group of the formula:

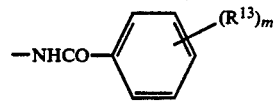

(wherein $R^{13}$ is a halogen atom or a lower alkyl group, and m is the same as defined in claim 1) or a salt thereof.

17. The benzoheterocyclic compound according to any one of claims 4 to 14, wherein $R^5$ is hydrogen atom, $R^2$ is a lower alkyl group or a lower alkoxy group, and $R^3$ is a group of the formula:

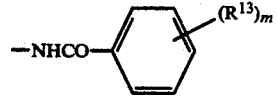

(wherein $R^{13}$ is carbamoyl group or a piperazinyl-lower alkoxy group having a lower alkanoyl substituent on the 4-position of the piperazine ring, and m is the same as defined in claim 1) or a salt thereof.

18. The benzoheterocyclic compound according to any one of claims 4 to 14, wherein $R^5$ is hydrogen atom, $R^2$ is hydrogen atom or a halogen atom, and $R^3$ is a group of the formula:

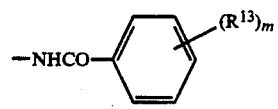

(wherein $R^{13}$ is carbamoyl group or a piperazinyl-lower alkoxy group having a lower alkanoyl substituent on the 4-position of the piperazine ring and m is the same as defined in claim 1), or a salt thereof.

19. The benzoheterocyclic compound according to any one of claim 2 or 3, wherein $R^5$ is hydroxy group, or a salt thereof.

20. The benzoheterocyclic compound according to any one of claim 2 or 3, wherein $R^3$ is a phenyl-lower alkanoylamino group having 1 to 3 substituents selected from a halogen atom, a lower alkoxyl group, a lower alkyl group and nitro group on the phenyl ring, or a salt thereof.

21. The benzoheterocyclic compound according to claim 6, wherein $R^8$ and $R^9$ are the same or different and are hydrogen atom or a lower alkyl group, or a salt thereof.

22. The benzoheterocyclic compound according to claim 6, wherein $R^8$ and $R^9$ bind together with the adjacent nitrogen atom to which they bind to form a 5- or 6-membered, saturated or unsaturated heterocyclic ring which may be intervened or not with nitrogen or oxygen atom, wherein the said heterocyclic ring may optionally have a lower alkyl substituent, or a salt thereof.

23. The benzoheterocyclic compound according to claim 8, wherein $R^{11}$ and $R^{12}$ are the same or different and are hydrogen atom, a lower alkyl group, a piperidinyl group optionally having a phenyl-lower alkyl group on the piperidine ring, or a carbamoyl-lower alkyl group, or a salt thereof.

24. The benzoheterocyclic compound according to claim 8, wherein $R^{11}$ and $R^{12}$ bind together with the adjacent nitrogen atom to which they bind to form a 5- or 6-membered, saturated heterocyclic ring which may be intervened or not with nitrogen or oxygen atom, wherein the said heterocyclic ring may optionally have a substituent selected from a lower alkyl group, a lower alkoxycarbonyl group and an amino optionally being substituted by a group selected from a lower alkyl group and a lower alkanoyl group, or a salt thereof.

25. 7-Chloro-5-[(4-methyl-1-piperazinyl)carbonylmethyl]-1-[2-methoxy-4-(2-chlorobenzoylamino)benzoyl]-2,3,4,5-tetrahydro-1H-benzazepine.

26. 7-Chloro-5-[(4-methyl-1-piperazinyl)carbonylmethyl]-1-[2-methyl-4-(2-methylbenzoylamino)benzoyl]-2,3,4,5-tetrahydro-1H-benzazepine.

27. 7-Chloro-5-dimethylaminocarbonylmethyl-1-[2-methoxy-4-(2-chlorobenzoylamino)benzoyl]-2,3,4,5-tetrahydro-1H-benzazepine.

28. 7-Chloro-5-[2-(4-acetyl-1-piperazinyl)ethoxy]-1-[2-methyl-4-(2-methylbenzoylamino)benzoyl]-2,3,4,5-tetrahydro-1H-benzazepine.

29. 7-Chloro-5-[2-(4-acetyl-1-piperazinyl)ethyl]-1-[2-methyl-4-(2-methylbenzoylamino)benzoyl]-2,3,4,5-tetrahydro-1-H-benzazepine.

30. A vasopressin antagonistic composition which comprises as an active ingredient a compound of the formula (1) as set forth in claim 1, or a pharmaceutically acceptable salt thereof in admixture with a pharmaceutically acceptable carrier or diluent.

* * * * *